United States Patent
Dong et al.

(10) Patent No.: US 8,138,218 B2
(45) Date of Patent: Mar. 20, 2012

(54) GROWTH HORMONE SECRETAGOGUES

(75) Inventors: Zheng Xin Dong, Holliston, MA (US); John S. Eynon, Bellingham, MA (US); Yeelana Shen, Franklin, MA (US)

(73) Assignee: Ipsen Pharma S.A.S., Boulogne (FR)

( * ) Notice: Subject to any disclaimer, the term of this patent is extended or adjusted under 35 U.S.C. 154(b) by 881 days.

(21) Appl. No.: 11/989,181

(22) PCT Filed: Jul. 24, 2006

(86) PCT No.: PCT/US2006/029002
§ 371 (c)(1), (2), (4) Date: Mar. 12, 2008

(87) PCT Pub. No.: WO2007/014258
PCT Pub. Date: Feb. 1, 2007

(65) Prior Publication Data
US 2009/0131478 A1    May 21, 2009

Related U.S. Application Data

(60) Provisional application No. 60/701,729, filed on Jul. 22, 2005.

(51) Int. Cl.
| | |
|---|---|
| A01N 43/38 | (2006.01) |
| A01N 43/12 | (2006.01) |
| A01N 41/06 | (2006.01) |
| A01N 37/18 | (2006.01) |
| A61K 31/405 | (2006.01) |
| A61K 31/38 | (2006.01) |
| A61K 31/18 | (2006.01) |
| A61K 31/16 | (2006.01) |
| C07D 333/56 | (2006.01) |
| C07D 333/72 | (2006.01) |
| C07D 409/02 | (2006.01) |
| C07C 303/00 | (2006.01) |
| C07C 307/00 | (2006.01) |
| C07C 309/00 | (2006.01) |
| C07C 311/00 | (2006.01) |
| C07C 233/00 | (2006.01) |
| C07C 235/00 | (2006.01) |
| C07C 237/00 | (2006.01) |
| C07C 239/00 | (2006.01) |

(52) U.S. Cl. ........ 514/415; 514/443; 514/601; 514/613; 549/58; 564/84; 564/180

(58) Field of Classification Search ............ 514/415, 514/443, 601, 613; 549/58; 564/84, 180
See application file for complete search history.

(56) References Cited

U.S. PATENT DOCUMENTS
| | | | |
|---|---|---|---|
| 5,811,387 A | 9/1998 | Simon et al. | |
| 6,548,501 B2 | 4/2003 | Hakkinen | |
| 2002/0165343 A1* | 11/2002 | Martinez et al. | 530/331 |

FOREIGN PATENT DOCUMENTS
| | | |
|---|---|---|
| WO | WO 95/14666 | 6/1995 |
| WO | 01/92292 | 12/2001 |
| WO | WO0196300 | * 12/2001 |
| WO | WO 2004/014415 | 2/2004 |

OTHER PUBLICATIONS

Guerlavais, V. et al., "New active series of growth hormone secretagogues", J. Med. Chem., 2003:46:1191-1203.
Carter, D. S. et al., "Synthesis of homofascaplysin C and indolo[2,3-a]carbazole from ditryptophans", 1999, J. Org. Chem., 64:8537-8545.
Su, S. et al., "Synthesis and cell cycle inhibition of the peptide enamide natural products terpeptin and the aspergillamides", 2003, Tetrahedron, 59:8931-8946.
Ankersen,M. et al., "Growth hormone secretagogues derived from NN703 with hydrazides as c-terminal", 2000, Eur. J. Med. Chem., 35:487-497.
Crook, E. M. et al., "Synthetic plant growth hormones", 1937, Nature, Jan. 23, pp. 154-155.
Guerlavais, V. et al., "New growth hormone secretagogues", 2002, Letters in Peptide Science, 8:187-193.

* cited by examiner

*Primary Examiner* — Sreeni Padmanabhan
*Assistant Examiner* — Sarah Pihonak
(74) *Attorney, Agent, or Firm* — Yankwich & Associates; Alan F. Feeney

(57) ABSTRACT

A family of peptides and peptidomimetic compounds useful as GHS analogs according to either formula (I) or (II) as depicted below: or a pharmaceutically acceptable salts thereof, wherein the variables are as defined in the specification.

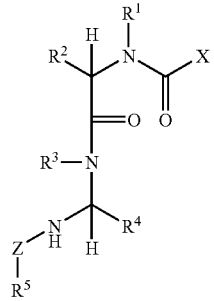

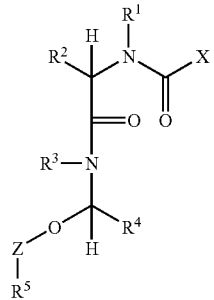

50 Claims, No Drawings

GROWTH HORMONE SECRETAGOGUES

This application is a United States national stage filing under 35 U.S.C. §371 of international (PCT) application No. PCT/US2006/029002, filed Jul. 24, 2006 and designating the US, which claims priority to U.S. provisional application 60/701,729, filed Jul. 22, 2005.

BACKGROUND OF THE INVENTION

The pulsatile release of growth hormone from the pituitary somatotrops is regulated by two hypothalamic neuropeptides: growth hormone-releasing hormone and somatostatin. Growth hormone-releasing hormone stimulates the release of growth hormone whereas somatostatin inhibits the secretion of growth hormone. (Frohman et al., *Endocrinology Review*, (1986), 7:223-253 and Strobi et al., *Pharmacol. Review*, (1994), 46:1-34).

Release of growth hormone from the pituitary somatotrops can also be controlled by growth hormone-releasing peptides (GHRP). The hexapeptide GHRP, His-D-Trp-Ala-Trp-D-Phe-Lys-amide (GHRP-6), was found to release growth hormone from the somatotrops in a dose-dependent manner in several species including man (Bowers et al., *Endocrinology*, (1984), 114:1537-45). Subsequent chemical studies on GHRP-6 led to the identification of other potent growth hormone secretagogues such as GHRP-I, GHRP-2 and hexarelin (Cheng et al., *Endocrinology*, (1989), 124:2791-8; Bowers, C. Y., *Novel GH-Releasing Peptides, Molecular and Clinical Advances in Pituitary Disorders*, Ed: Melmed, S., Endocrine Research and Education, Inc., Los Angeles, Calif., USA, (1993), 153-7 and Deghenghi et al., *Life Science*, (1994), 54:1321-8). The structures of these three growth hormone secretagogues are as shown:

GHRP-I     Ala-His-D-(2')-Nal-Ala-Trp-D-Phe-Lys-NH$_2$;

GHRP-2     D-Ala-D-(2')-Nal-Ala-Trp-D-Nal-Lys-NH$_2$;
and

Hexarelin     His-D-2-MeTrp-Ala-Trp-D-Phe-Lys-NH$_2$.

GHRP-I, GHRP-2, GHRP-6, and hexarelin are synthetic growth hormone secretagogues (hereinafter collectively referred to as "GHS"). GHS stimulate the secretion of growth hormone by a mechanism different from that of growth hormone-releasing hormone (Bowers, C. Y. et al., *Endocrinology*, (1984), 114:1537-45; Cheng et al., *Endocrinology*, (1989), 124:2791-8; Bowers, C. Y., *Novel GH-Releasing Peptides, Molecular and Clinical Advances in Pituitary Disorders*, Ed: Melmed, S., Endocrine Research and Education, Inc., Los Angeles, Calif., USA, (1993), 153-7 and Deghenghi et al., *Life Science*, (1994), 54:1321-8).

The low oral bioavailability (generally accepted as <1%) of these peptidyl growth hormone secretagogues encouraged the search for non-peptide compounds mimicking the action of GHRP-6 in the pituitary. Several benzolactams and spiroindanes have been reported to stimulate growth hormone release in various animal species and in man (Smith et al., *Science*, (1993), 260:1640-3; Patchett et al., *Proceedings of the National Academy Science USA*, (1995), 92:7001-5; and Chen et al., *Bioorganic Modern Chemistry Letter*, (1996), 6:2163-9). A specific example of such a small spiroindane is MK-0677 (Patchett et al., *Proceedings of the National Academy of Science, USA*, (1995), 92:7001-5) which has the following structure:

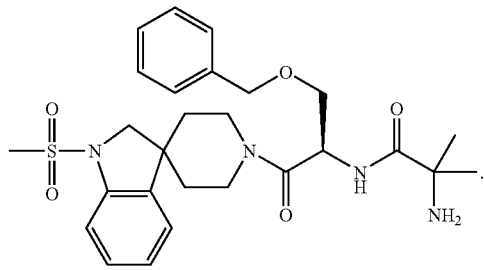

The actions of the above-mentioned GHS (both peptide and non-peptide) appear to be mediated by a specific growth hormone secretagogue receptor (hereinafter referred to collectively as "GHS receptor")(Howard et al., *Science*, (1996), 273:974-7 and Pong et al., *Molecular Endocrinology*, (1996), 10:57-61). The GHS receptor found in the pituitary and hypothalamus glands of various mammalian species (GHSR1a) is distinct from the growth hormone-releasing hormone receptor (hereinafter referred to as "GHRH receptor"). The GHS receptor was also detected in the other central nervous tissues and peripheral tissues such as the adrenal and thyroid glands, as well as heart, lung, kidney and skeletal muscle tissues (Chen et al., *Bioorganic Medical Chemistry Letter*, (1996), 6:2163-9; Howard et al., *Science*, (1996), 273:974-7; Pong et al., *Molecular Endocrinology*, (1996), 10:57-61; Guan et al., *Molecular Brain Research*, (1997), 48:23-9 and McKee et al., *Genomics*, (1997), 46:426-34). A truncated version of GHSR1a has also been reported. (Howard et al., *Science*, (1996), 273:974-7).

The GHS receptor is a G-protein coupled-receptor. Effects of GHS receptor activation include depolarization and inhibition of potassium channels, increase in intercellular concentrations of inositol triphosphate (IP3) and intracellular calcium concentrations, although transient for the latter (Pong et al., *Molecular Endocrinology*, (1996), 10:57-61; Guan et al., *Molecular Brain Research*, (1997), 48:23-9 and McKee et al., *Genomics*, (1997), 46:426-34).

Ghrelin is a naturally occurring peptide which is believed to be an endogenous ligand for the GHS receptor (Kojima et al., *Nature*, (1999), 402:656-60). The native structures of ghrelin from several mammalian and non-mammalian species are known (Kaiya et al., *Journal of Biological Chemisty*, (2001), 276:40441-8 and International Patent Application PCT/JP00/04907 [WO 01/07475]). A core region present in ghrelin was responsible for observed activity at the GHS receptor. The core region comprises the four N-terminal amino acids wherein the serine in the third position is normally modified with n-octanoic add. In addition to acylation by n-octanoic acid, native ghrelin may also be acylated with n-decanoic add (Kaiya et al., *Journal of Biological Chemistry*, (2001), 276:40441-8).

GHS molecules such as ghrelin and its analogs have a variety of different therapeutic (Inui, A., *FASEB J.*, (2004), 18:439-56; Muller et al., *Neurobiology of Aging*, (2002), 23:907-19; Casanueva, F. F. et al., *TEM*, (1999), 10:30-8 and Ankerson, M. et al., *DDT*, (1999) 4:497-506) and diagnostic uses. Compounds exhibiting agonist effects at the GHS receptor were found to promote the stimulation of growth hormone secretion. As such, analogs of ghrelin are indicated for improving a growth hormone-deficient state (U.S. Pat. Nos. 6,861,409; 6,967,237 and Casanueva, F. F. et al., *TEM*, (1999), 10:30-8), increasing muscle mass (U.S. Pat. Nos. 6,861,409 and 6,967,237) and/or physical strength (Ankerson, M. et al., *DDT* (1999), 4:497-506), improving bone density (U.S. Pat. Nos. 6,861,409, 6,967,237 and 6,251,902 and Sibilia, V. et al., *Growth Horm. IGF Res.*, (1999), 9:219-27), treating osteoporosis (WO 97/24369; WO 98/58947; Casanueva, F. F. et al., *TEM*, (1999), 10:30-8), overcoming male and female sexual dysfunction (U.S. Pat. No. 6,967,237; Casanueva, P. F. et al., *TEM*, (1999) 10:30-8), treating cardiovascular disease (WO 97/24369; WO 98/58947; U.S. Pat. No. 6,251,902; DeGennaro Colonna, V. et al., *Eur. J. Pharmacol.*, (1997), 334:201-7 and Casanueva, F. F. et al., *TEM*, (1999), 10:30-8), relieving arthritis pain (Granado, M., *AJP Endo.*, (2005), 288:486-92) and treating systemic lupus erythematosus or inflammatory bowel disease (e.g. Crohn's disease or ulcerative colitis) (U.S. Patent Publication 2002/0013320). Agonistic analogs of ghrelin can facilitate a gain in body weight (U.S. Pat. No. 6,967,237; Tschop, M. et al., *Endocrinology*, (2002), 143:558-68) which in turn can be used to maintain a desired body weight (U.S. Pat. Nos. 6,861,409 and 6,967,237) and/or to recover physical function (U.S. Pat. Nos. 6,967,237 and 6,251,02 and WO 97/24369).

Ghrelin also increases appetite (U.S. Pat. No. 6,967,237 and Okada, K. et al., *Endocrinology*, (1996), 137:5155-8). As such, ghrelin is used to treat patients suffering from certain diseases or disorders or undertaking medicinal regimens which are traditionally accompanied with an undesirable weight loss. Such diseases and disorders include anorexia (U.S. Pat. No. 6,967,237; Tschop, M. et al., *Endocrinology*, (2002), 143:558-68), bulimia (U.S. Pat. No. 6,967,237), cachexia (U.S. Pat. Nos. 6,967,237 and 6,251,902) particularly cancer-induced cachexia (U.S. Pat. No. 6,967,237 and Tschop, M. et al., *Endocrinology*, (2002), 143:558-68), AIDS (U.S. Pat. Nos. 6,861,409 and 6,967,237; Tschop, M. et al., *Endocrinology*, (2002), 143:558-68), wasting syndrome in the frail and/or elderly (U.S. Pat. Nos. 6,861,409 and 6,967, 237; WO 97/24369; Ankerson, M. et al., *DDT*, (1999), 4:497-506) and chronic renal failure (Casanueva, F. F. et al., *TEM*, (1999), 10:30-8). Medicinal treatments traditionally accompanied by a weight loss include chemotherapy, radiation therapy, temporary or permanent immobilization, and/or dialysis (U.S. Pat. Nos. 6,967,237 and 6,251,902).

Obesity is a major risk factor for diabetes and a large fraction of non-insulin-dependent diabetes mellitus (otherwise referred to as "NIDDM") patients are obese. Both conditions are characterized by elevated circulating insulin levels and suppressed GH levels. GH treatment of GH-deficient adults Jorgensen, J. O. L., et al., *Lancet*, (1989), 1:1221), obese women (Richelsen, B., et al., *Am J Physiol*, (1994), 266:E211) and elderly men (Rudman, D., et al, *Horm Res*, (1991), 36 (Suppl 1):73) has been shown to produce increases in lean body, hepatic and muscle mass while decreasing fat mass. Accordingly, administration of a ghrelin agonist is an attractive therapy for obesity except for the diabetogenic effects of GH (U.S. Pat. No. 6,251,902; Ankerson, M. et al., *DDT*, (1999), 4:497-506 and Casanueva, F. F. et al., *TEM*, (1999), 10:30-8). Complications of diabetes such as retinopathy and/or for treating cardiovascular disorders (U.S. Pat. No. 6,967,237; U.S. Patent Application Publication 2003/0211967) may be indirectly treated by ghrelin as well.

Paradoxically, ghrelin antagonists can be used to facilitate weight loss in an obese individual wherein said obesity is not due to the onset of NIDDM (U.S. Pat. No. 6,967,237 and U.S. Patent Application Publication 2003/0211967) as well as several other identified indications. Compounds exhibiting antagonist effects at the GHS receptor to promote the suppression of growth hormone secretion, e.g., antagonist analogs of ghrelin, are indicated for the treatment excessive growth hormone secretion (U.S. Patent Application Publication 2002/0187938), to facilitate weight loss in the non-obese (U.S. Pat. No. 6,967,237), to maintain an ideal weight and to decrease appetite (U.S. Pat. No. 6,967,237). Excessive weight is a contributing factor to many diseases or conditions such as hypertension, dyslipidemia and cardiovascular disease (U.S. Patent Application Publication 2003/0211967 and U.S. Pat. No. 6,967,237) as well as gall stones, osteoarthritis (U.S. Pat. No. 6,967,237), certain cancers (U.S. Patent Application Publications 2003/0211967 and 2004/0157227 and U.S. Pat. No. 6,967,237) and Prader-Willi syndrome (U.S. Pat. No. 6,950,707). Use of ghrelin antagonists to facilitate weight loss, therefore, would be useful to reduce the likelihood of such diseases or conditions and/or comprise at least part of a treatment for such diseases or conditions.

Analogs of growth hormone secretagogues have also been employed to promote gastrointestinal motility, particularly in patients suffering from decreased gastrointestinal motility resulting from post-operative ileus or from gastroparesis incidental to the onset of diabetes or a chronic diabetic state (U.S. Pat. No. 6,548,501).

Given the wide variety of beneficial effects that growth hormone secretagogues have to offer, there is a need in the art for effective agonist or antagonist GHS molecules.

SUMMARY OF THE INVENTION

The present invention features peptidyl analogs active at the GHS receptor. The analogs of the invention can bind to the GHS receptor and, preferably, bring about signal transduction. Thus, in a first aspect, the present invention features a compound according to formula (I):

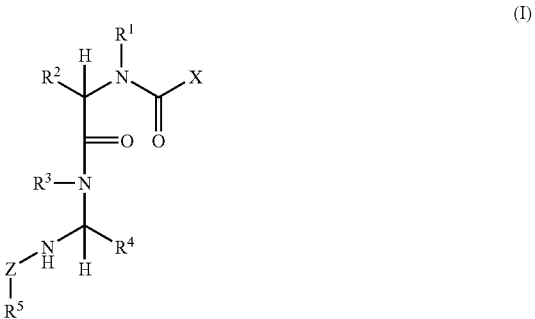

wherein
X is

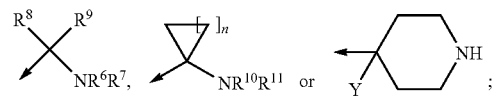

Y is H or $NR^{12}R^{13}$;

Z is —C(O)— or —$SO_2$—;

n is, independently for each occurrence, 1, 2, 3, 4, 5, 6, 7 or 8;

$R^1$ and $R^3$ each is, independently for each occurrence, H or $(C_1-C_4)$alkyl;

$R^2$ and $R^4$ each is, independently for each occurrence,

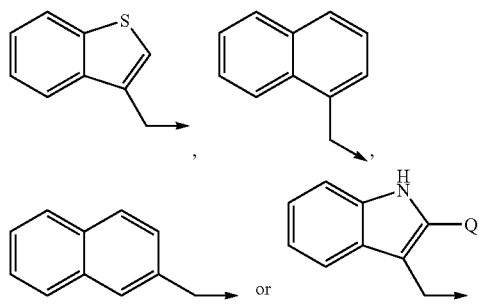

or $R^5$ is H, $(C_1-C_6)$alkyl, $(C_2-C_6)$alkenyl, $(C_2-C_6)$alkynyl, substituted $(C_1-C_6)$alkyl, substituted $(C_2-C_6)$alkenyl, substituted $(C_2-C_6)$alkynyl, aryl, alkylaryl, alkylarylalkyl or arylalkylaryl;

$R^8$ and $R^9$ each is, independently for each occurrence, $(C_1-C_6)$alkyl or substituted $(C_1-C_6)$alkyl;

$R^6$, $R^7$, $R^{10}$, $R^{11}$, $R^{12}$ and $R^{13}$ each is, independently for each occurrence, H, $(C_1-C_6)$alkyl or substituted $(C_1-C_6)$alkyl; and Q is H or $(C_1-C_4)$alkyl;

provided that both $R^2$ and $R^4$ are not

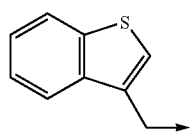

in the same compound;

or a pharmaceutically acceptable salt thereof.

A preferred group of compounds of the immediate foregoing formula is where at least one of $R^2$ and $R^4$ is:

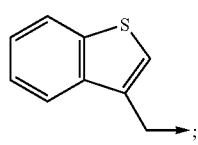

A preferred compound or pharmaceutically acceptable salt thereof, of formula (I), termed a Group 1 compound, is a compound according to formula (I) wherein:

$R^2$ is

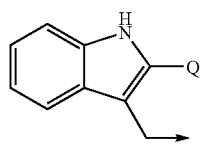

$R^4$ is

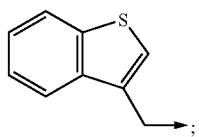

Z is —C(O)—;

X is

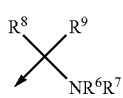

wherein $R^6$ and $R^7$ each is, independently, H and $R^8$ and $R^9$ each is, independently, $CH_3$; or X is

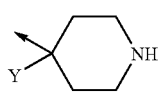

wherein Y is H; or

X is

wherein Y is $NR^{12}R^{13}$ and both $R^{12}$ and $R^{13}$ each is, independently, H;

$R^1$ is H;

$R^3$ is H or methyl; and $R^5$ is H, methyl, ethyl, isopropyl or t-butyl.

A preferred compound or a pharmaceutically acceptable salt thereof, of formula (I), termed a Group 1A compound, is a compound according to formula (I) wherein:

$R^2$ is

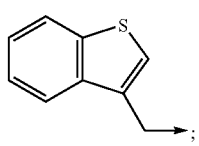

$R^4$ is

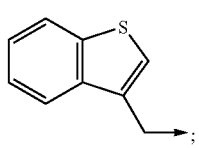

Z is —$SO_2$—;

X is
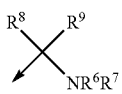
wherein $R^6$ and $R^7$ each is, independently, H and $R^8$ and $R^9$ each is, independently, $CH_3$; or
X is
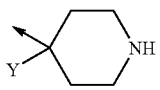
wherein Y is H; or
X is
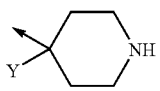
wherein Y is $NR^{12}R^{13}$ and both $R^{12}$ and $R^{13}$ each is, independently, H;
$R^1$ is H;
$R^3$ is H or methyl; and
$R^5$ is H, methyl, ethyl, isopropyl or t-butyl.
More preferred compounds of Group 1 or Group 1A are:
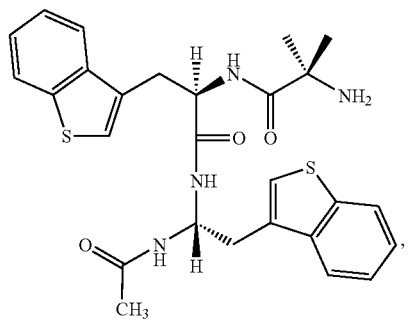
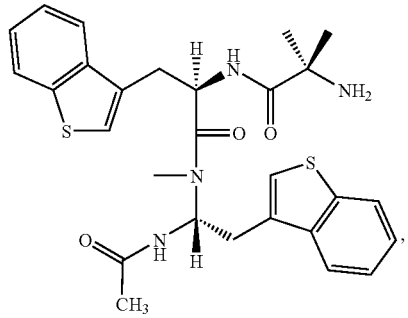
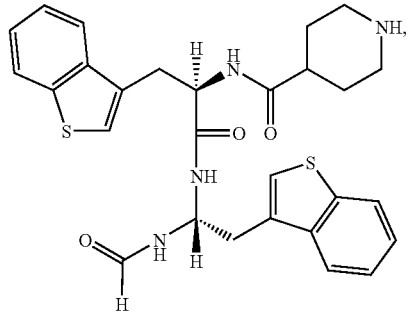
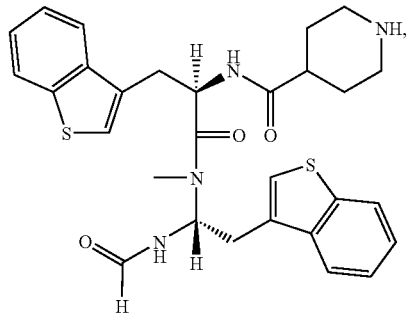
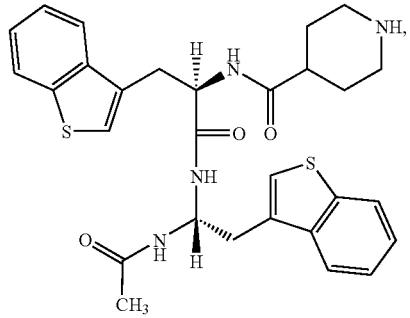

-continued
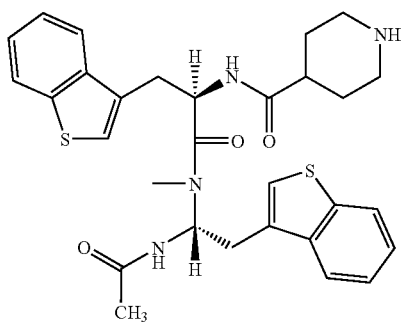
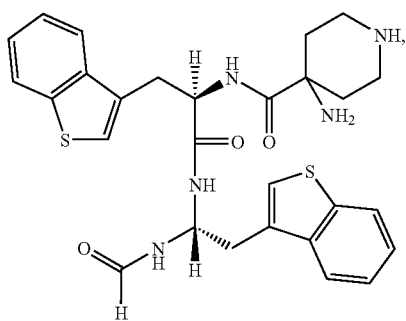
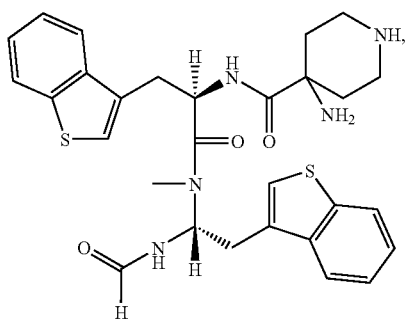
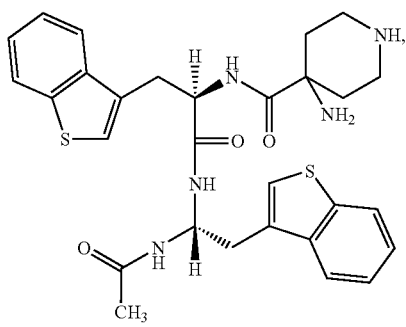
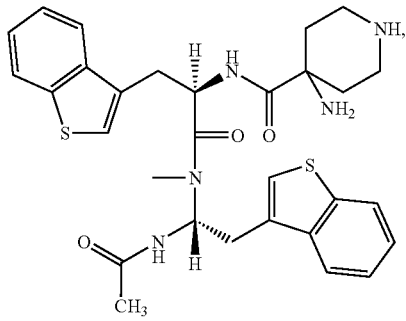
-continued
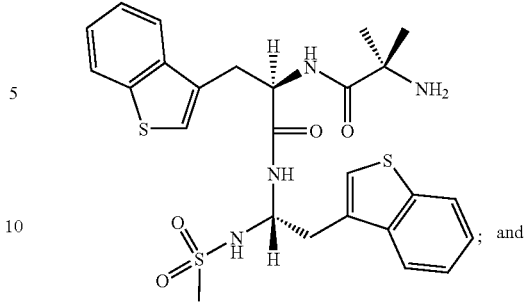
or a pharmaceutically acceptable salt thereof.
A preferred compound, or a pharmaceutically acceptable salt thereof, of formula (I), termed a Group 2 compound, is a compound according to formula (I) wherein:
$R^2$ is
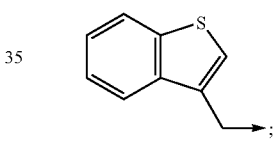
$R^4$ is
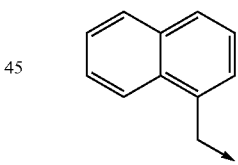
or
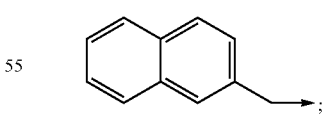
Z is —C(O)—;
X is
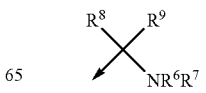

wherein $R^6$ and $R^7$ each is, independently, H and $R^8$ and $R^9$ each is, independently, $CH_3$; or X is

wherein Y is H; or

X is

wherein Y is $NR^{12}R^{13}$ and both $R^{12}$ and $R^{13}$ each is, independently, H;

$R^1$ is H;

$R^3$ is H or methyl; and $R^5$ is H, methyl, ethyl, isopropyl or t-butyl.

A preferred compound or a pharmaceutically acceptable salt thereof, of formula (I), termed a Group 2A compound, is a compound according to formula (I) wherein:

$R^2$ is

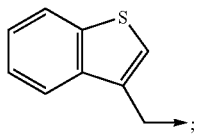

$R^4$ is

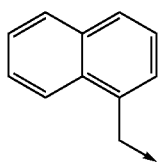

or

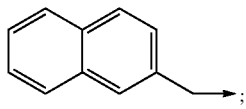

Z is —$SO_2$—;

X is

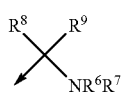

wherein $R^6$ and $R^7$ each is, independently, H and $R^8$ and $R^9$ each is, independently, $CH_3$; or X is

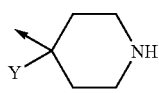

wherein Y is H; or

X is

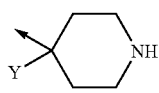

wherein Y is $NR^{12}R^{13}$ and both $R^{12}$ and $R^{13}$ each is, independently, H;

$R^1$ is H;

$R^3$ is H or methyl; and $R^5$ is H, methyl, ethyl, isopropyl or t-butyl

More preferred compounds of Group 2 or Group 2A are:

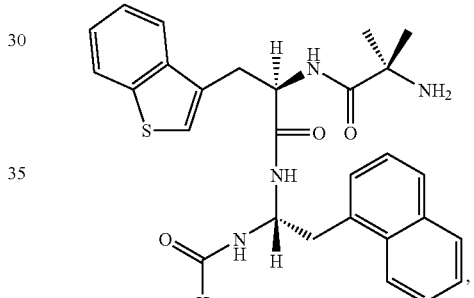

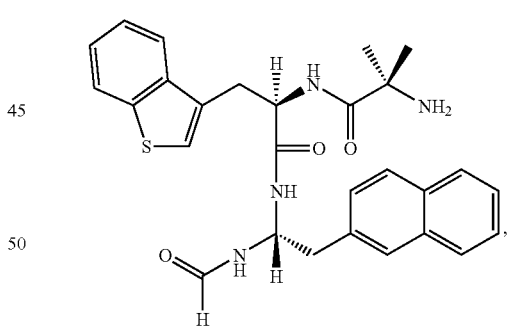

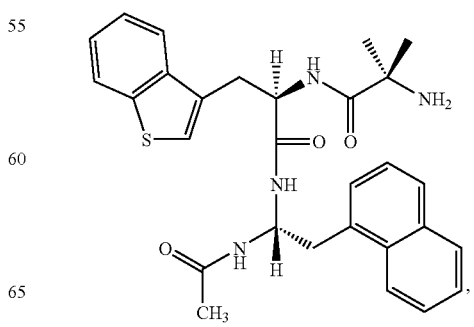

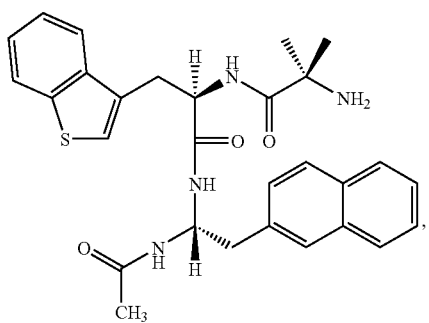
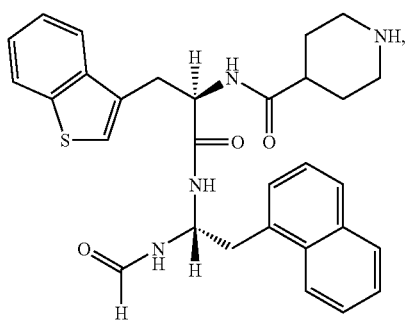
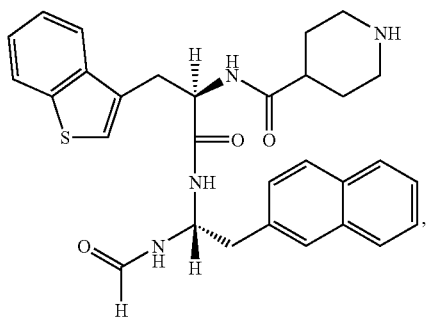
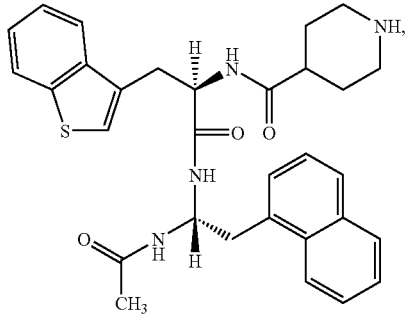
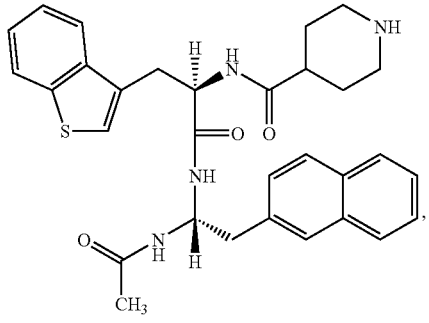
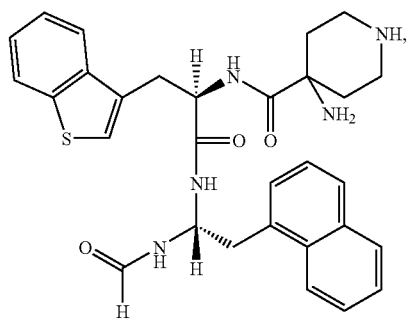
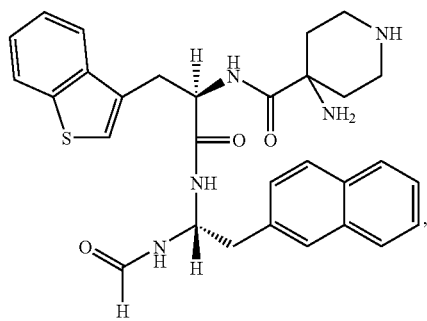
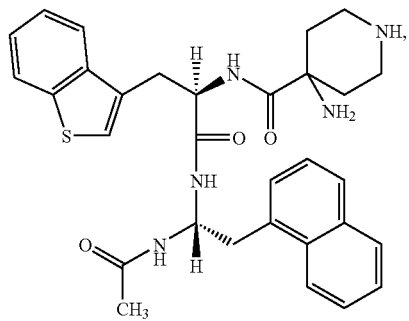
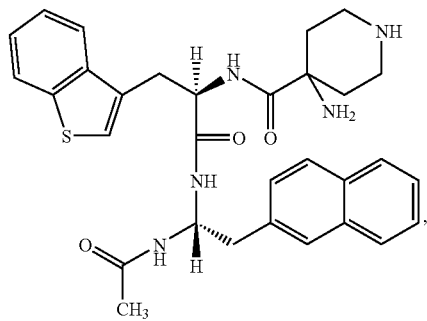
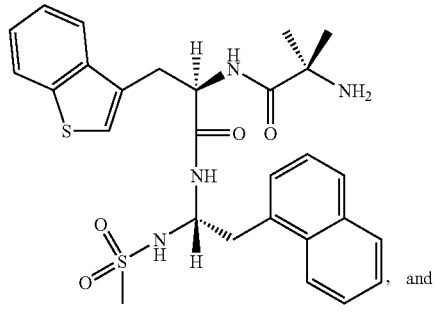
, and -continued

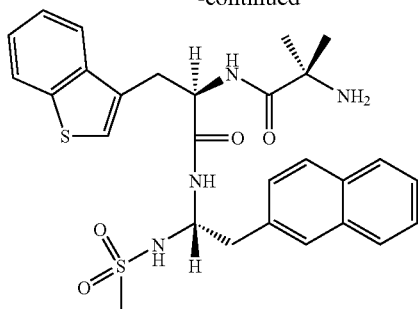

or a pharmaceutically acceptable salt thereof.

A preferred compound, or a pharmaceutically acceptable salt thereof, of formula (I), termed a Group 3 compound, is a compound according to formula (I) wherein:
$R^2$ is

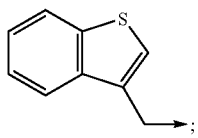

$R^4$ is

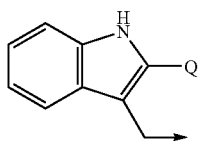

wherein Q is H;
Z is —C(O)—;
X is

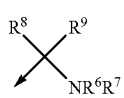

wherein $R^6$ and $R^7$ each is, independently, H and $R^8$ and $R^9$ each is, independently, $CH_3$; or
X is

wherein Y is H; or
X is

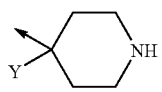

wherein Y is $NR^{12}R^{13}$ and both $R^{12}$ and $R^{13}$ each is, independently, H;

$R^1$ is H;
$R^3$ is H or methyl; and
$R^5$ is H, methyl, ethyl, isopropyl or t-butyl.

A preferred compound or pharmaceutically acceptable salt thereof, of formula (I), termed a Group 3A compound, is a compound according to formula (I) wherein:
$R^2$ is

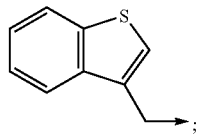

$R^4$ is

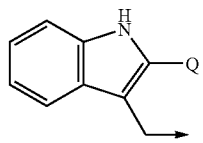

wherein Q is H;
Z is —$SO_2$—;
X is

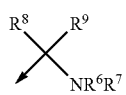

wherein $R^6$ and $R^7$ each is, independently, H and $R^8$ and $R^9$ each is, independently, $CH_3$; or
X is

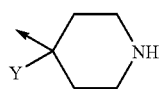

wherein Y is H; or
X is

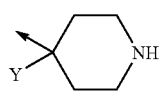

wherein Y is $NR^{12}R^{13}$ and both $R^{12}$ and $R^{13}$ each is, independently, H;
$R^1$ is H;
$R^3$ is H or methyl; and
$R^5$ is H, methyl, ethyl, isopropyl or t-butyl.

More preferred compounds of Group 3 or Group 3A are:
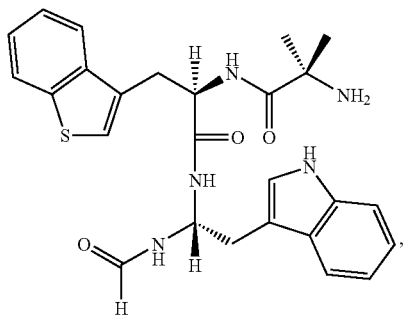
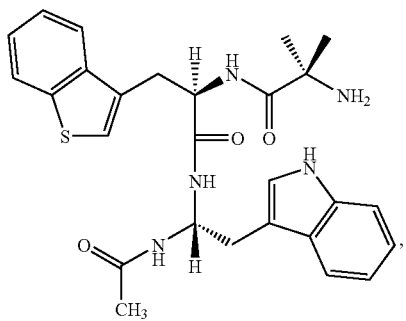
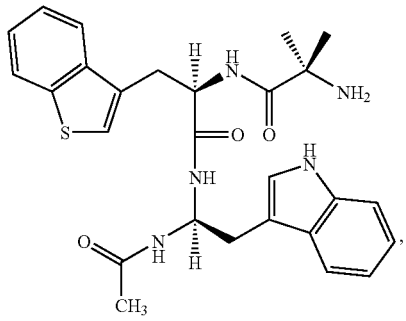
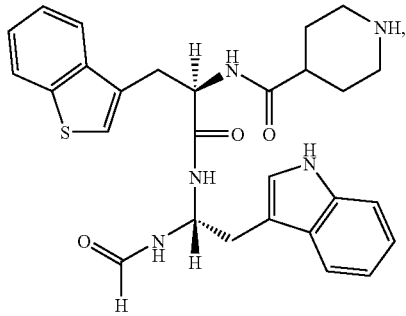
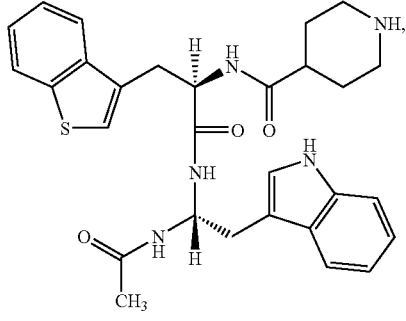
-continued
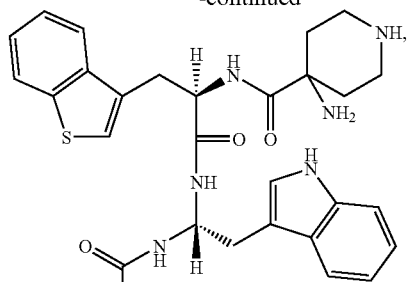
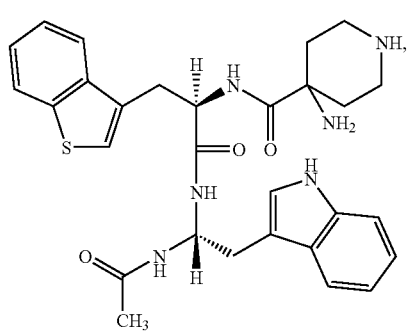
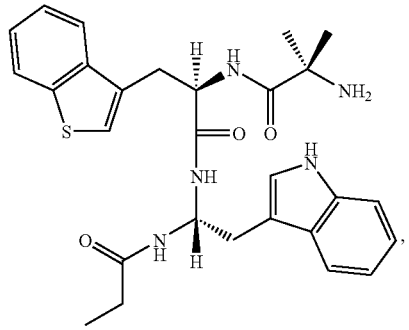
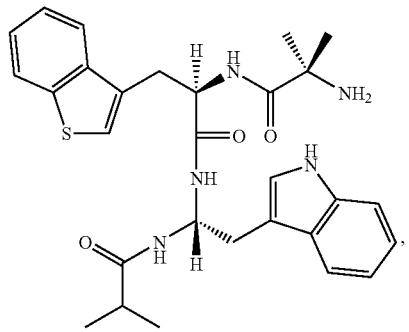
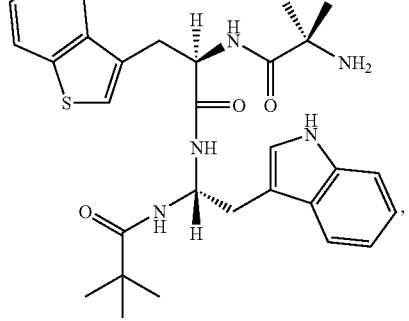

-continued

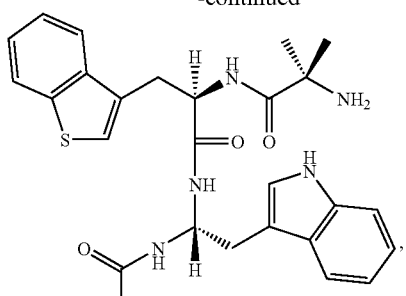,

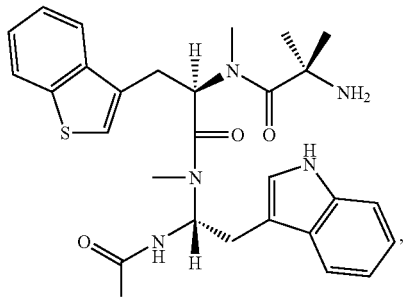,

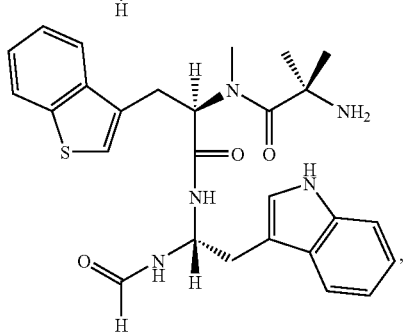,

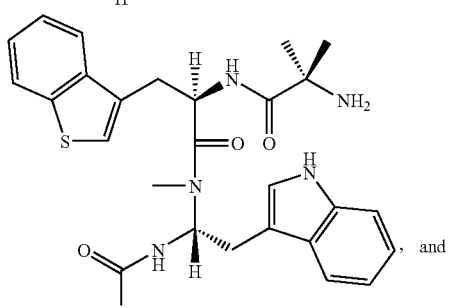, and

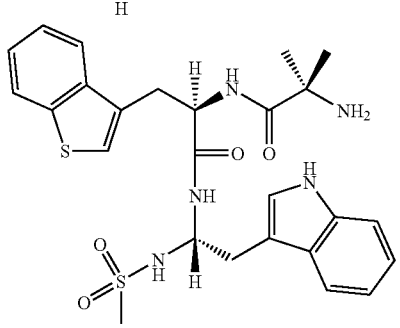

or a pharmaceutically acceptable salt thereof.

A preferred compound, or a pharmaceutically acceptable salt thereof, of formula (I), termed a Group 4 compound, is a compound according to formula (I) wherein:

$R^2$ is

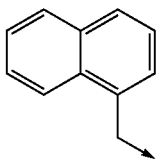

or

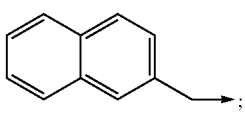;

$R^4$ is

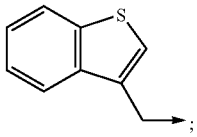;

Z is —C(O)—;
X is

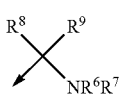

wherein $R^6$ and $R^7$ each is, independently, H and $R^8$ and $R^9$ each is, independently, $CH_3$; or
X is

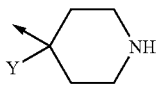

wherein Y is H; or
X is

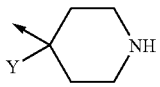

wherein Y is $NR^{12}R^{13}$ and both $R^{12}$ and $R^{13}$ each is, independently, H;
$R^1$ is H;
$R^3$ is H or methyl; and
$R^5$ is H, methyl, ethyl, isopropyl or t-butyl.

A preferred compound, or a pharmaceutically acceptable salt thereof, of formula (I), termed a Group 4A compound, is a compound according to formula (I) wherein:

R² is
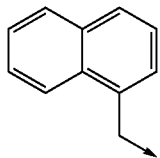
or
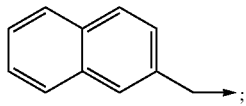
R⁴ is
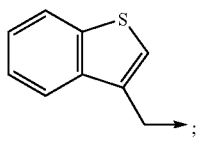
Z is —SO₂—;
X is
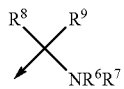
wherein R⁶ and R⁷ each is, independently, H and R⁸ and R⁹ each is, independently, CH₃; or
X is
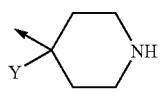
wherein Y is H; or
X is
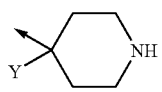
wherein Y is NR¹²R¹³ and both R¹² and R¹³ each is, independently, H;
R¹ is H;
R³ is H or methyl; and
R⁵ is H, methyl, ethyl, isopropyl or t-butyl.
More preferred compounds of Group 4 or Group 4A are:
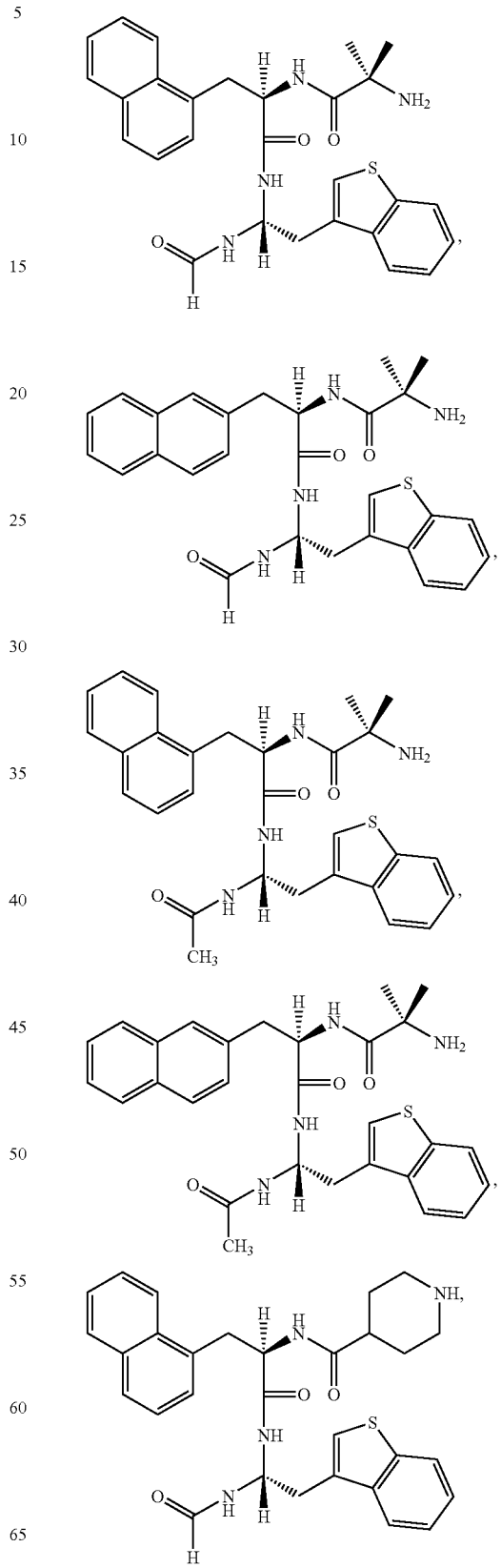

-continued
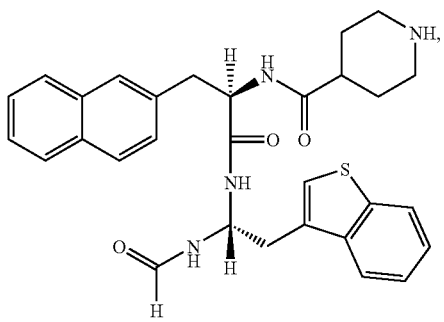
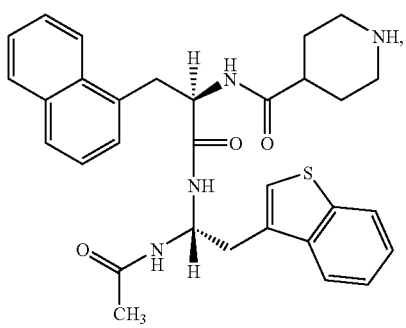
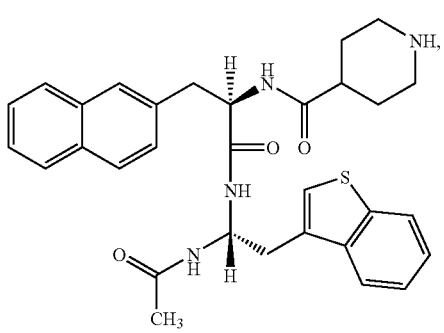
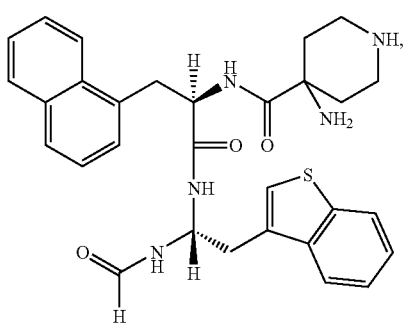
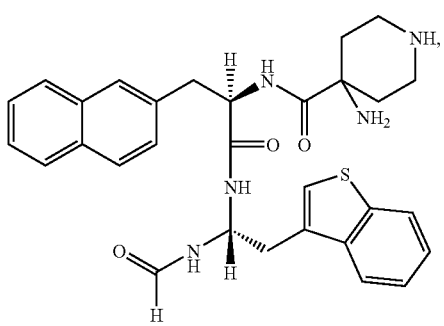
-continued
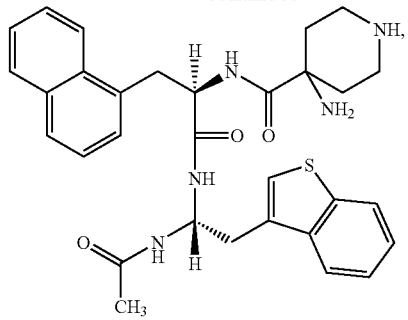
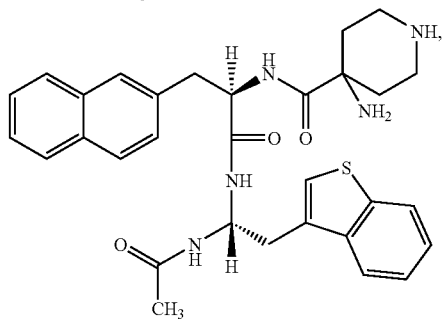
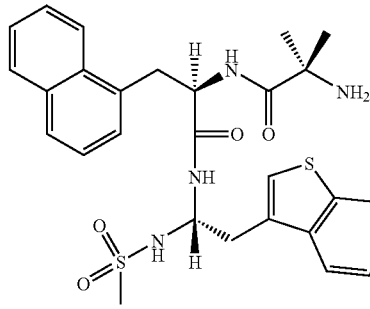
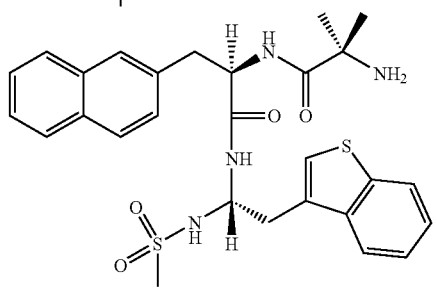
, and
or a pharmaceutically acceptable salt thereof.
A preferred compound, or a pharmaceutically acceptable salt thereof, of formula (I), termed a Group 5 compound, is a compound according to formula (I) wherein:
$R^2$ is
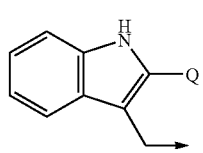
wherein Q is H;

$R^4$ is

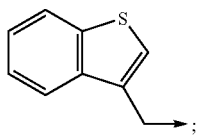

$Z$ is —C(O)—;
$X$ is

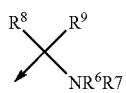

wherein $R^6$ and $R^7$ each is, independently, H and $R^8$ and $R^9$ each is, independently, $CH_3$; or
$X$ is

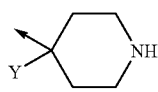

wherein Y is H; or
$X$ is

wherein Y is $NR^{12}R^{13}$ and both $R^{12}$ and $R^{13}$ each is, independently, H;
$R^1$ is H;
$R^3$ is H or methyl; and
$R^5$ is H, methyl, ethyl, isopropyl or t-butyl.

A preferred compound or pharmaceutically acceptable salt thereof, of formula (I), termed a Group 5A compound, is a compound according to formula (I) wherein:
$R^2$ is

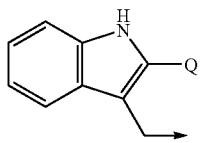

wherein Q is H;
$R^4$ is

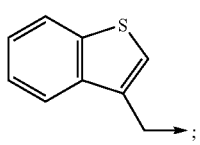

$Z$ is —$SO_2$—;
$X$ is

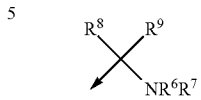

wherein $R^6$ and $R^7$ each is, independently, H and $R^8$ and $R^9$ each is, independently, $CH_3$; or
$X$ is

wherein Y is H; or
$X$ is

wherein Y is $NR^{12}R^{13}$ and both $R^{12}$ and $R^{13}$ each is, independently, H;
$R^1$ is H;
$R^3$ is H or methyl; and
$R^5$ is H, methyl, ethyl, isopropyl or t-butyl.

More preferred compounds of Group 5 or Group 5A are:

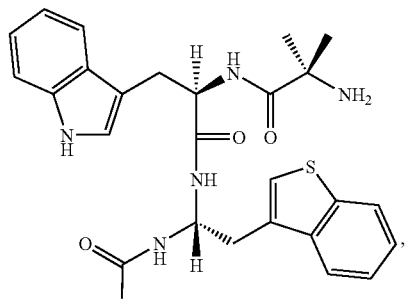

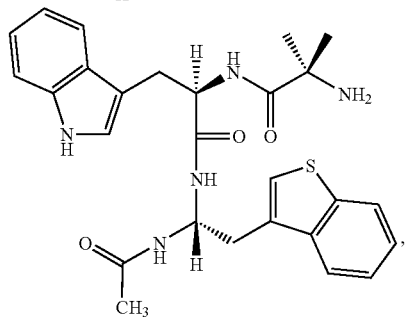

-continued

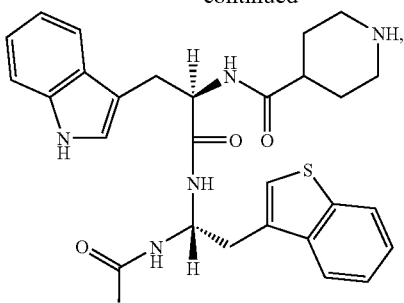

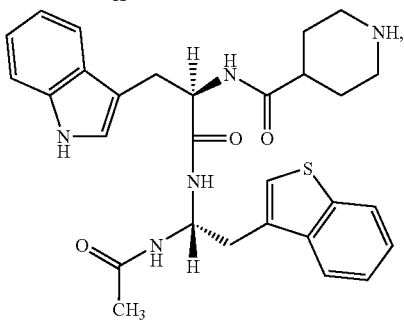

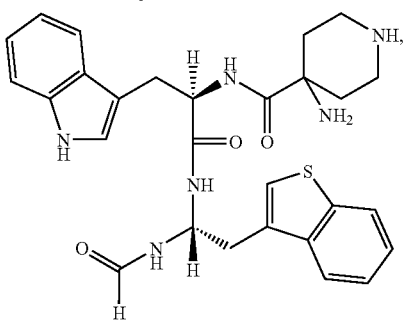

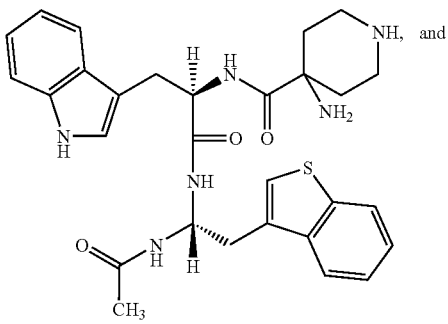

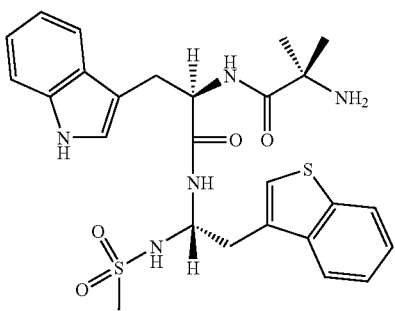

or a pharmaceutically acceptable salt thereof.

A preferred compound, or a pharmaceutically acceptable salt thereof, of formula (I), termed a Group 6 compound, is a compound according to formula (I) wherein:

$R^2$ is

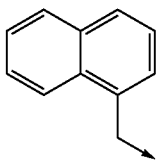

or

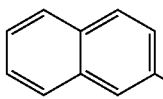

;

$R^4$ is

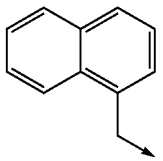

or

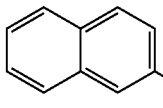

;

Z is —C(O)—;
X is

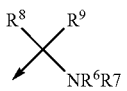

wherein $R^6$ and $R^7$ each is, independently, H and $R^8$ and $R^9$ each is, independently, $CH_3$; or
X is

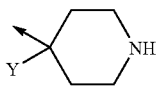

wherein Y is H; or
X is

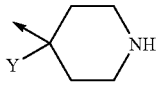

wherein Y is $NR^{12}R^{13}$ and both $R^{12}$ and $R^{13}$ each is, independently, H;
$R^1$ is H;
$R^3$ is H or methyl; and
$R^5$ is H, methyl, ethyl, isopropyl or t-butyl.

A preferred compound or pharmaceutically acceptable salt thereof, of formula (I), termed a Group 6A compound, is a compound according to formula (I) wherein:

R² is

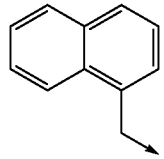

or

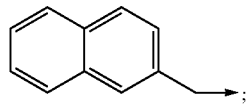

R⁴ is

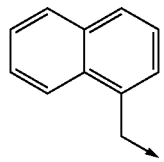

or

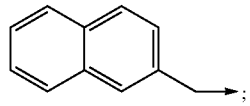

Z is —SO₂—;
X is

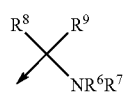

wherein R⁶ and R⁷ each is, independently, H and R⁸ and R⁹ each is, independently, CH₃; or X is

wherein Y is H; or

X is

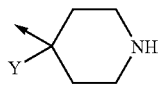

wherein Y is NR¹²R¹³ and both R¹² and R¹³ each is, independently, H;
R¹ is H;
R³ is H or methyl; and
R⁵ is H, methyl, ethyl, isopropyl or t-butyl.

More preferred compounds of Group 6 or Group 6A are:

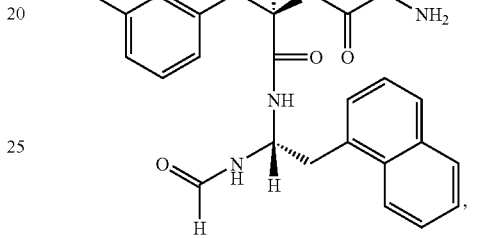

,

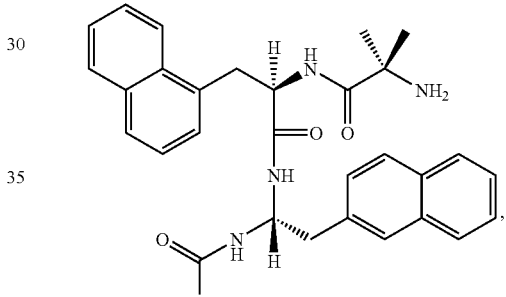

,

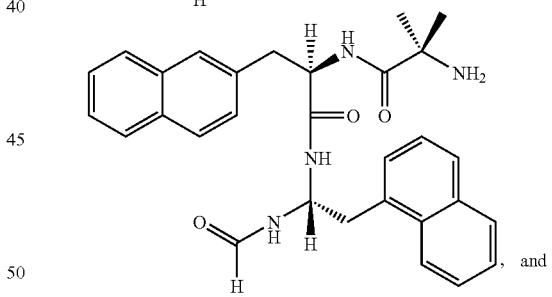

, and

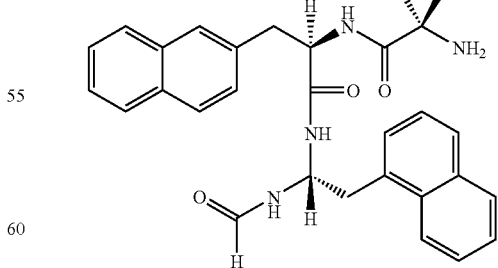

or a pharmaceutically acceptable salt thereof.

A preferred compound, or a pharmaceutically acceptable salt thereof, of formula (I), termed a Group 7 compound, is a compound according to formula (I) wherein:

$R^2$ is

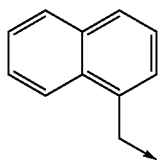

or

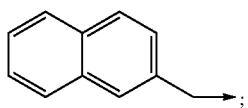

$R^4$ is

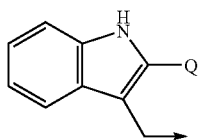

wherein Q is H;
Z is —C(O)—;
X is

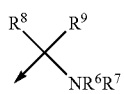

wherein $R^6$ and $R^7$ each is, independently, H and $R^8$ and $R^9$ each is, independently, $CH_3$; or
X is

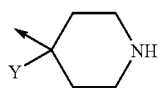

wherein Y is H; or
X is

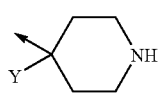

wherein Y is $NR^{12}R^{13}$ and both $R^{12}$ and $R^{13}$ each is, independently, H;
$R^1$ is H;
$R^3$ is H or methyl; and
$R^5$ is H, methyl, ethyl, isopropyl or t-butyl.

A preferred compound or pharmaceutically acceptable salt thereof, of formula (I), termed a Group 7A compound, is a compound according to formula (I) wherein:

$R^2$ is

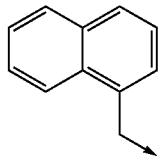

or

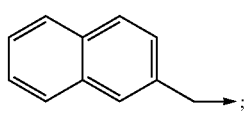

$R^4$ is

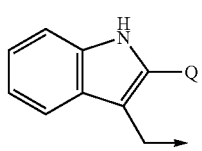

wherein Q is H;
Z is —$SO_2$—;
X is

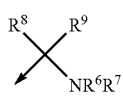

wherein $R^6$ and $R^7$ each is, independently, H and $R^8$ and $R^9$ each is, independently, $CH_3$; or
X is

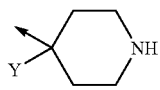

wherein Y is H; or
X is

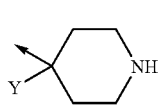

wherein Y is $NR^{12}R^{13}$ and both $R^{12}$ and $R^{13}$ each is, independently, H;
$R^1$ is H;
$R^3$ is H or methyl; and
$R^5$ is H, methyl, ethyl, isopropyl or t-butyl.

More preferred compounds of Group 7 or Group 7A are:

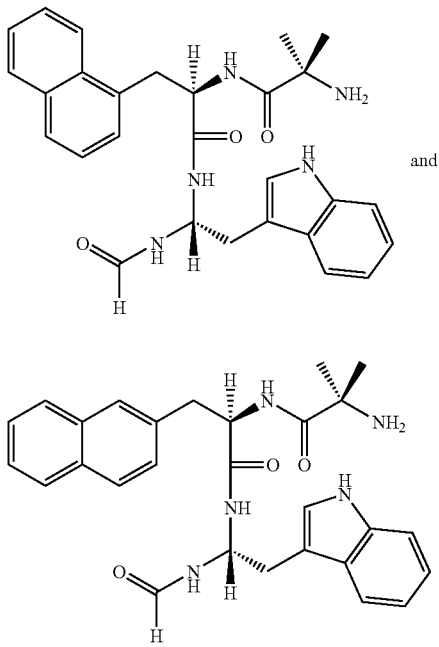

and or a pharmaceutically acceptable salt thereof.

A preferred compound, or a pharmaceutically acceptable salt thereof, of formula (I), termed a Group 8 compound, is a compound according to formula (I) wherein:

$R^2$ is

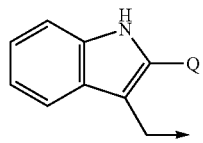

wherein Q is H;

$R^4$ is

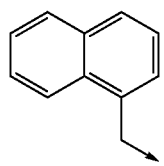

or

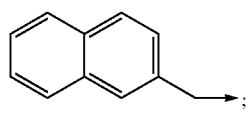

Z is —C(O)—;

X is

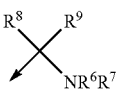

wherein $R^6$ and $R^7$ each is, independently, H and $R^8$ and $R^9$ each is, independently, $CH_3$; or X is

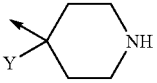

wherein Y is H; or

X is

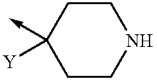

wherein Y is $NR^{12}R^{13}$ and both $R^{12}$ and $R^{13}$ each is, independently, H;

$R^1$ is H;

$R^3$ is H or methyl; and $R^5$ is H, methyl, ethyl, isopropyl or t-butyl.

A preferred compound or pharmaceutically acceptable salt thereof, of formula (I), termed a Group 8A compound, is a compound according to formula (I) wherein:

$R^2$ is

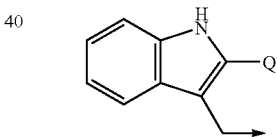

wherein Q is H;

$R^4$ is

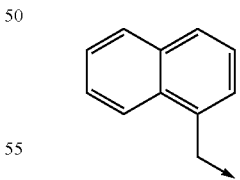

or

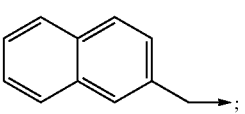

Z is —$SO_2$—;

X is

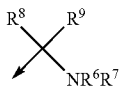

wherein $R^6$ and $R^7$ each is, independently, H and $R^8$ and $R^9$ each is, independently, $CH_3$; or X is

wherein Y is H; or

X is

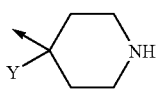

wherein Y is $NR^{12}R^{13}$ and both $R^{12}$ and $R^{13}$ each is, independently, H;

$R^1$ is H;

$R^3$ is H or methyl; and $R^5$ is H, methyl, ethyl, isopropyl or t-butyl.

More preferred compounds of Group 8 or Group 8A are:

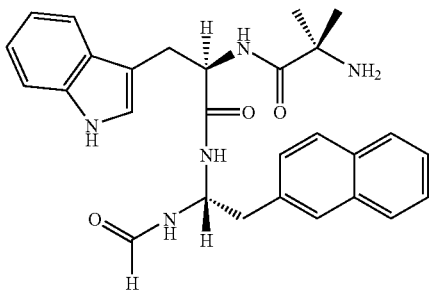

and

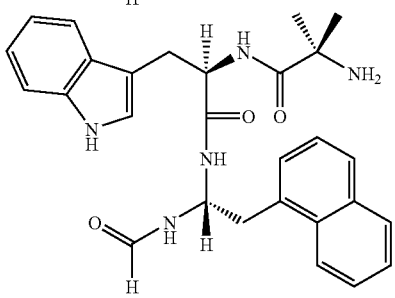

or a pharmaceutically acceptable salt thereof.

Another preferred compound of formula (I), termed Group 9, is a compound according to the formula:

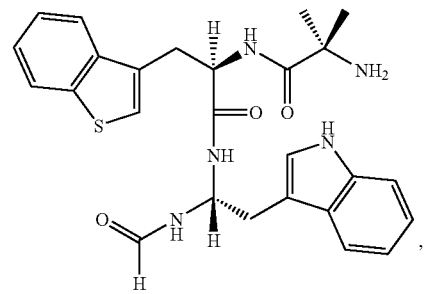

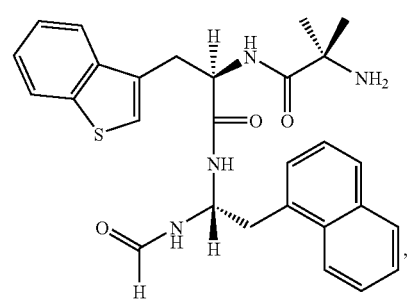

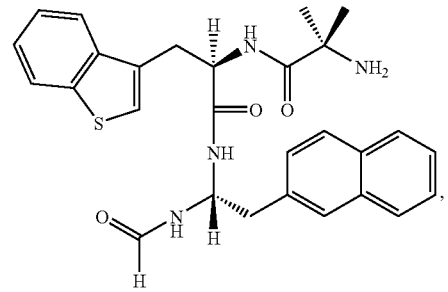

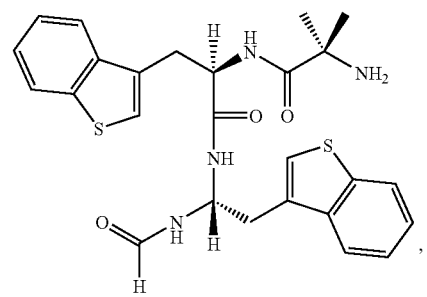

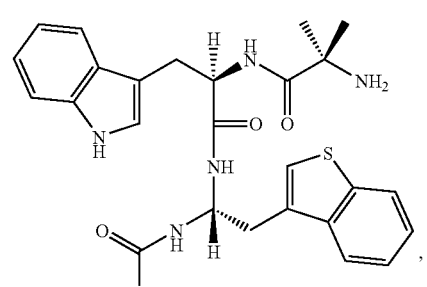

37
-continued
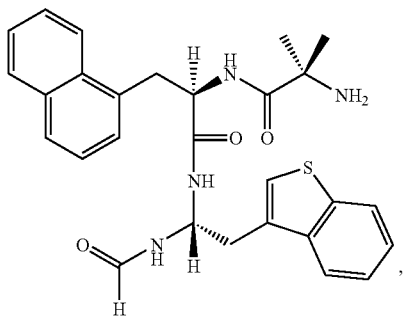
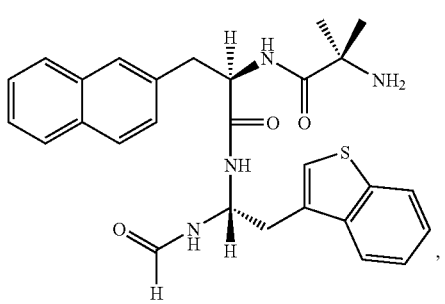
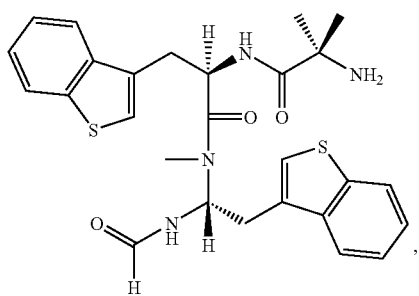
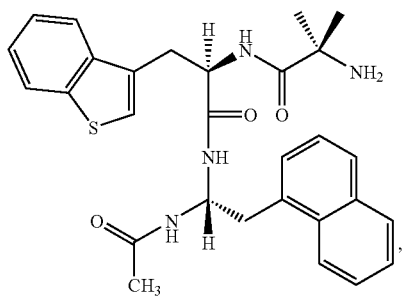
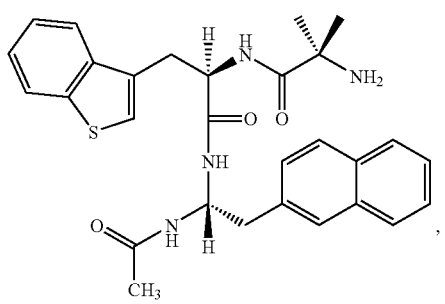
38
-continued
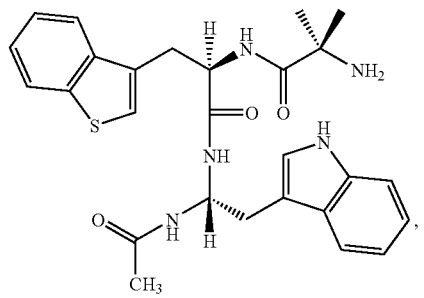
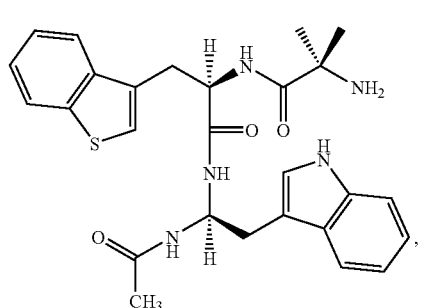
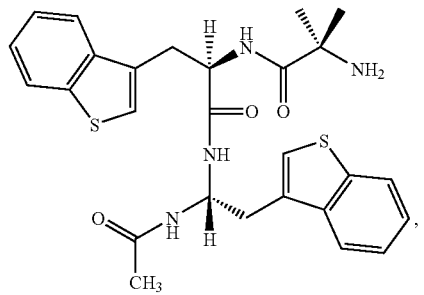
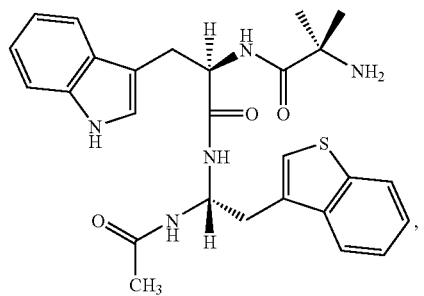
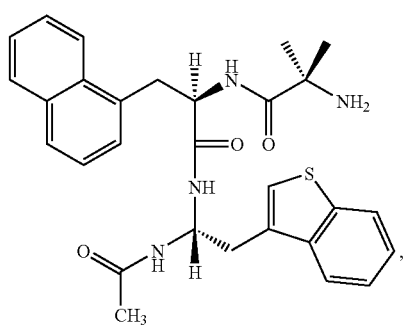

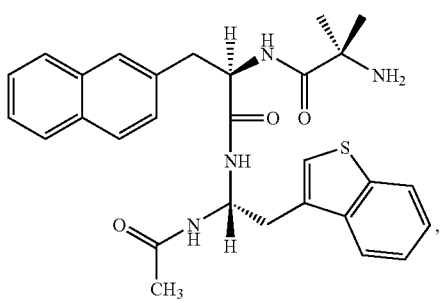
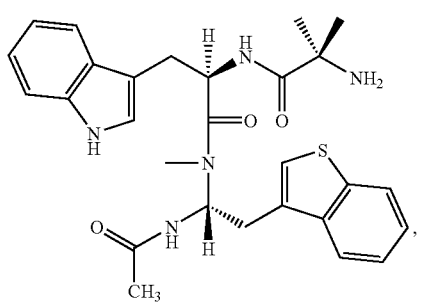
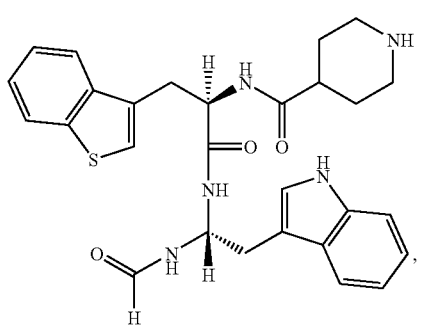
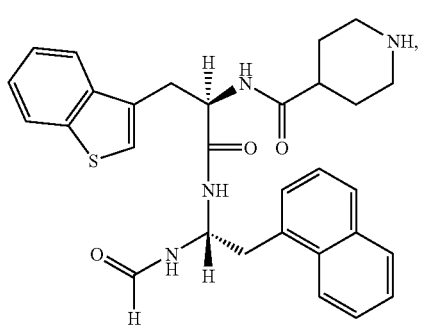
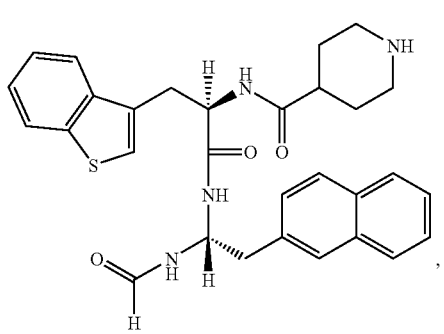
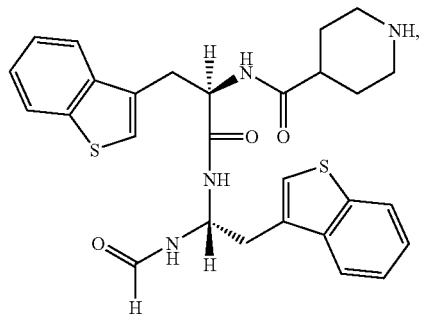
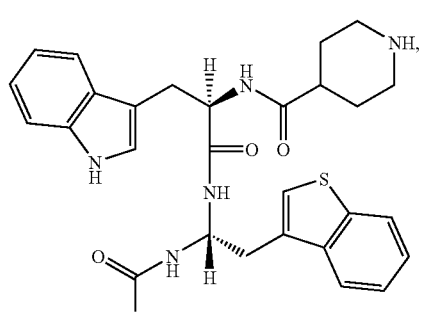
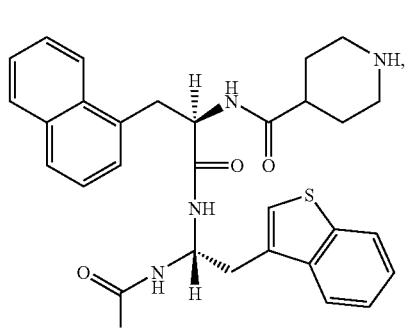
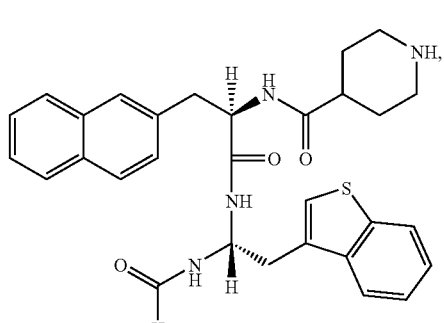
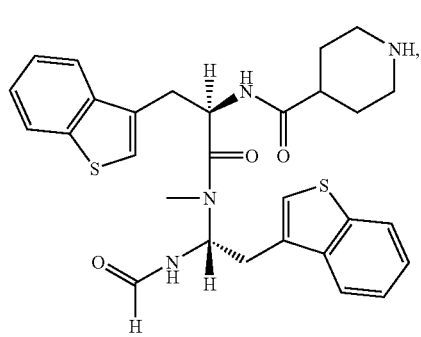

-continued
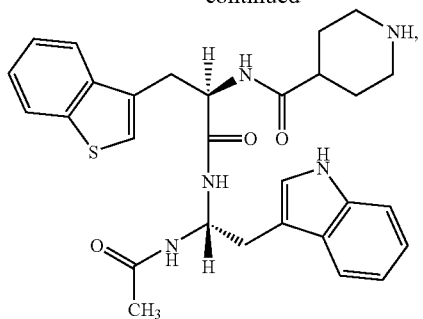
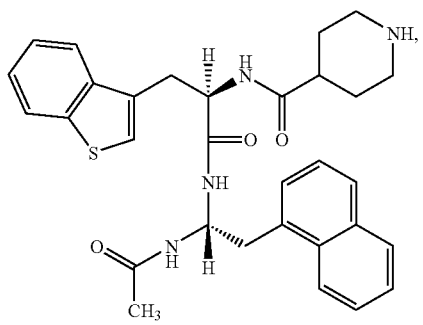
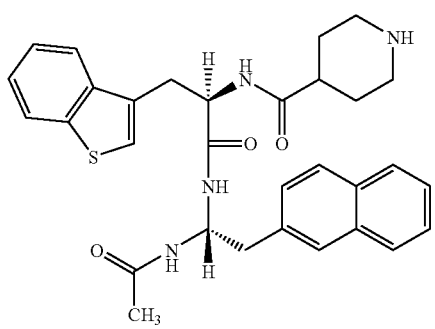
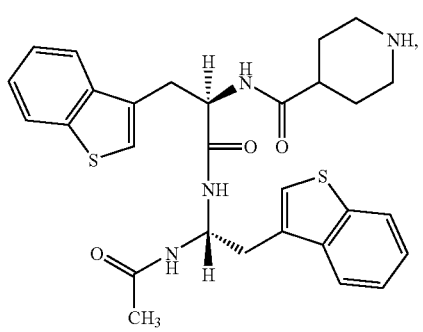
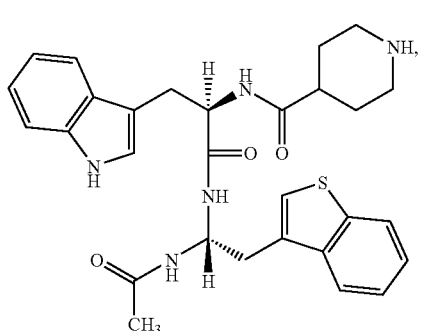
-continued
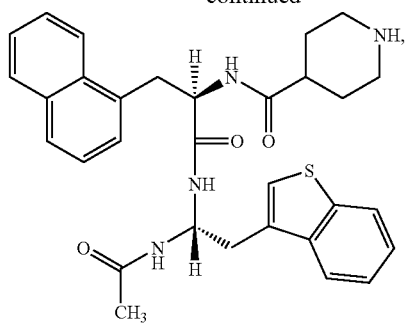
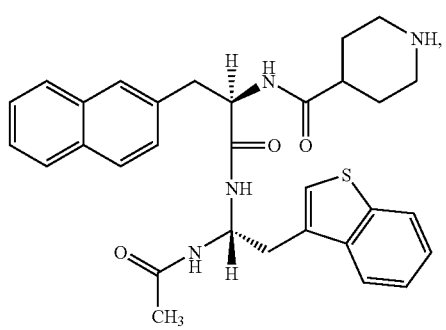
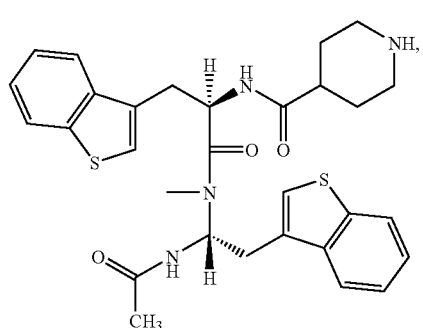
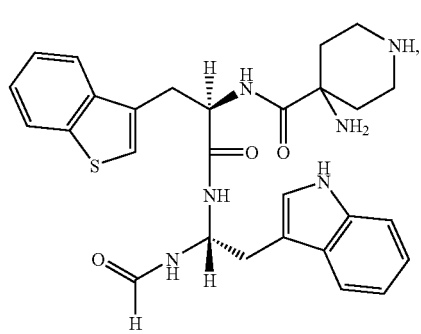
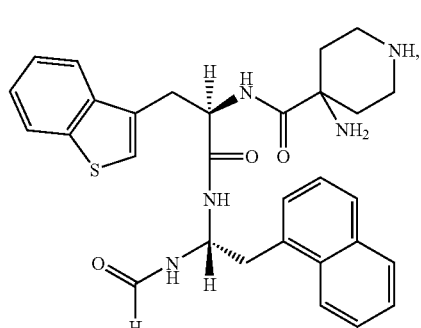

43
-continued
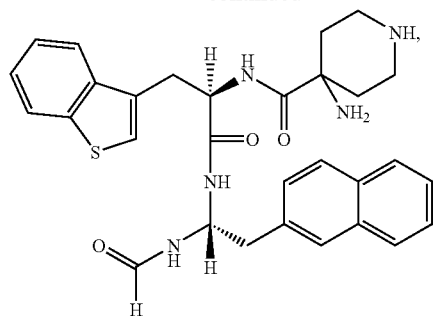
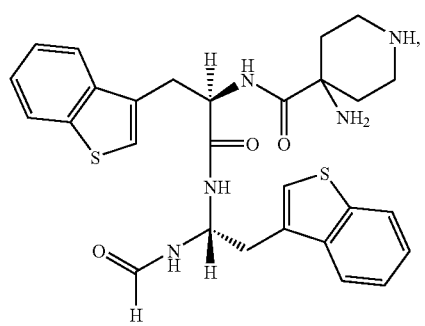
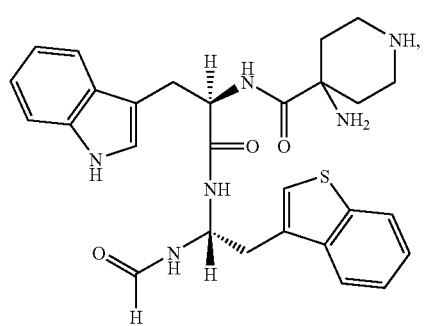
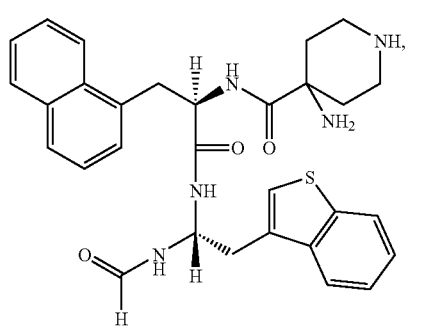
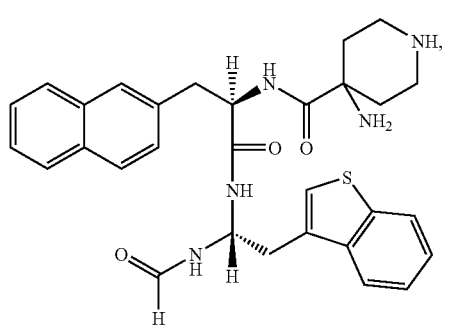
44
-continued
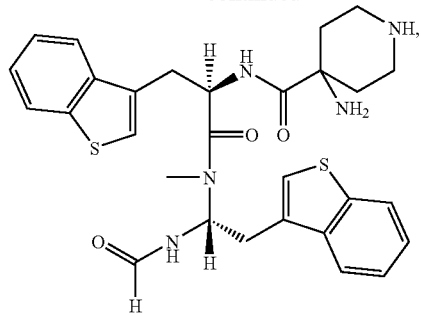
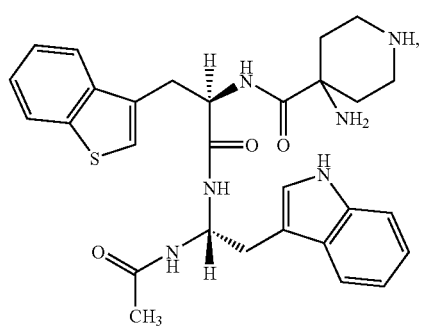
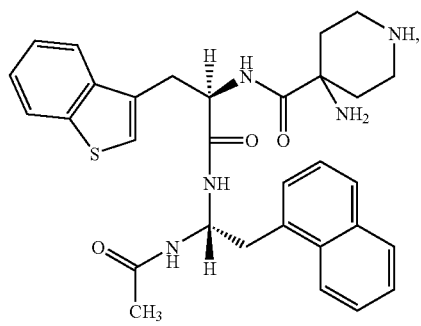
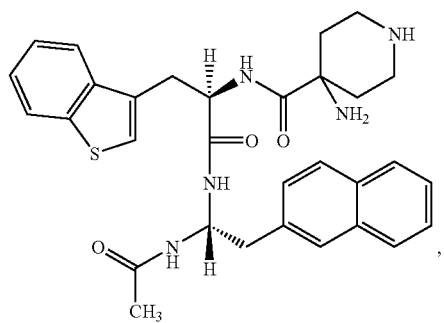
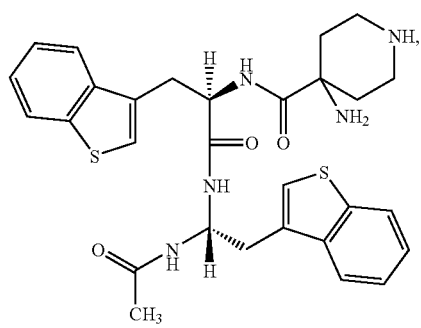

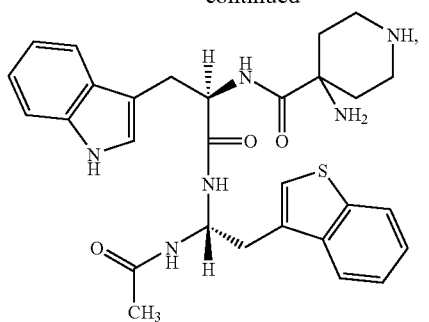
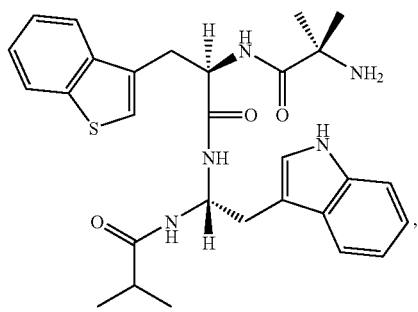
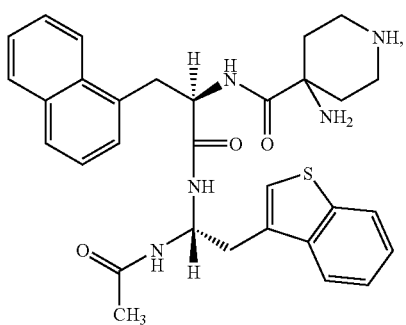
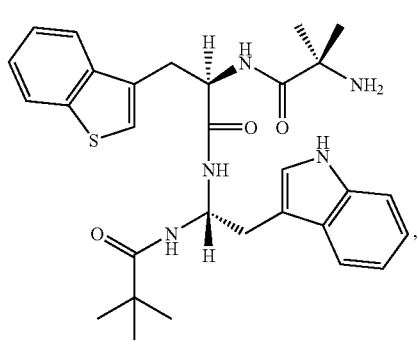
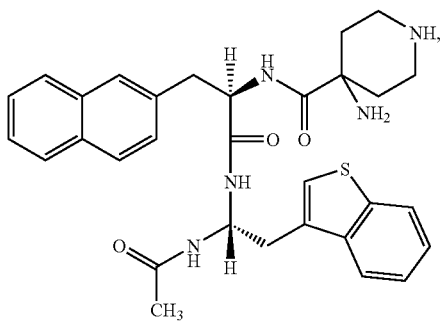
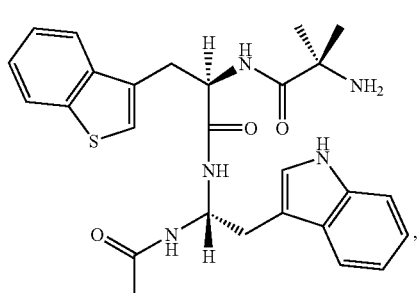
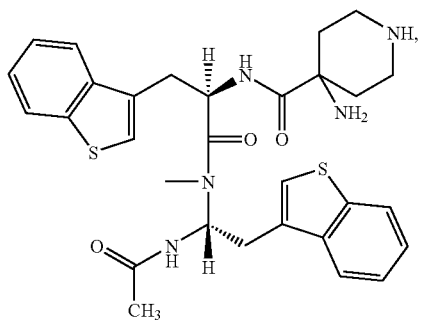
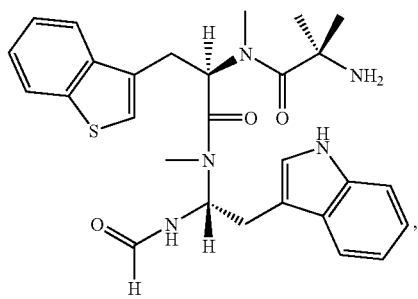
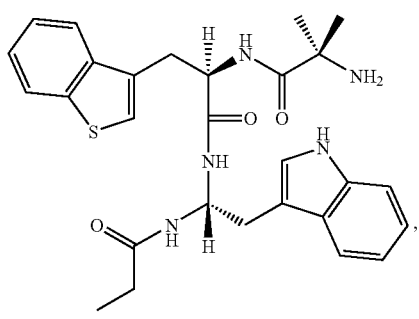
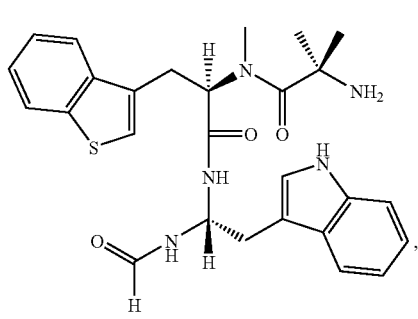

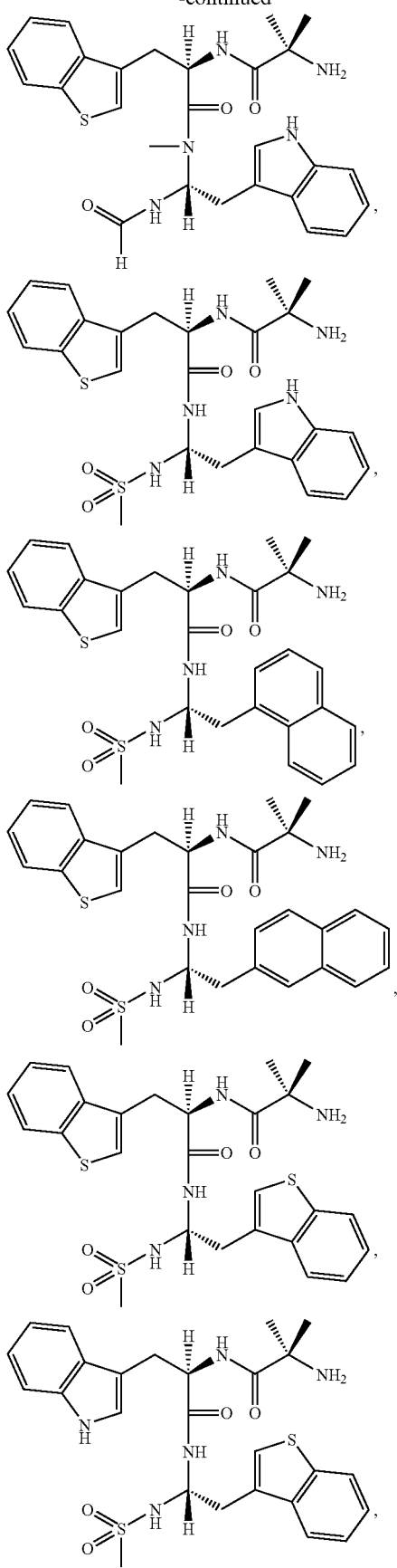
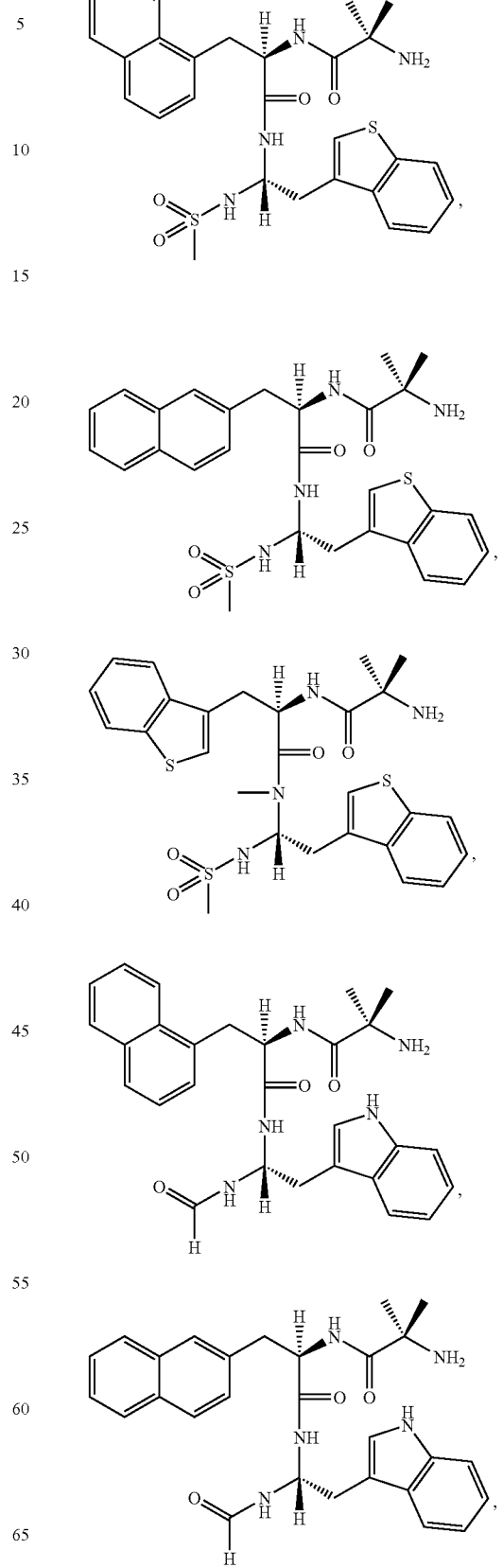

-continued
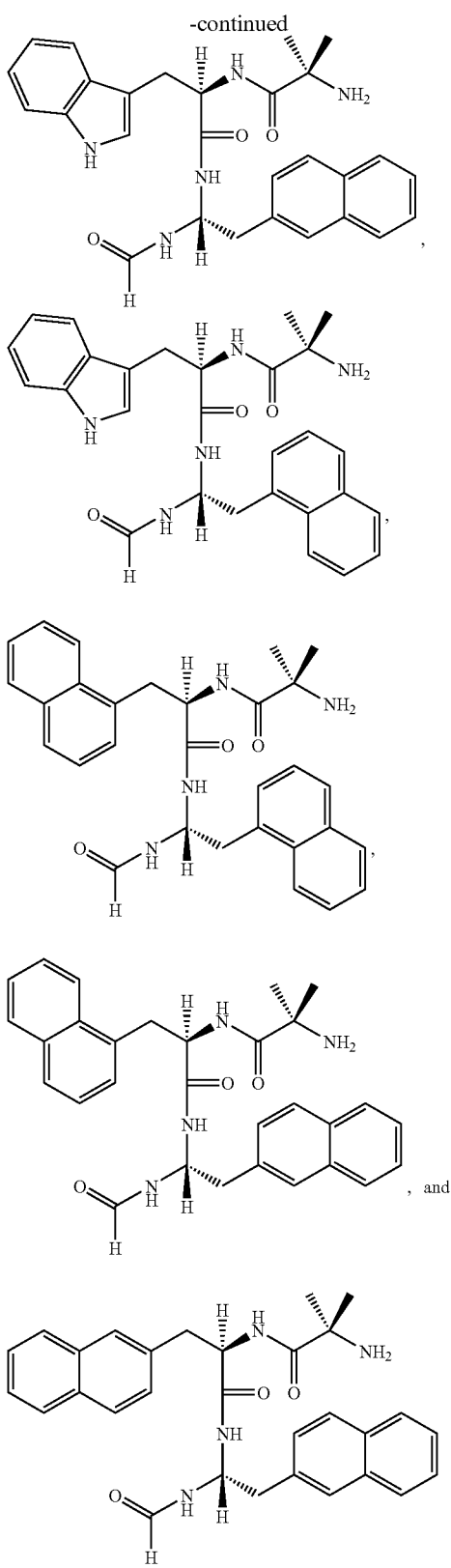
or a pharmaceutically acceptable salt thereof.
A pharmaceutical composition containing a compound of the immediately foregoing group of compounds with a pharmaceutically acceptable carrier is preferred.
A preferred compound of Group 9 is a compound of Group 9A, according to
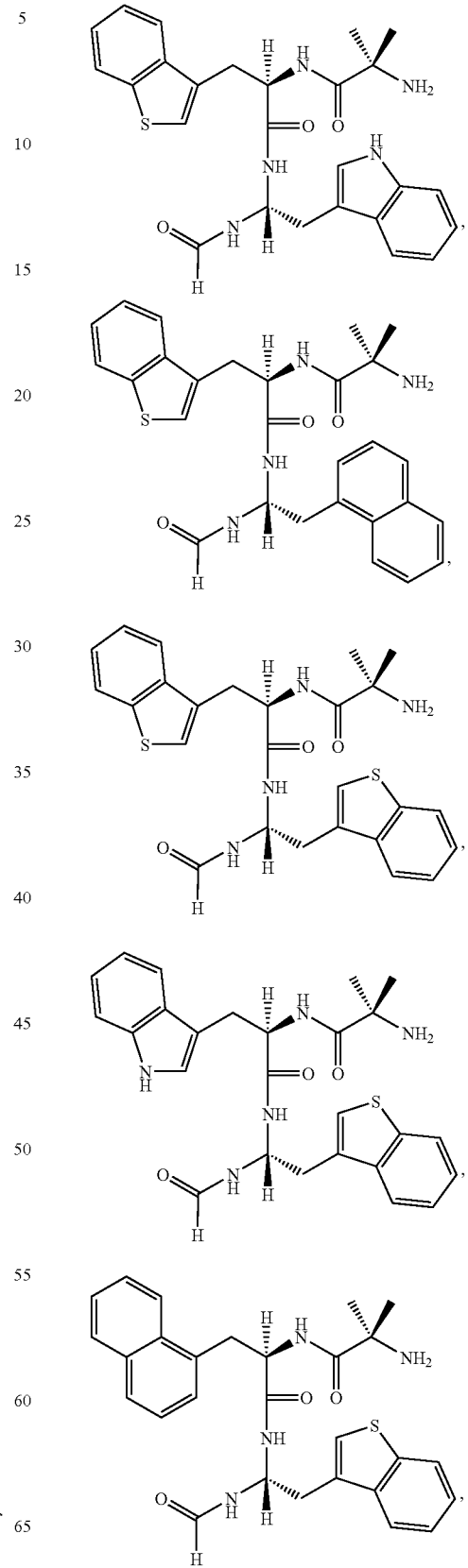

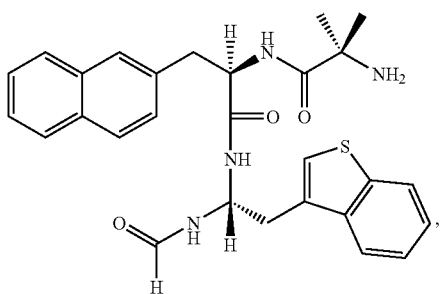
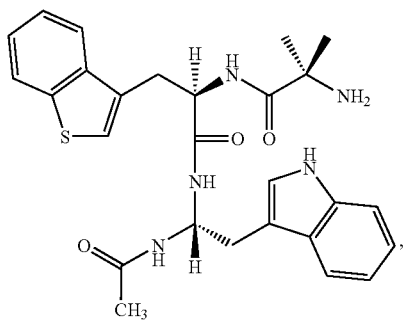
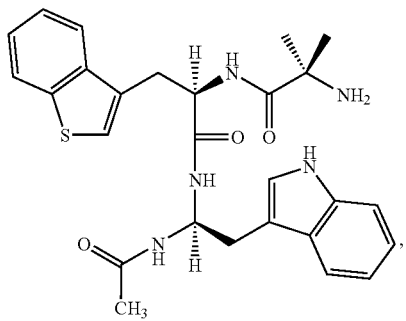
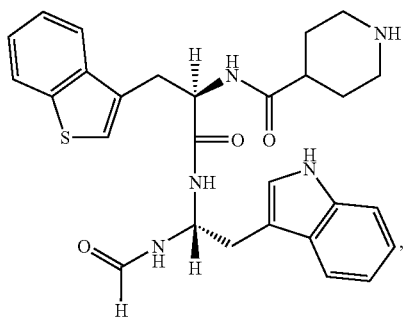
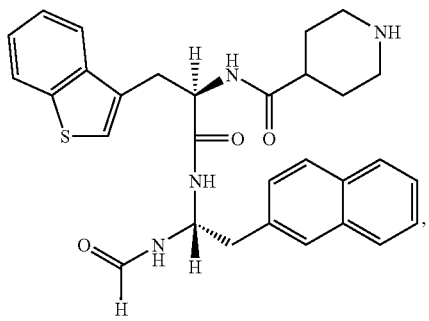
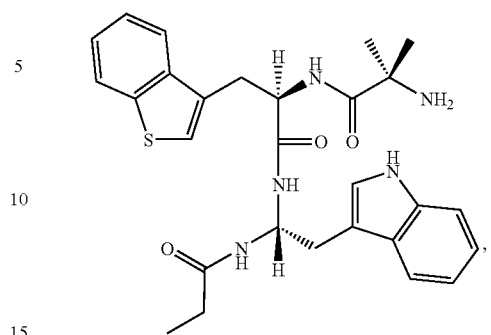
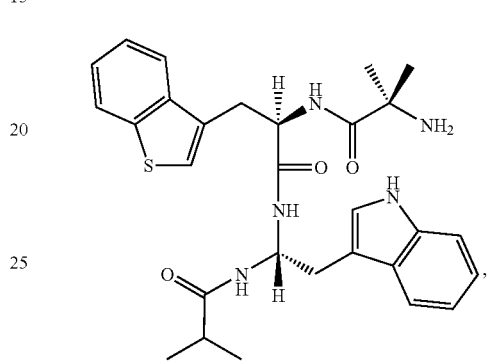
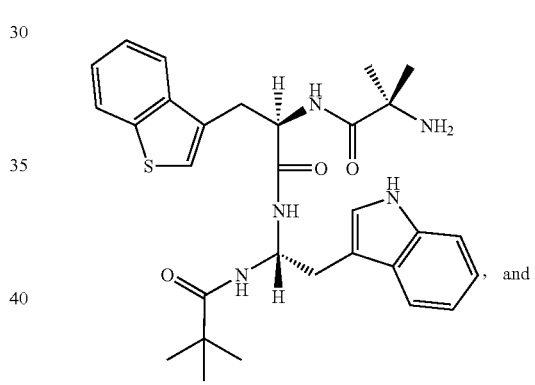
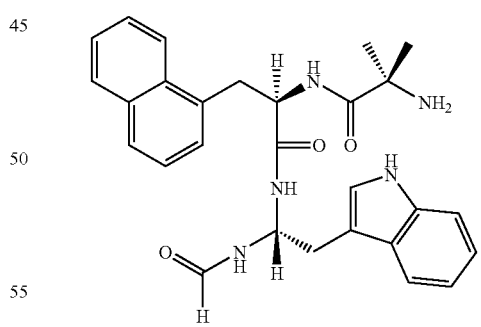
or a pharmaceutically acceptable salt thereof.
A pharmaceutical composition containing a compound of the immediately foregoing group of compounds with a pharmaceutically acceptable carrier is preferred.
A preferred compound of Group 9A is a compound of Group 9B, according to the formula:

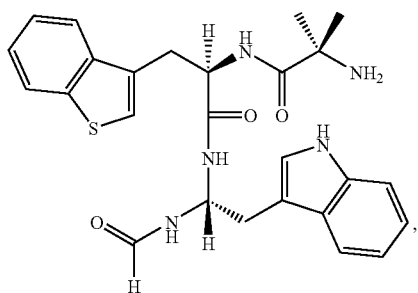
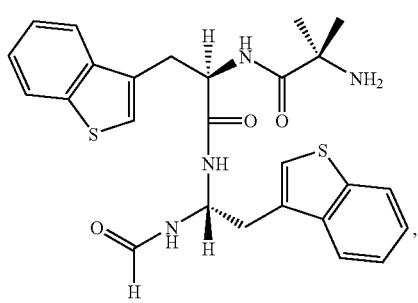
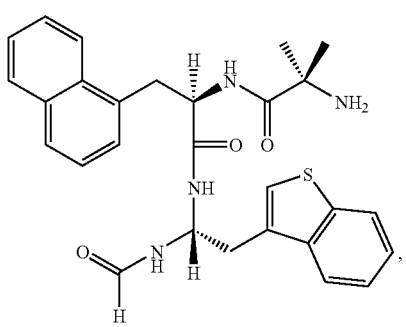
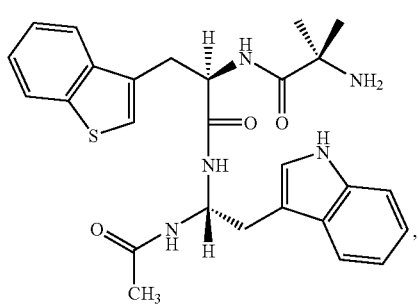
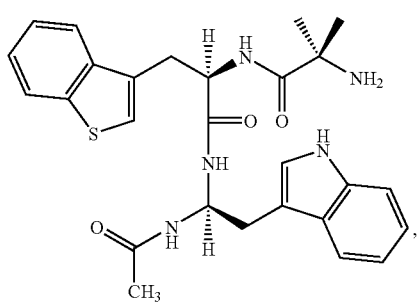
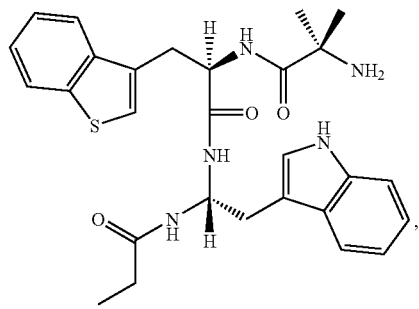
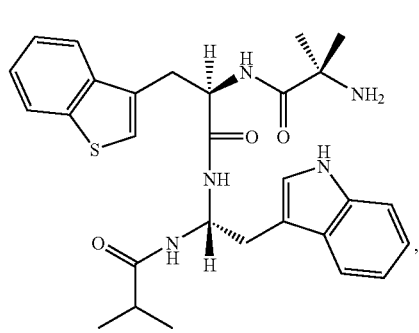
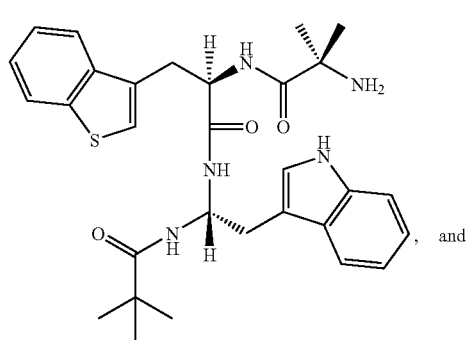
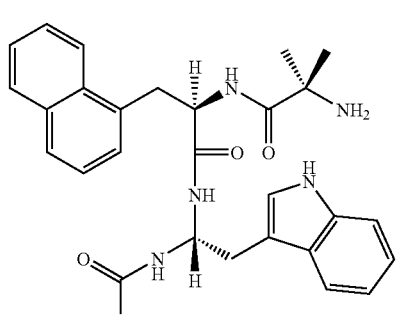
or a pharmaceutically acceptable salt thereof.
A pharmaceutical composition containing a compound of the immediately foregoing group of compounds with a pharmaceutically acceptable carrier is preferred.
A preferred compound of Group 9A is a compound of Group 9C, according to the formula:

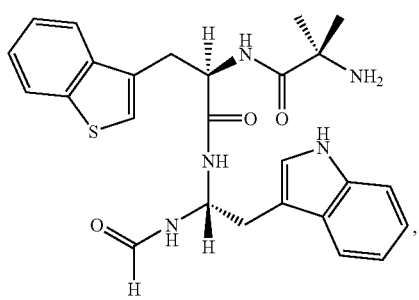

,

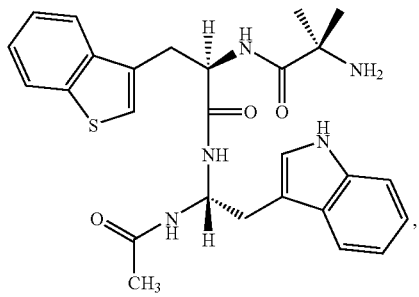

,

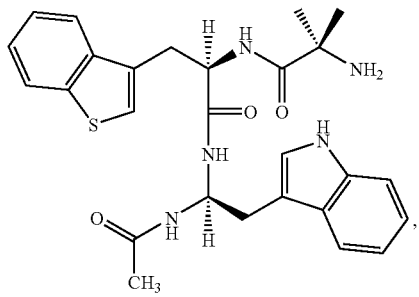

,

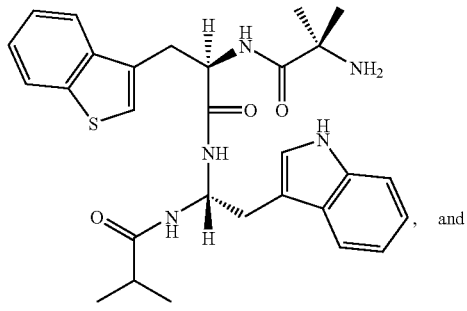

, and

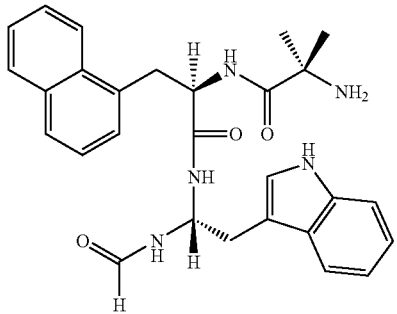

or a pharmaceutically acceptable salt thereof.

A pharmaceutical composition containing a compound of the immediately foregoing group of compounds with a pharmaceutically acceptable carrier is preferred.

A preferred compound of Group 9A is a compound of Group 9D, according to the formula:

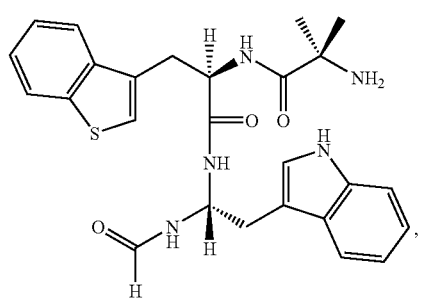

,

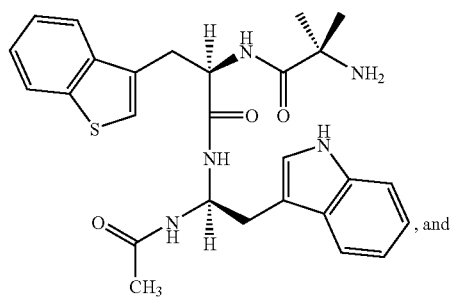

, and

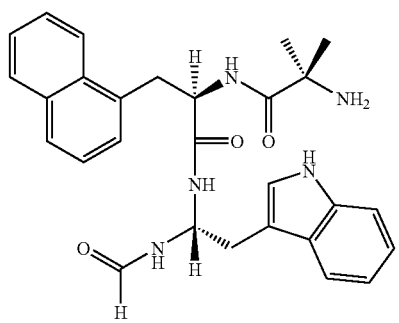

or a pharmaceutically acceptable salt thereof.

A pharmaceutical composition containing a compound of the immediately foregoing group of compounds with a pharmaceutically acceptable carrier is preferred.

A preferred compound of Group 9D is a compound of Group 9E, according to the formula:

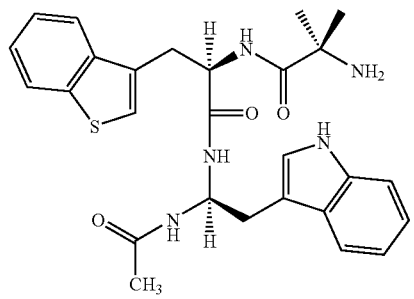

or a pharmaceutically acceptable salt thereof.

A pharmaceutical composition containing a compound of the immediately foregoing group of compounds with a pharmaceutically acceptable carrier is preferred.

A preferred compound of Group 9 is a compound of Group 9F, according to the formula:

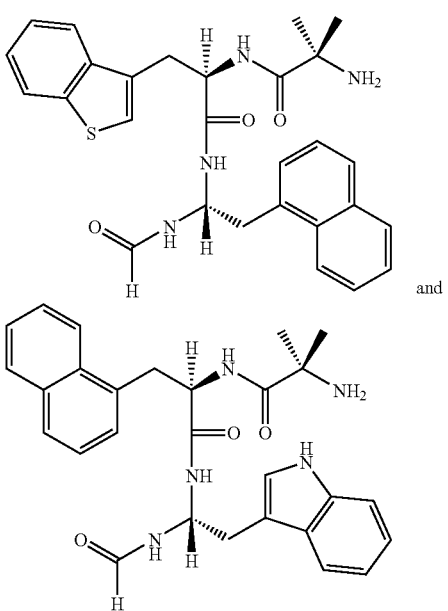

and

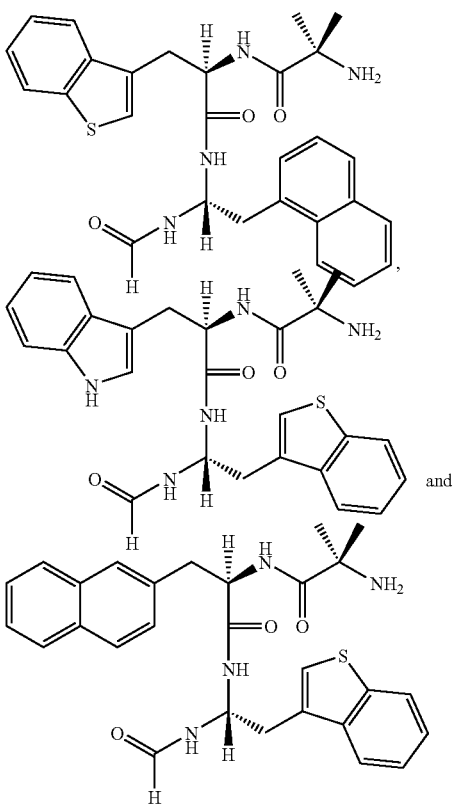

or a pharmaceutically acceptable salt thereof.

A pharmaceutical composition containing a compound of the immediately foregoing group of compounds with a pharmaceutically acceptable carrier is preferred.

A preferred compound of Group 9 is a compound of Group 9G, according to the formula:

or a pharmaceutically acceptable salt thereof.

A pharmaceutical composition containing a compound of the immediately foregoing group of compounds with a pharmaceutically acceptable carrier is preferred.

In a second aspect, the present invention features a compound according to formula (II):

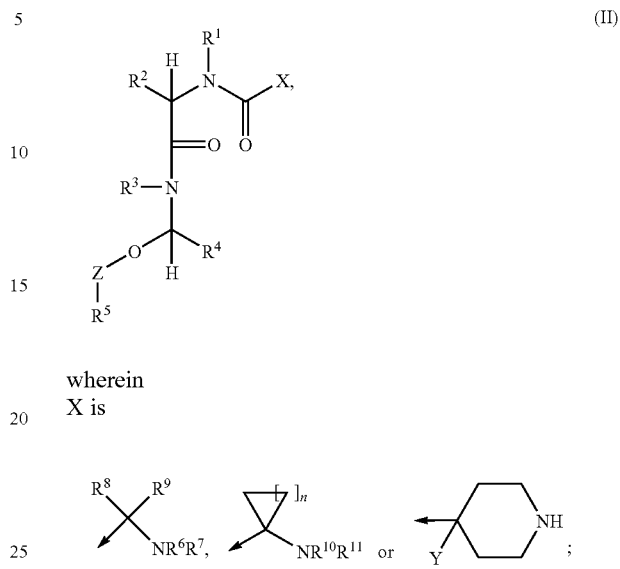

(II)

wherein
X is

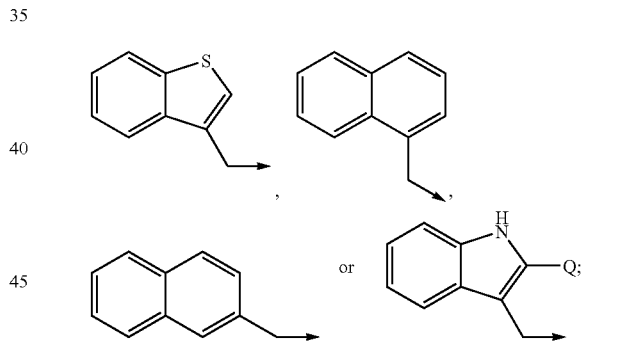

Y is H or $NR^{12}R^{13}$;
Z is —C(O)— or —SO$_2$—;
n is, independently for each occurrence. 1, 2, 3, 4, 5, 6, 7 or 8;
$R^1$ and $R^3$ each is, independently for each occurrence, H or $(C_1$-$C_4)$alkyl;
$R^2$ and $R^4$ each is, independently for each occurrence, $R^5$ is H or $(C_1$-$C_6)$alkylhalo,
$R^8$ and $R^9$ each is, independently for each occurrence, $(C_1$-$C_6)$alkyl or substituted $(C_1$-$C_6)$alkyl;
$R^6$, $R^7$, $R^{10}$, $R^{11}$, $R^{12}$ and $R^{13}$ each is, independently for each occurrence, H, $(C_1$-$C_6)$alkyl or substituted $(C_1$-$C_6)$alkyl; and
Q is H or $(C_1$-$C_4)$alkyl;
provided that both $R^2$ and $R^4$ are not

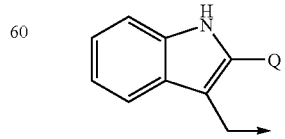

in the same compound; or a pharmaceutically acceptable salt thereof.

A preferred compound of formula (II), or a pharmaceutically acceptable salt thereof, termed a Group 10 compound, is a compound according to formula (II) wherein:

R² is

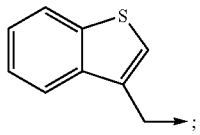

R⁴ is

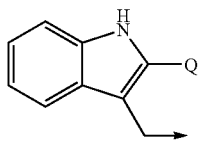

wherein Q is H;
Z is —C(O)—;
X is

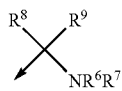

wherein R⁶ and R⁷ each is, independently, H and R⁸ and R⁹ each is, independently, CH₃; or
X is

wherein Y is H; or
X is

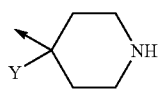

wherein Y is NR¹²R¹³ and both R¹² and R¹³ each is, independently, H;
R¹ is H;
R³ is H or methyl; and
R⁵ is H, methyl, ethyl, isopropyl or t-butyl.

A more preferred compound of Group 10 termed Group 10A is:

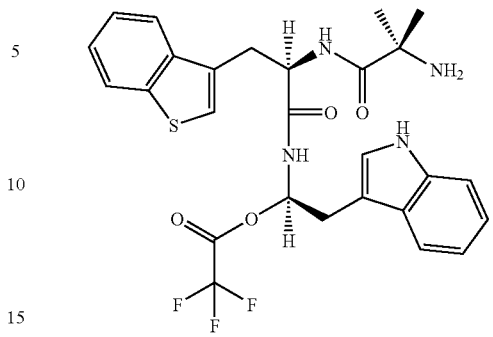

or a pharmaceutically acceptable salt thereof.

A pharmaceutical composition containing a compound of the immediately foregoing group of compounds with a pharmaceutically acceptable carrier is preferred.

Compounds of the invention are active at the GHS receptor. The compounds can bind to the receptor, and preferably, stimulate receptor activity, thus a compound of the invention is useful as a functional ghrelin analog both as a research cool and/or as a therapeutic agent. Research tool applications generally involve the use of a compound of the invention and the presence of a GHS receptor or fragment thereof. The GHS receptor can be present in different environments such as a mammalian subject, a whole cell or a cell membrane fragment. Examples of research cool applications include screening for compounds active at the GHS receptor, determining the presence of the GHS receptor in a sample or preparation and examining the role or effect of ghrelin.

One aspect the invention features a method of determining a compound's ability to bind to a GHS receptor, said method comprising the step of measuring the ability of a compound to effect binding of a compound according to formula (I) or (II) or according to any one of Groups 1, 1A, 2, 2A, 3, 3A, 4, 4A, 5, 5A, 6, 6A, 7, 7A, 8, 8A, 9, 9A, 9B, 9C, 9D, 9E, 9F, 9G, 10 and 10A to said receptor, to a fragment of said receptor, to a polypeptide comprising said fragment of said receptor or to a derivative of said polypeptide.

Another aspect of the present invention features a method of screening for ghrelin agonists and/or for ghrelin antagonists. Screening for ghrelin agonists can be performed, for example, by using a compound according to formula (I) or (II) or according to any one of Groups 1, 1A, 2, 2A, 3, 3A, 4, 4A, 5, 5A, 6, 6A, 7, 7A, 8, 8A, 9, 9A, 9B, 9C, 9D, 9E, 9F, 9G, 10 and 10A, or a pharmaceutically acceptable salt thereof, in a competition experiment with test compounds. Screening for ghrelin antagonists can be performed, for example, by using a compound according to formula (I) or (II) or according to any one of Groups 1, 1A, 2, 2A, 3, 3A, 4, 4A, 5, 5A, 6, 6A, 7, 7A, 8, 8A, 9, 9A, 9B, 9C, 9D, 9E, 9F, 9G, 10 and 10A, or a pharmaceutically acceptable salt thereof, to produce GHS receptor activity and then measuring the ability of a test compound to alter GHS receptor activity.

Ghrelin agonists can be used to achieve a beneficial effect in a subject. For example, ghrelin induces growth hormone release from primary-culture pituitary cells in a dose-dependent manner without stimulating the release of the other pituitary hormones. Injected intravenously into anaesthetized rats, ghrelin stimulated pulsatile release of growth hormone (Kojima et al., Nature, (1999), 402:656-60). In one aspect, the invention features a method for achieving a beneficial effect in a subject comprising of administering to said subject an effective amount of a compound according to formula (I) or (II) or according to any one of Groups 1, 1A, 2, 2A, 3, 3A, 4, 4A, 5, 5A, 6, 6A, 7, 7A, 8, 8A, 9, 9A, 9B, 9C, 9D, 9E, 9F, 9G, 10 and 10A, or a pharmaceutically acceptable salt thereof, wherein said amount is effective for producing a beneficial effect in helping to treat or helping to prevent a disease, ailment or condition. What is meant by "in helping to treat" is to either cure the specified disease or disorder or to reduce the severity of the symptoms of the specified disease or disorder. What is meant by "in helping to prevent" is to either reduce the likelihood of the onset specified disease or disorder or to reduce the severity of the specified disease or disorder.

In another aspect the invention features a method for stimulating growth hormone secretion in a subject in need of such stimulation, comprising the step of administering to a subject an effective amount of a ghrelin agonist according to formula (I) or (II) or according to any one of Groups 1, 1A, 2, 2A, 3, 3A, 4, 4A, 5, 5A, 6, 6A, 7, 7A, 8, 8A, 9, 9A, 9B, 9C, 9D, 9E, 9F, 9G, 10 and 10A, or a pharmaceutically acceptable salt thereof, wherein said effective amount is at least an amount sufficient to produce a detectable increase in growth hormone secretion and, preferably, is an amount sufficient to achieve a beneficial effect in a patient.

In one embodiment of the immediately foregoing aspect, said stimulation of growth hormone secretion is indicated for treating a growth hormone deficient state. A non-exclusive list of examples wherein such a beneficial effect may be indicated would include: treating a growth hormone deficient state, increasing muscle mass and/or bone density, overcoming sexual dysfunction, facilitating a weight gain, maintaining an ideal body weight, sustaining physical functioning, recovering physical function and/or increasing a diminished appetite. Gaining weight, maintaining a certain weight and/or increasing appetite are particularly useful for a subject having a disease or disorder or undergoing a medicinal treatment which is accompanied by weight loss. More preferably, said diseases or disorders accompanied by weight loss include, but are not limited to, anorexia, bulimia, cachexia, AIDS wasting and/or wasting in frail elderly. Also preferably, said medicinal treatments accompanied by weight loss include, but are not limited to, chemotherapy, radiation therapy, immobilization (i.e., mandatory bed rest) and/or dialysis.

Ghrelin antagonists can also be used to achieve a beneficial effect in a patient. In another aspect, the invention features a method for suppressing growth hormone secretion in a subject in need of such suppression, comprising the step of administering to a subject an effective amount of a ghrelin antagonist according to formula (I) or (II) or according to any one of Groups 1, 1A, 2, 2A, 3, 3A, 4, 4A, 5, 5A, 6, 6A, 7, 7A, 8, 8A, 9, 9A, 9B, 9C, 9D, 9E, 9F, 9G, 10 and 10A, or a pharmaceutically acceptable salt thereof, wherein said effective amount is at least an amount sufficient to produce a detectable decrease in growth hormone secretion and, preferably, is an amount sufficient to achieve a beneficial effect in a patient.

In one embodiment of the immediately foregoing aspect, said suppression of growth hormone secretion is indicated for the treatment of a disease or condition characterized by excessive growth hormone secretion, for the facilitation of weight loss, for the lessening of an abnormal appetite, for the maintenance of a desired weight, for the treatment of obesity, for the management of a diabetic state including complications thereof such as retinopathy, and/or for the prevention of cardiovascular disorders.

In a preferred embodiment of the immediately foregoing aspect, said excessive weight is a contributing factor to a disease or condition including, but not limited to, obesity, hypertension, diabetes dyslipidemia, cardiovascular disease, gall stones, osteoarthritis, Prader-Willi Syndrome, arthritis and certain cancers. More preferably, said facilitation of weight loss reduces the likelihood of such diseases or conditions. Also more preferably, said facilitation of weight loss comprises at least part of a treatment for such diseases or conditions.

In yet a further more preferred embodiment, compounds of the invention may also be used to promote gastrointestinal motility, in a subject in need thereof, by administering to a subject suffering from such a condition, an effective amount of one or more compounds according to formula (I) or (II) or Groups 1, 1A, 2, 2A, 3, 3A, 4, 4A, 5, 5A, 6, 6A, 7, 7A, 8, 8A, 9, 9A, 9B, 9C, 9D, 9E, 9F, 9G, 10 and 10A, or a pharmaceutically acceptable salt thereof, wherein said effective amount is at least an amount sufficient to facility gastrointestinal motility, and, preferably, is an amount sufficient to achieve a beneficial effect in a patient.

In a preferred embodiment of the immediately preceding method, said decreased gastrointestinal motility is found in a subject suffering from post-operative ileus, gastroparesis, ulcerative colitis or inflammatory bowel disease, e.g. Crohn's Disease.

In another more preferred embodiment of the immediately preceding method, said gastroparesis is incidental to the onset of diabetes or a chronic diabetic state.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

The present invention features peptidyl analogs active at the GHS receptor. The analogs of the invention can bind to the GHS receptor and, preferably, bring about signal transduction.

The nomenclature used to define the peptides is that typically used in the art wherein the amino group at the N-terminus appears to the left and the carboxyl group at the C-terminus appears to the right, i.e., stand for the structure of —NH—C(R)(R')—CO—, wherein R and R' each is, independently, hydrogen or the side chain of an amino acid (e.g., R=CH$_3$ and R'=H for Ala), or R and R' may be joined to form a ring system. Where the amino acid has isomeric forms, it is the L form of the amino acid that is represented unless otherwise explicitly indicated. Unless defined otherwise, all technical and scientific terms used herein have the same meaning as commonly understood by one of ordinary skill in the art to which this invention belongs. All publications, patent applications, patents and other references mentioned herein are incorporated by reference.

Nomenclature And Abbreviations

| Symbol | Meaning |
| --- | --- |
| Aib | α-aminoisobutyric acid |
| D-Bal | D-3-benzothienylalanine with the structure of: |

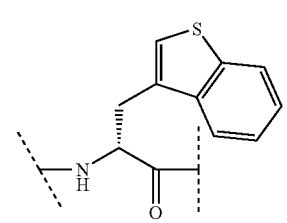

| Symbol | Meaning |
|---|---|
| DgTrp | is represented by the structure: 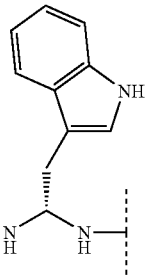 |
| DgTrp-H | is represented by the structure: 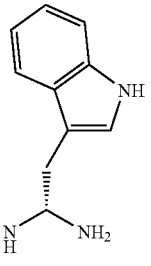 |
| DgTrp-CHO | is represented by the structure: 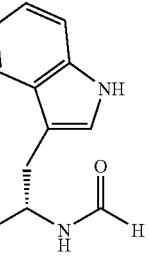 |
| DgTrp-C(O)CH₃ | is represented by the structure: 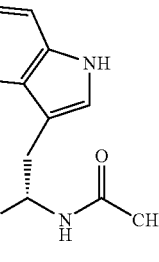 |
| DgTrp-SO₂CH₃ | is represented by the structure: 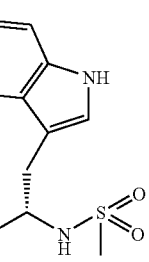 |
| D-Trp | D-tryptophan |

Certain other abbreviations used herein are defined as follows:
Ac: acetyl
AcOEt: ethyl acetate
Boc: tert-butyloxycarbonyl
BSA: bovine serum albumin
BTIB: bis(trifluoroacetoxy)iodobenzene
Bzl: benzyl
DCM: dichloromethane
DIC: N,N-diisopropylcarbodiimide
DIEA: diisopropylethyl amine
Dmab: 4-{N-(1-(4,4-dimethyl-2,6-dioxocyclohexylidene)-3-methylbutyl)-amino}benzyl
DMAP: 4-(dimethylamino)pyridine
DMF: dimethylformamide
DNP: 2,4-dinitrophenyl
EDC: 1-[3-(dimethylamino)propyl]-3-ethylcarbodiimide hydrochloride
EDTA: ethylenediaminetetraacetic acid
Fmoc: fluorenylmethyloxycarbonyl
HBTU: 2-(1H-benzotriazole-1-yl)-1,1,3,3-tetramethyluronium hexafluorophosphate
cHex: cyclohexyl
HOAT: O-(7-azabenzotriazol-1-yl)-1,1,3,3-tetramethyluronium hexafluorophosphate
HOBt: 1-hydroxy-benzotriazole
HOSu: N-hydroxysuccinimide
HPLC: high performance liquid chromatography
Mesh: morpholinoethanesulfonic acid hydrate
Mmt: 4-methoxytrityl
NMP: N-methylpyrrolidone
Pbf: 2,2,4,6,7-pentamethyldihydrobenzofuran-5-sulfonyl
tBu: tert-butyl
TIS: triisopropylsilane
TOS: tosyl
Trt: trityl
TFA: trifluoro acetic acid
TFFH: tetramethylfluoroforamidinium hexafluorophosphate
Z: benzyloxycarbonyl "Alkyl" refers to a hydrocarbon group containing one or more carbon atoms where multiple carbon atoms if present are joined by single bonds. The alkyl hydrocarbon group may be straight-chain or contain one or more branches or cyclic groups.

"Substituted alkyl" refers to an alkyl wherein one or more hydrogen atoms of the hydrocarbon group are replaced with one or more substituents selected from the group consisting of halogen, (i.e., fluorine, chlorine, bromine and iodine), —OH, —CN, —SH, —NH₂, —NHCH₃, —NO₂, —CF₃, —OCH₃, —OCF₃, —(CH₂)₀₋₄—COOH and —C₁₋₂ alkyl which itself may be optionally substituted with one or more substituents selected, independently for each occurrence, from the group consisting of halogen, (i.e., fluorine, chlorine, bromine and iodine), —OH, —CN, —SH, —NH₂, —NHCH₃, —NO₂, —CF₃, —OCH₃, —OCF₃, —(CH₂)₀₋₄—COOH. In different embodiments one to four substituents are present. The presence of —(CH₂)₀₋₄—COOH results in the production of an alkyl acid. Non-limiting examples of alkyl acids containing or consisting of —(CH₂)₀₋₄—COOH include 2-norbornane acetic acid, tert-butyric acid, 3-cyclopentyl propionic acid and the like.

"Heteroalkyl" refers to an alkyl wherein one of more of the carbon atoms in the hydrocarbon group is replaced with one or more of the following groups: amino, amido, —O— or carbonyl. In different embodiments, one or more heteroatoms are present.

"Substituted heteroalkyl" refers to a heteroalkyl wherein one or more hydrogen atoms of the hydrocarbon group are replaced with one or more substituents selected from the group consisting of halogen, (i.e., fluorine, chlorine, bromine and iodine), —OH, —CN, —SH, —NH$_2$, —NHCH$_3$, —NO$_2$, —CF$_3$, —OCH$_3$, —OCF$_3$, —(CH$_2$)$_{0-4}$—COOH and —C$_{1-2}$ alkyl which itself may be optionally substituted with one or more substituents selected, independently for each occurrence, from the group consisting of halogen, (i.e., fluorine, chlorine, bromine and iodine), —OH, —CN, —SH, —NH$_2$, —NHCH$_3$, —NO$_2$, —CF$_3$, —OCH$_3$, —OCF$_3$, —(CH$_2$)$_{0-4}$—COOH. In different embodiments one to four substituents are present. In different embodiments, one to four substituents are present.

"Alkenyl" refers to a hydrocarbon group made up of two or more carbons wherein one or more carbon-carbon double bonds are present. The alkenyl hydrocarbon group may be straight-chain or contain one or more branches or cyclic groups.

"Substituted alkenyl" refers to an alkenyl wherein one or more hydrogen are replaced with one or more substituents selected from the group consisting of halogen, (i.e., fluorine, chlorine, bromine and iodine), —OH, —CN, —SH, —NH$_2$, —NHCH$_3$, —NO$_2$, —CF$_3$, —OCH$_3$, —OCF$_3$, —(CH$_2$)$_{0-4}$—COOH and —C$_{1-2}$ alkyl which itself may be optionally substituted with one or more substituents selected, independently for each occurrence, from the group consisting of halogen, (i.e., fluorine, chlorine, bromine and iodine), —OH, —CN, —SH, —NH$_2$, —NHCH$_3$, —NO$_2$, —CF$_3$, —OCH$_3$, —OCF$_3$, —(CH$_2$)$_{0-4}$—COOH. In different embodiments one to four substituents are present. In different embodiments, one to four substituents are present.

"Alkynyl" refers to a hydrocarbon group made up of two or more carbons where one or more carbon-carbon triple bonds are present. The alkynyl hydrocarbon group may be straight-chain or contain one or more branches or cyclic groups.

"Substituted alkynyl" refers to an alkynyl wherein one or more hydrogen are replaced with one or more substituents selected from the group consisting of halogen, (i.e., fluorine, chlorine, bromine and iodine), —OH, —CN, —SH, —NH$_2$, —NHCH$_3$, —NO$_2$, —CF$_3$, —OCH$_3$, —OCF$_3$, —(CH$_2$)$_{0-4}$—COOH and —C$_{1-2}$ alkyl which itself may be optionally substituted with one or more substituents selected, independently for each occurrence, from the group consisting of halogen, (i.e., fluorine, chlorine, bromine and iodine), —OH, —CN, —SH, —NH$_2$, —NHCH$_3$, —NO$_2$, —CF$_3$, —OCH$_3$, —OCF$_3$, —(CH$_2$)$_{0-4}$—COOH. In different embodiments one to four substituents are present. In different embodiments one to four substituents are present.

"Aryl" refers to an optionally substituted aromatic group with at least one ring having a conjugated pi-electron system containing up to two conjugated or fused ring systems. Aryl includes, but is not limited to, carboxylic aryl, heterocyclic aryl and biaryl groups. Preferably, the aryl is a five or six-member ring. Preferred atoms for a heterocyclic aryl are one or more sulfur, oxygen and/or nitrogen. Non-limiting examples of aryl include phenyl, 1-naphthyl, 2-naphthyl, indole, quinoline, 2-imidazole and 9-anthracene and the like. Aryl substituents may be selected from the group consisting of halogen, (i.e., fluorine, chlorine, bromine and iodine), —OH, —CN, —SH, —NH$_2$, —NHCH$_3$, —NO$_2$, —CF$_3$, —OCH$_3$, —OCF$_3$, —(CH$_2$)$_{0-4}$—COOH and —C$_{1-2}$ alkyl which itself may be optionally substituted with one or more substituents selected, independently for each occurrence, from the group consisting of halogen, (i.e., fluorine, chlorine, bromine and iodine), —OH, —CN, —SH, —NH$_2$, —NHCH$_3$, —NO$_2$, —CF$_3$, —OCH$_3$, —OCF$_3$, —(CH$_2$)$_{0-4}$—COOH. In different embodiments one to four substituents are present. In different embodiments the aryl contains 0, 1, 2, 3 or 4 substituents.

"Arylalkyl" or "alkylaryl" refers to an "alkyl" joined to an "aryl".

"Acyl" refers to X'—R"—C(O)— where R" is alkyl, substituted alkyl, heteroalkyl, substituted heteroalkyl, alkenyl, substituted alkenyl, alkynyl, substituted alkynyl, aryl, alkylaryl or substituted alklyaryl and X' is H or absent.

The present invention includes diastereomers as well as their racemic and resolved enantiomerically pure forms. The claimed analogs can contain D-amino acids, L-amino acids or a combination thereof. Preferably, and unless otherwise indicated, an amino acid present in a ghrelin analog is the L-enantiomer.

EXAMPLES

Examples are provided below to further illustrate different features of the present invention. The examples also illustrate useful methodology for practicing the invention. These examples do not limit the claimed invention.

Example 1

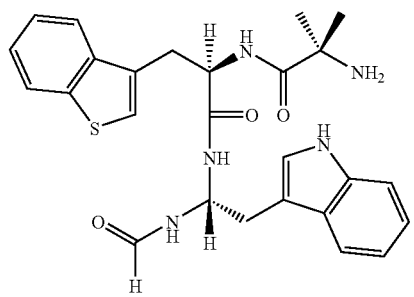

Example 2

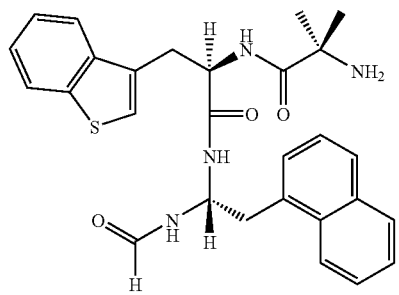

Example 3

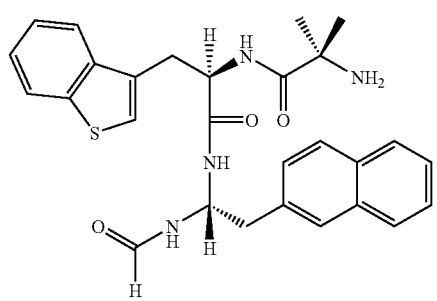

| 67 | 68 |
|---|---|
| Example 4 | Example 8 |
| 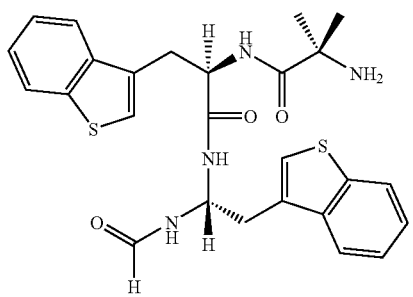 | 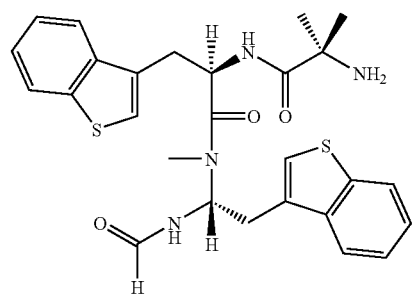 |
| Example 5 | Example 9 |
| 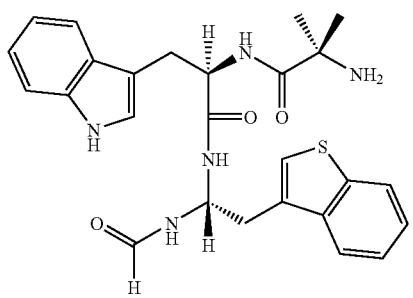 | 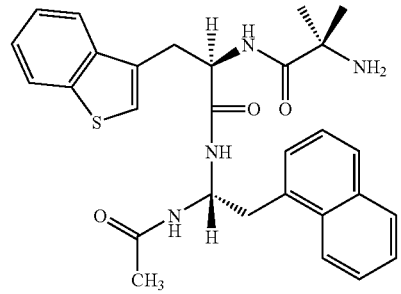 |
| Example 6 | Example 10 |
| 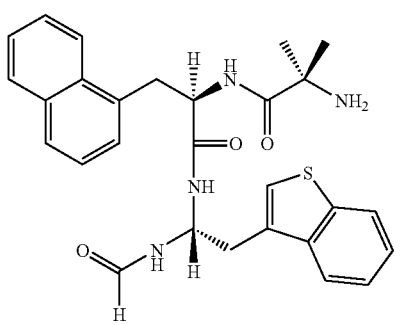 | 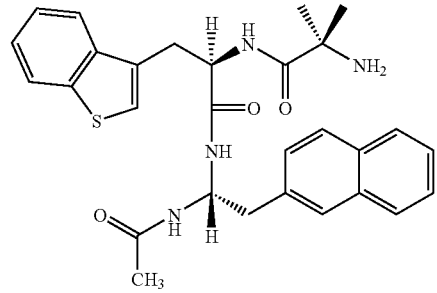 |
| Example 7 | Example 11 |
| 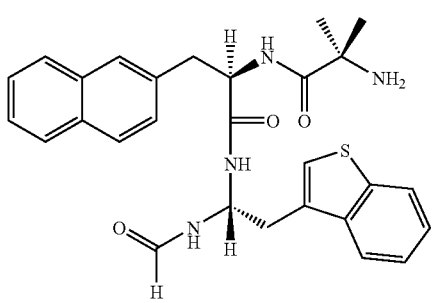 | 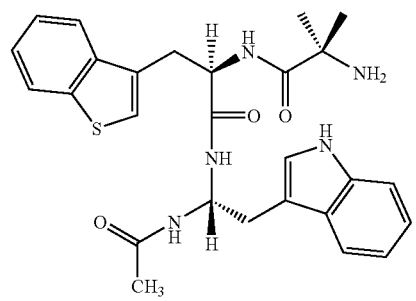 |

Example 12
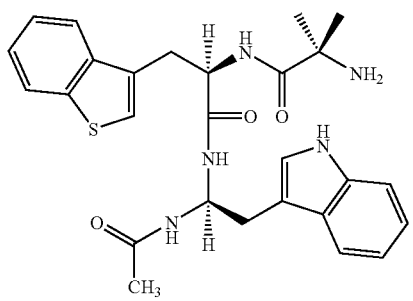
Example 13
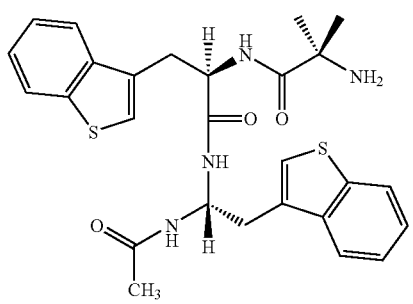
Example 14
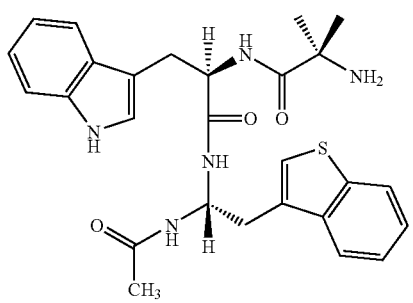
Example 15
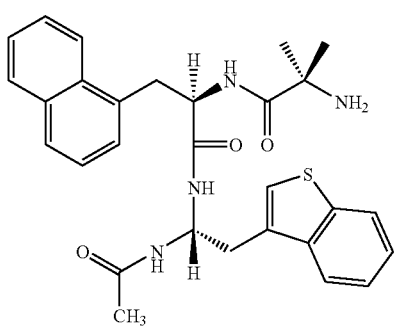
Example 16
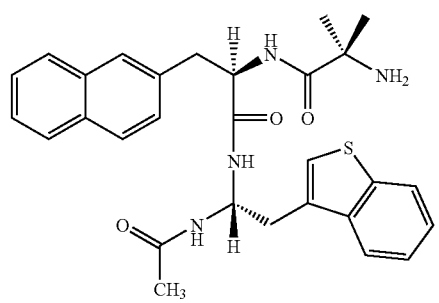
Example 17
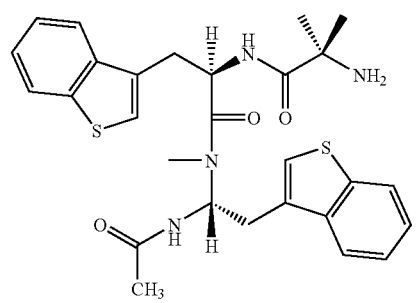
Example 18
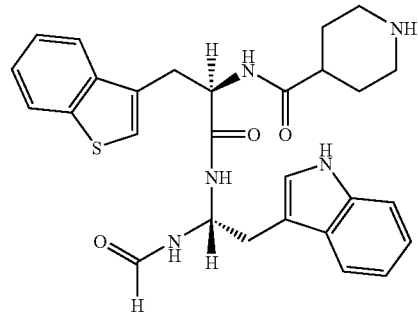
Example 19
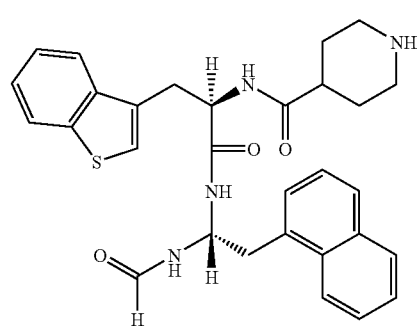

71
Example 20
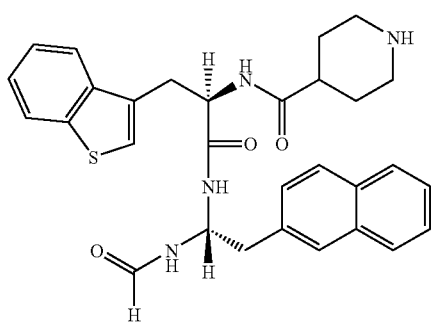
Example 21
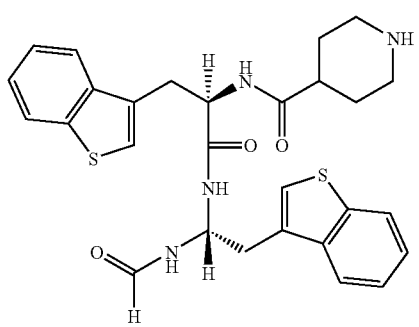
Example 22
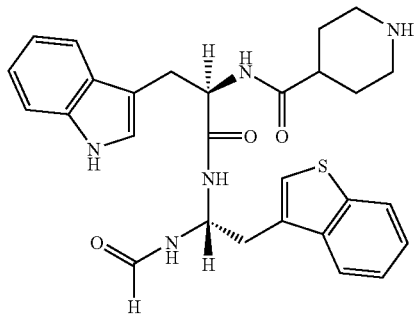
Example 23
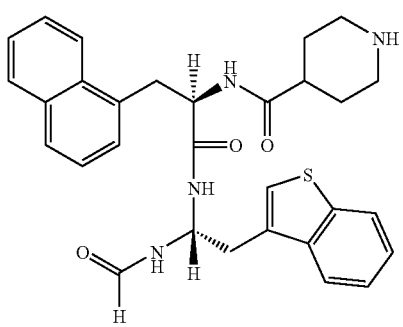
72
Example 24
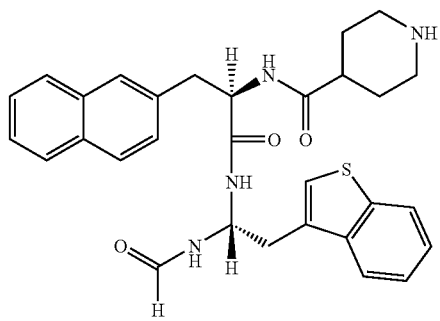
Example 25
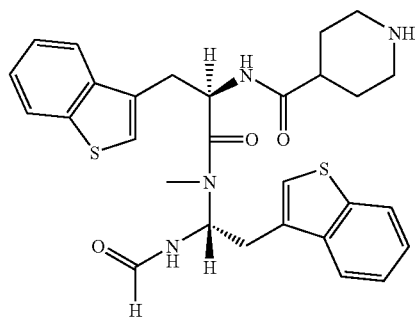
Example 26
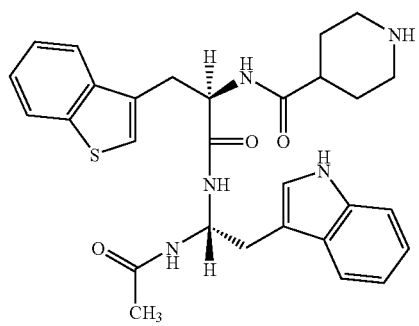
Example 27
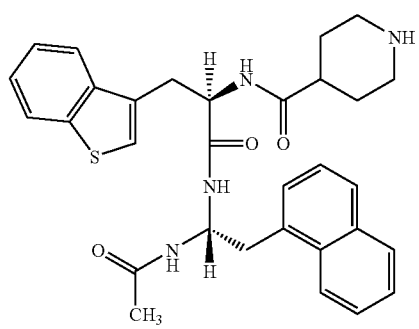

73
Example 28
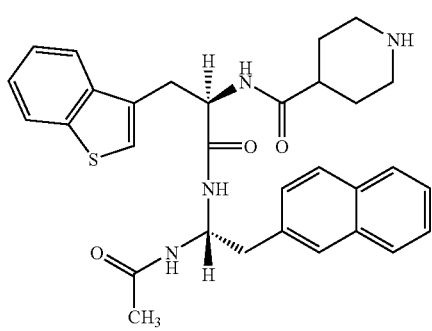
Example 29
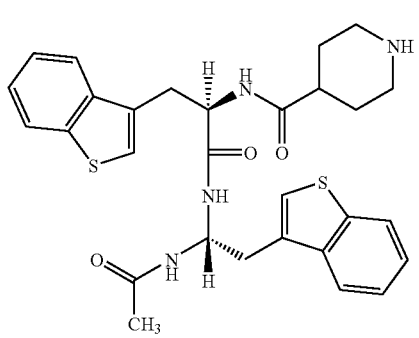
Example 30
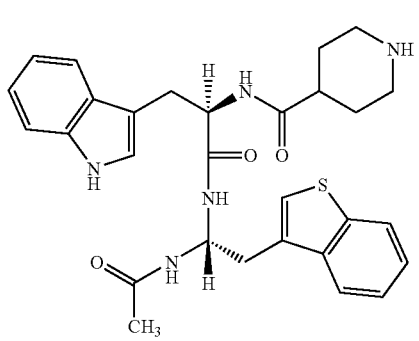
Example 31
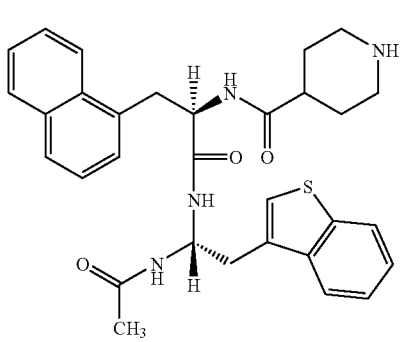
74
Example 32
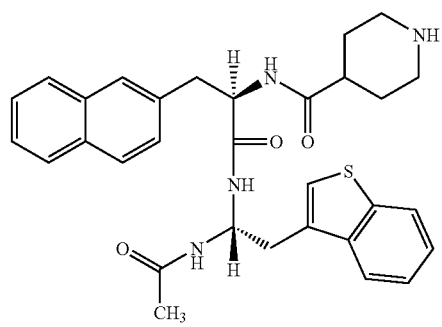
Example 33
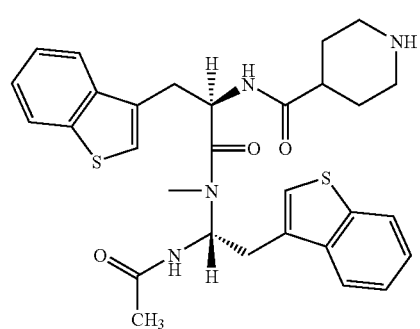
Example 34
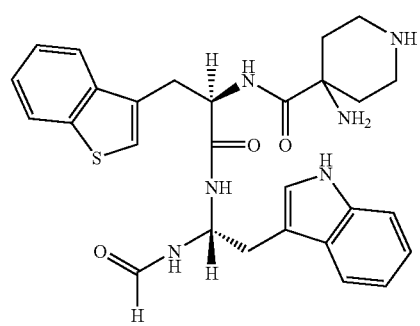
Example 35
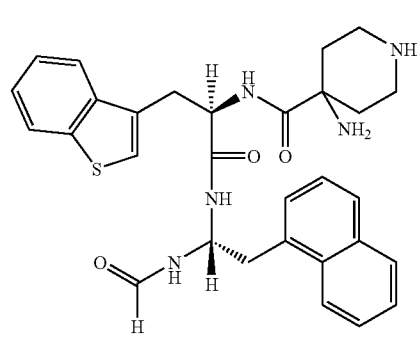

75
Example 36
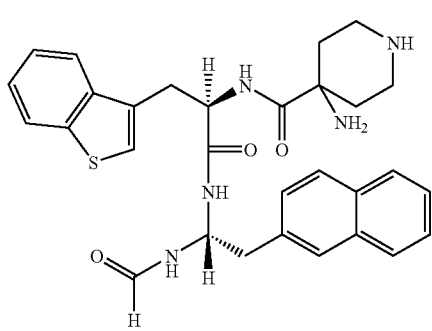
Example 37
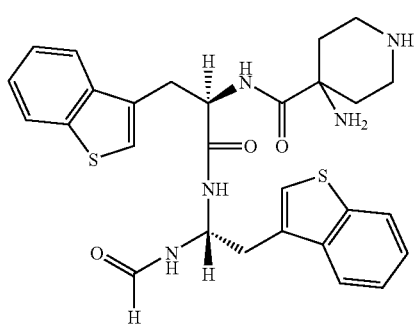
Example 38
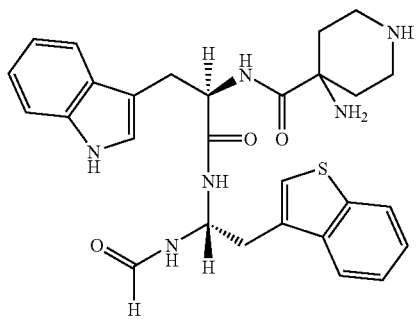
Example 39
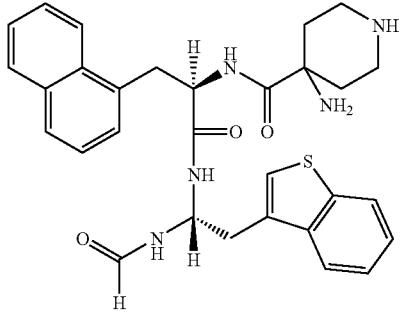
76
Example 40
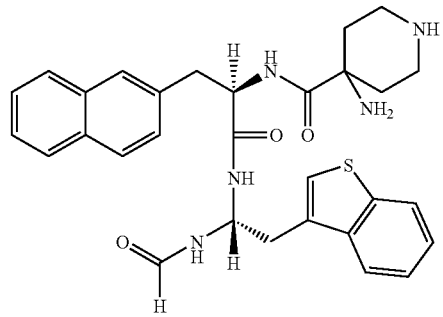
Example 41
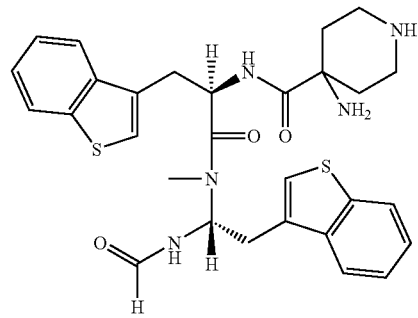
Example 42
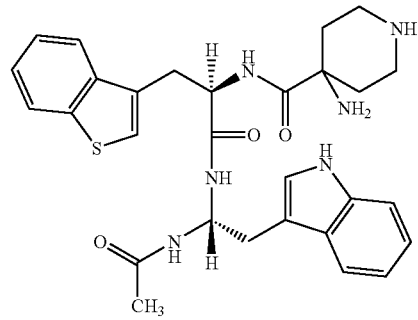
Example 43
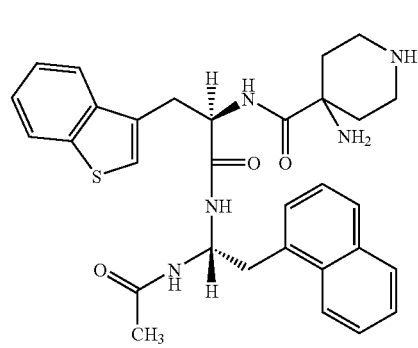

| 77 | 78 |
|---|---|
| Example 44 | Example 48 |
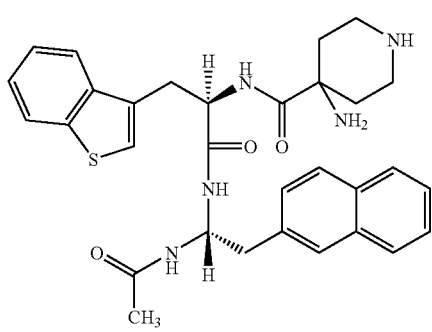
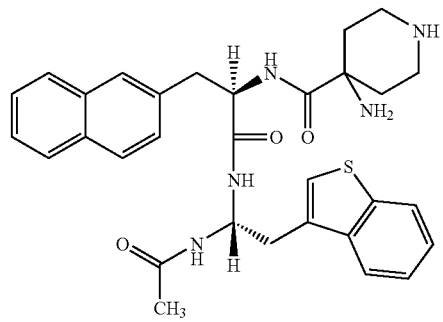
Example 45
Example 49
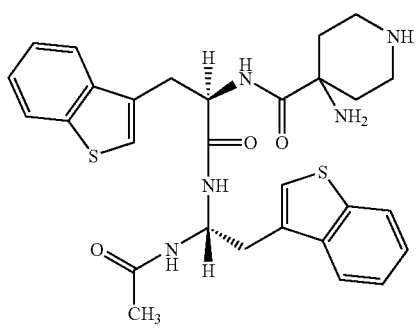
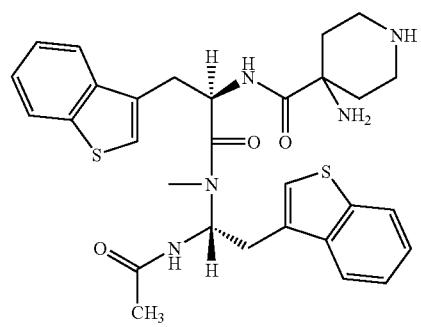
Example 46
Example 50
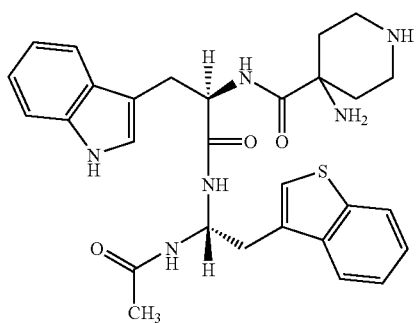
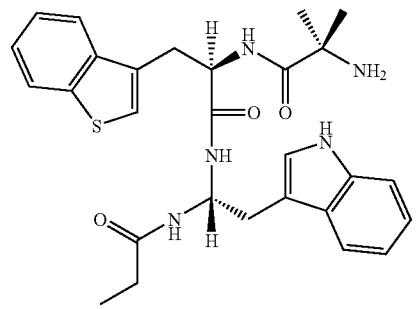
Example 47
Example 51
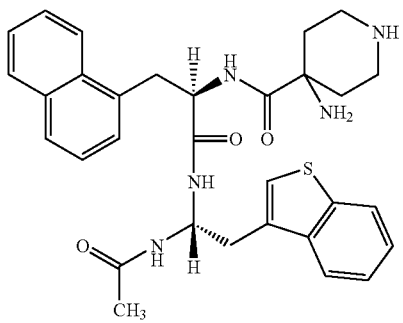
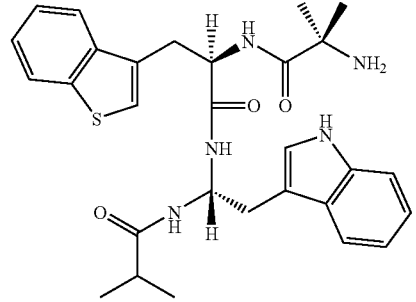

Example 52
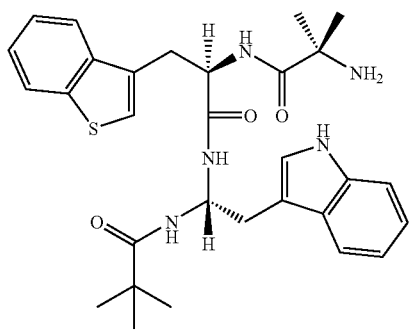
Example 53
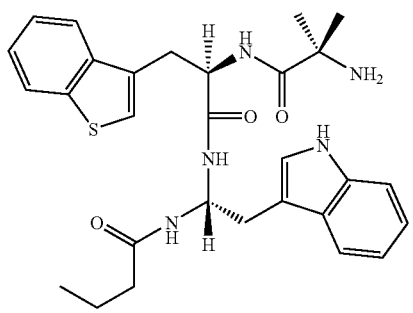
Example 54
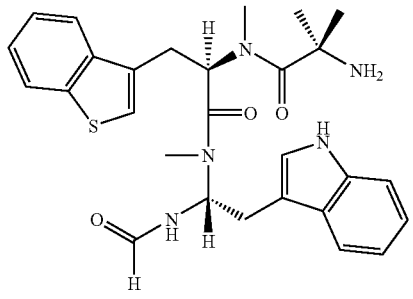
Example 55
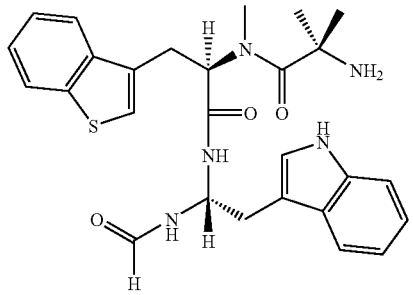
Example 56
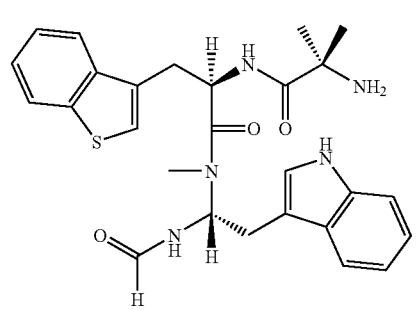
Example 57
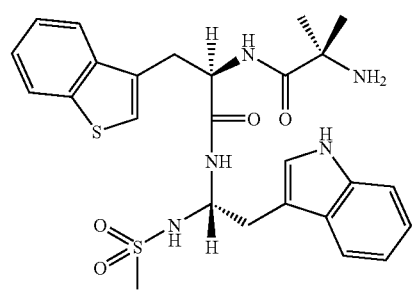
Example 58
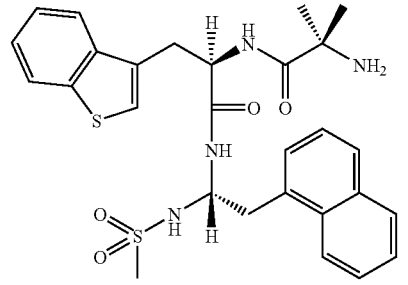
Example 59
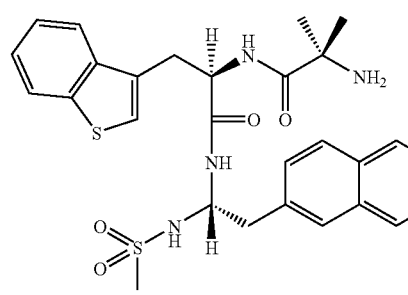

81
Example 60
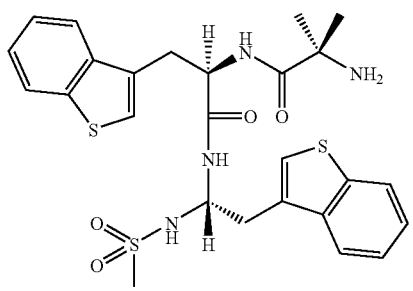
Example 61
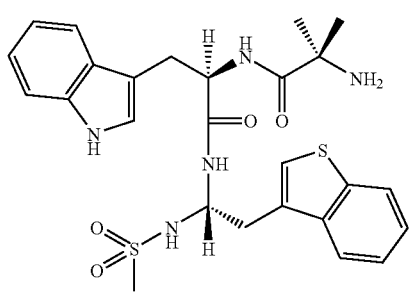
Example 62
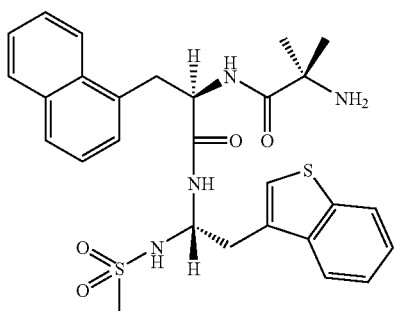
Example 63
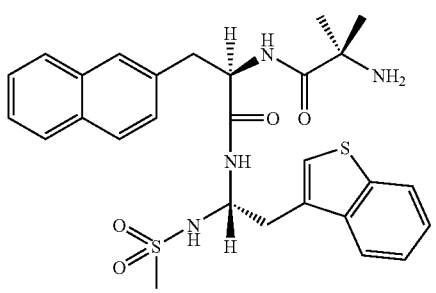
82
Example 64
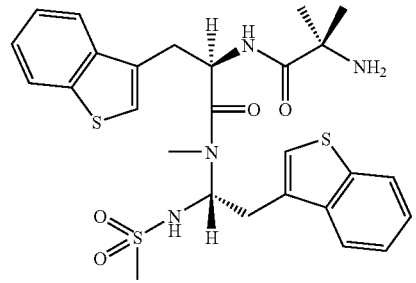
Example 65
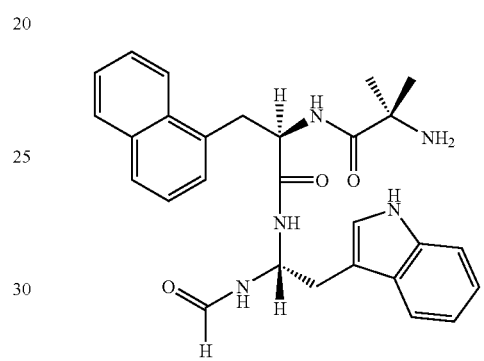
Example 66
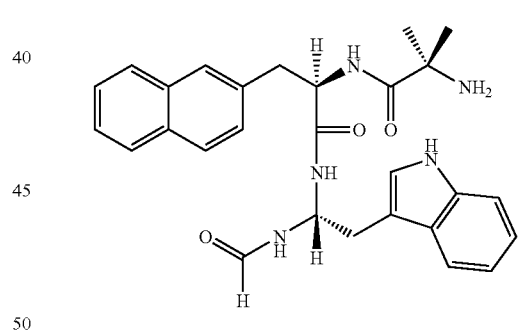
Example 67
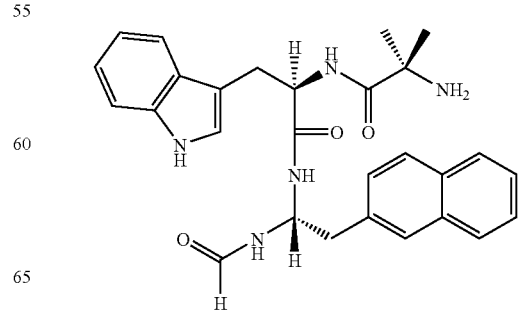

Example 68

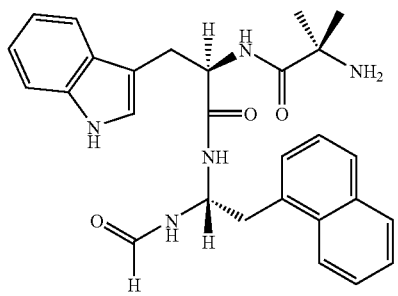

Example 69

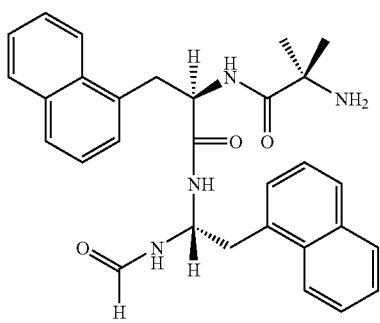

Example 70

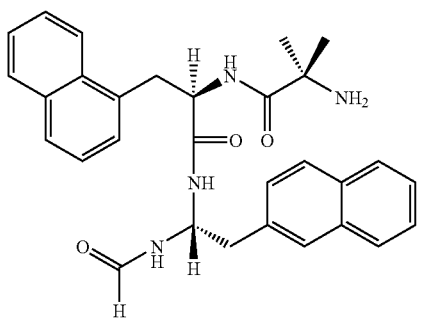

Example 71

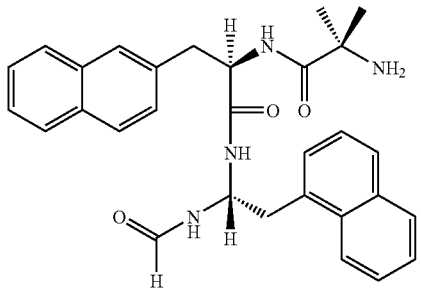

Example 72

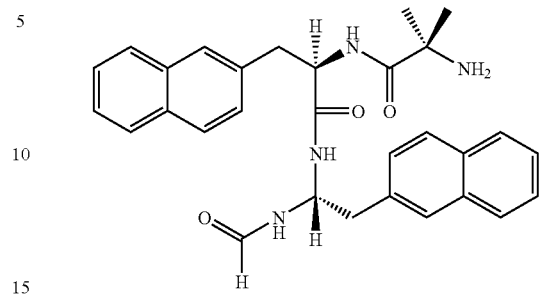

Example 73

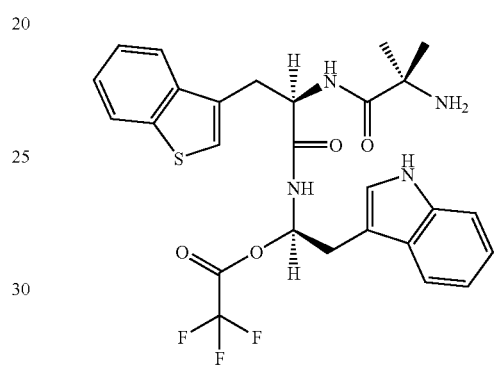

Synthesis

The compounds of the invention can be produced using the techniques disclosed in the examples herein as well as techniques that are well known in the art. For example, a polypeptide region of a GHRP analog can be chemically or biochemically synthesized and modified. Examples of techniques for biochemical synthesis involving the introduction of a nucleic acid into a cell and expression of nucleic acids are provided in Ausubel, *Current Protocols in Molecular Biology*, John Wiley, 1987-1998 and Sambrook et al., in *Molecular Cloning, A Laboratory Manual*, $2^{nd}$ Edition, Cold Spring Harbor Laboratory Press, 1989. Techniques for chemical synthesis of polypeptides are also well known in the art e.g., Vincent in *Peptide and Protein Drug Delivery*, New York, N.Y., Dekker, 1990. For example, the peptides of this invention can be prepared by standard solid phase peptide synthesis (See, e.g., Stewart, J. M., et al., Solid Phase Synthesis (Pierce Chemical Co., 2d ed. 1984)).

The substituent $R^1$ of the above formula (I) may be attached to the free amine of the N-terminal amino acid by standard methods known in the art. For example, alkyl groups, e.g., $(C_1-C_{30})$alkyl, may be attached using reductive alkylation. Hydroxyalkyl groups, e.g., $(C_1-C_{30})$hydroxyalkyl, may also be attached using reductive alkylation wherein the free hydroxy group is protected with a t-butyl ester. Acyl groups, e.g., $COE^1$, may be attached by coupling the free acid, e.g., $E^1COOH$, to the free amine of the N-terminal amino acid by mixing the completed resin with 3 molar equivalents of both the free acid and diisopropylcarbodiimide in methylene chloride for about one hour. If the free acid contains a free hydroxy group, e.g., p-hydroxyphenylpropionic acid, then the coupling should be performed with an additional 3 molar equivalents of HOBT.

Peptides of the invention also can be and were synthesized in a parallel fashion on an ACT 396 Multiple Biomolecular Synthesizer® (Advanced ChemTech®, Louisville, Ky.), (hereinafter referred to as "synthesizer"). The synthesizer was programmed to perform the following reaction cycle:
 (1) washing with dimethylformamide (DMF);
 (2) removing Fmoc protecting group with 20% piperidine in DMF once for 5 minutes and a second time for 25 minutes;
 (3) washing with DMF;
 (4) coupling with Fmoc amino acid for one hour at room temperature in the presence of diisopropylcarbodiimide (DIC) and 1-hydroxybenzotriazole (HOBt); and
 (5) repeating step 4.

Intermediate A:
N-α-Boc-Aib-D-Bal-D-Trp(Boc)-NH$_2$

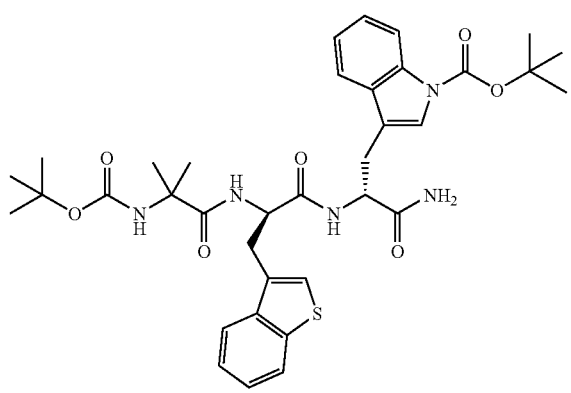

The titled compound was automatically assembled on an ACT 396 synthesized (Advanced ChemTech®, Louisville, Ky.) by using fluorenylmethyloxycarbonyl (Fmoc) chemistry. Sieber resin (50 μmol scale for each reaction well, AnaSpec®, San Jose, Calif.) with a substitution of 0.44 mmol/g was used. Boc-Aib-OH and Fmoc-D-Trp(Boc)-OH were purchased from Novabiochem® (San Diego, Calif.). Fmoc-D-Bal-OH was purchased from Chem-Impex International, Inc.® (Wood Dale, Ill.). The resin in two reaction wells was first treated with 25% piperidine solution in DMF for one half hour to remove Fmoc protecting group, then three times with 1.5 mL DMF wash. Fmoc-D-Trp(Boc)-OH (300 μmol, 6 eq.) was coupled to the resin using DIC (0.4 N solution in DMF, 300 μmol, 6 eq.) and HOBt (0.3 N solution in NMP, 300 μmol, 6 eq.) as coupling reagents and NMP as solvent. Double coupling was performed twice for one hour intervals. The resin was then washed with DMF (3×1.5 mL). The above deprotection/wash/coupling/wash cycle was repeated to add D-Bal and Boc-Aib residues by using Foci-D-Bal-OH and Boc-Aib-OH protected amino acids. The resin, after the assembly, was washed with DCM and transferred to a reaction vassal on a shaker. The resin was shaken with 1% TFA in DCM (10 mL) for ten minutes. The solution was drained into a flask containing 10% pyridine in 4 mL of Mesh. This procedure was repeated two times. The resin was then washed with Mesh and DCM. The filtrates were combined and concentrated under reduced pressure. The resulting solution was then:
 1). diluted with 50 mL DCM;
 2). washed with 20 mL saturated sodium bicarbonate aqueous solution, 20 mL of a 1 M potassium hydrogen sulfate aqueous solution, and 20 mL saturated sodium chloride aqueous solution;
 3). dried over anhydrous sodium sulfate;
 4). filtered; and
 5). evaporated to dryness under reduced pressure.

A white powder weighing 57 mg. was obtained. Electro-spray ionization mass spectrometry (ESI MS) analysis gave the molecular weight at 692.4 (in agreement with the calculated molecular weight of 691.9). The end product was determined to be 99% pure based on analytical HPLC analysis.

Intermediate B: N-α-Boc-Aib-D-Bal-DgTrp(Boc)-H

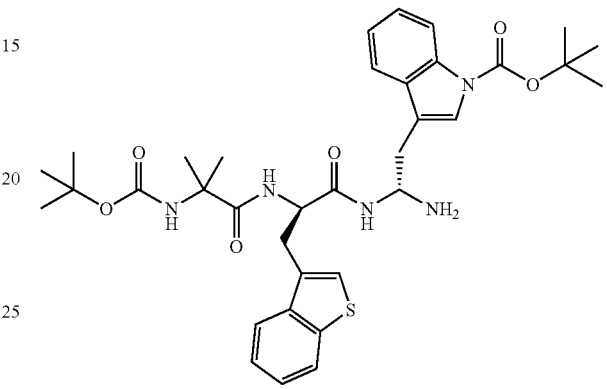

A solution of N-α-Boc-Aib-D-Bal-D-Trp(Boc)-NH$_2$ (Intermediate A, 48.9 mg, 62 μmol), pyridine (136 μmol, 2.2 eq.) and bis(trifluoroacetoxy)iodobenzene (34.4 mg, 1.1 eq.) in water and acetonitrile (1:1) was stirred at room temperature for forty-five minutes. The solvents were removed under reduced pressure. The residue was dissolved in 10 mL of AcOEt and washed three times with 2 mL of saturated NaHCO$_3$, three times with 2 mL of saturated KHSO$_4$ and three times with 2 mL brine. The organic layer was dried over Na$_2$SO$_4$, filtered and evaporated to dryness in vacuo. A yield of 47.3 mg of the desired product was obtained. ESI-MS analysis gave the molecular weight at 664.0 (in agreement with the calculated molecular weight of 663.8). The end product was determined to be 99% pure based on analytical HPLC analysis.

Intermediate C:
N-α-Boc-Aib-D-Bal-DgTrp(Boc)-CHO

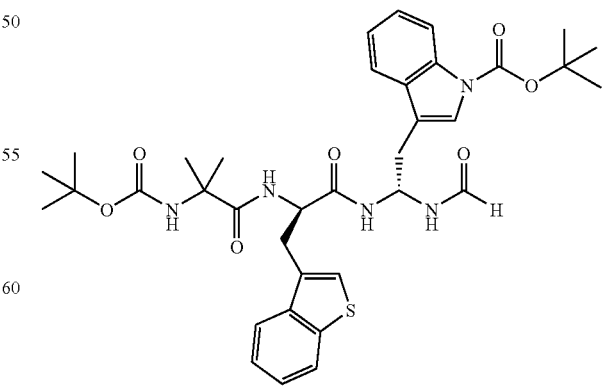

A mixture of N-α-Boc-Aib-D-Bal-DgTrp(Boc)-H (Intermediate B, 47.3 mg, 71.2 μmol), HCOOCH$_3$ (10.3 mL) and DIEA (100 μL) was heated at 50° C. overnight. The mixture was diluted with 5 mL of toluene and stripped down. The residue was dissolved in 10 mL of ethyl acetate and washed three times with 2 mL saturated KHSO₄ and three times with 2 mL brine. The organic layer was dried over Na₂SO₄, filtered and the solvent was removed in vacuo. A yield of 40.5 mg of the desired product was obtained. The end product was determined to be 99% pure based on analytical HPLC analysis. ESI-MS analysis showed the molecular weight at 692.3 (in agreement with the calculated molecular weight of 691.9).

Example 1

Aib-D-Bal-DgTrp-CHO

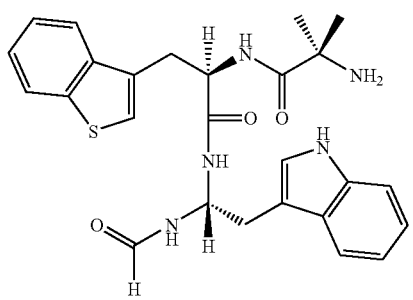

N-α-Boc-Aib-D-Bal-DgTrp(Boc)-CHO (Intermediate C, 35.5 mg, 51.3 μmol) was treated with a 5 mL of mixture of TFA/thioanisol/anisol (v/v/v: 4/0.5/0.5) at 0° C. for one and one-half hours. The solution was evaporated in vacuo. The residue was triturated with cold ether and the precipitate was collected by filtration. The crude product was purified by HPLC using Luna® column (40×130 mm) of C18-(2) (Phenomenex®, Torrance, Calif.). The column was eluted with a liner gradient from 95% A and 5% B to 60% A and 40% B in an hour, where A was 0.1% TFA in water and B was 0.1% TFA in acetonitrile. Fractions containing the product were pooled and lyophilized. A sample weighing 8.4 mg of the desired compound was obtained. The end product was determined to be 99% pure based on analytical HPLC analysis. ESI-MS analysis showed the molecular weight at 491.4 (in agreement with the calculated molecular weight of 491.6).

Example 11

Aib-D-Bal-DgTrp-C(O)CH₃

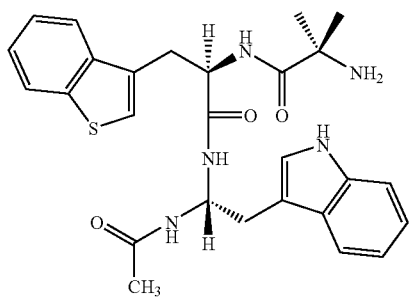

A mixture of N-α-Boc-Aib-D-Bal-DgTrp(Boc)-H (Intermediate B, 50.0 mg, 75.3 μmol), acetic acid (82.8 μmol), EDC (82.8 μmol), HOBt (82.8 μmol) and DIEA (82.8 μmol) in DCM (10 mL) was stirred at room temperature overnight. The mixture was diluted with 15 mL of DCM, washed twice with a 5% aqueous NaHCO₃ solution, twice with a 5% citric acid aqueous solution and twice with brine, dried over MgSO₄, filtered and condensed under reduced pressure, yielding N-α-Boc-Aib-D-Bal-DgTrp(Boc)-C(O)CH₃. The intermediate was used without further purification.

N-α-Boc-Aib-D-Bal-DgTrp(Boc)-C(O)CH₃ (50.0 μmol) was treated with 5 mL of mixture of TFA/thioanisol/anisol (v/v/v: 4/0.5/0.5) at 0° C. for one and one-half hours. The solution was evaporated in vacuo. The residue was triturated with cold ether and the precipitate collected by filtration. The crude product was purified by HPLC using Luna® column (40×130 mm) of C18-(2) (Phenomenex®, Torrance, Calif.). The column was eluted with a liner gradient from 95% A and 5% B to 60% A and 40% B in an hour, where A is 0.1% TFA in water and B is 0.1% TFA in acetonitrile. Fractions containing the product were pooled and lyophilized, yielding the desired compound. The end product was determined to be 99.3% pure based on analytical HPLC analysis. ESI-MS analysis showed the molecular weight at 505.5 (in agreement with the calculated molecular weight of 505.64).

Example 57

Aib-D-al-DgTrp-SO₂CH₃

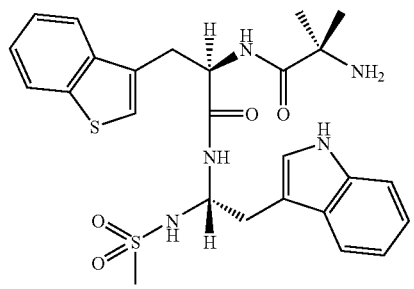

A mixture of N-α-Boc-Aib-D-Bal-DgTrp(Boc)-H (Intermediate B, 50.0 mg, 75.3 μmol), methanesulfonyl chloride (75.3 μmol) and DIEA (82.8 μmol) in 10 mL DCM is stirred at room temperature overnight. The mixture is diluted with 15 mL of DCM, washed twice with a 5% aqueous NaHCO₃ solution, twice with a 5% citric acid aqueous solution and twice with brine, dried over MgSO₄, filtered and condensed under reduced pressure, yielding N-α-Boc-Aib-D-Bal-DgTrp(Boc)-SO₂CH₃. The intermediate is used without further purification.

N-α-Boc-Aib-D-Bal-DgTrp(Boc)-SO₂CH₃ (50.0 μmol) is treated with 5 mL of mixture of TFA/thioanisol/anisol (v/v/v: 4/0.5/0.5) at 0° C. for one and one-half hours. The solution is evaporated in vacuo. The residue is triturated with cold ether and the precipitate is collected by filtration. The crude product is purified by HPLC using Luna® column (40×130 mm) of C18-(2) (Phenomenex®, Torrance, Calif.). The column is eluted with a liner gradient from 95% A and 5% B to 60% A and 40% B in an hour where A is 0.1% TFA in water and B is 0.1% TFA in acetonitrile. Fractions containing the product are pooled and lyophilized, yielding the desired compound.

Other peptides of the invention can be prepared by a person of ordinary skill in the art using synthetic procedures analogous to those disclosed generally hereinabove and/or to those disclosed specifically in the foregoing examples, as were the compounds depicted in Table 1.

TABLE 1

| Example | Structure | Molecular Weight (Calculated) | Molecular Weight (MS-ES) | Purity (%) |
|---|---|---|---|---|
| #12 | 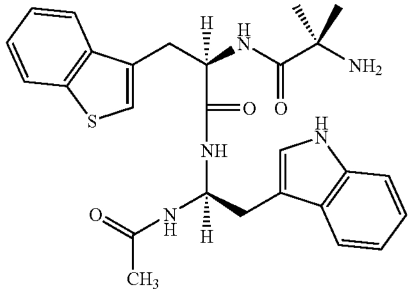 | 505.640 | 505.5000 | 97.40% |
| #1 | 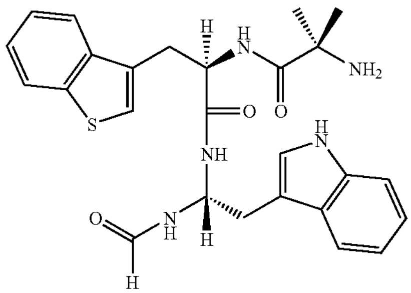 | 491.6130 | 491.4000 | 94.10% |
| #65 | 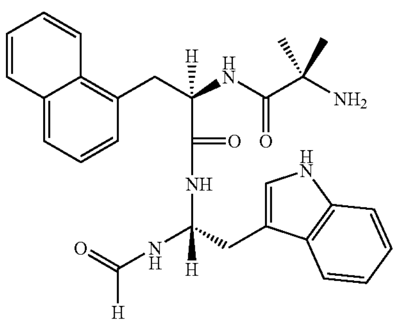 | 485.5850 | 485.6000 | 95.00% |
| #51 | 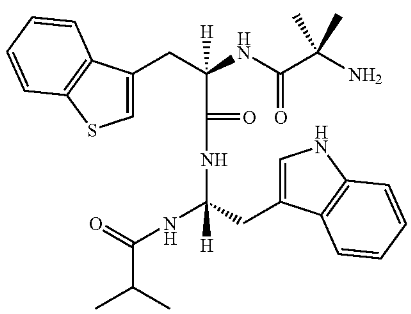 | 533.6930 | 533.6000 | 99.40% |
| #11 | 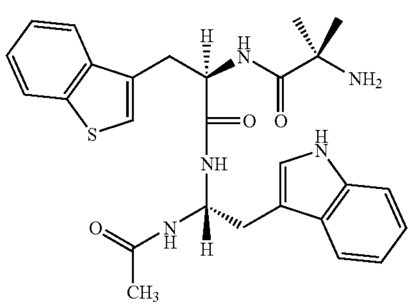 | 505.6400 | 505.5000 | 99.30% |

TABLE 1-continued

| Example | Structure | Molecular Weight (Calculated) | Molecular Weight (MS-ES) | Purity (%) |
|---|---|---|---|---|
| #50 | 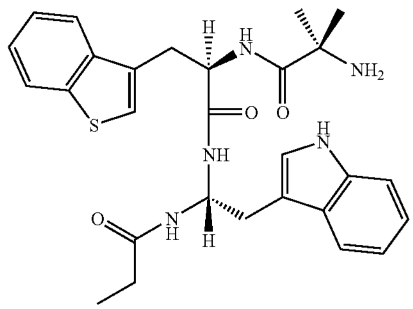 | 519.6670 | 519.3000 | 99.30% |
| #52 | 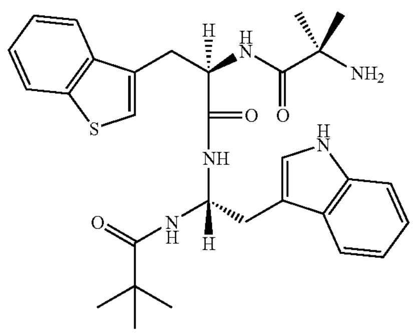 | 547.7200 | 547.5000 | 99.70% |
| #4 | 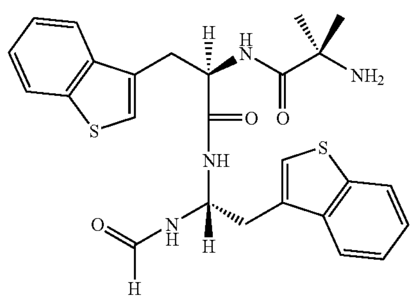 | 508.6640 | 508.2000 | 95.00% |
| #73 | 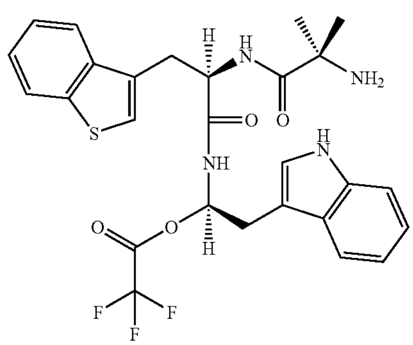 | 560.5940 | 559.5000 | 99.90% |

TABLE 1-continued

| Example | Structure | Molecular Weight (Calculated) | Molecular Weight (MS-ES) | Purity (%) |
|---------|-----------|-------------------------------|--------------------------|------------|
| #6 | 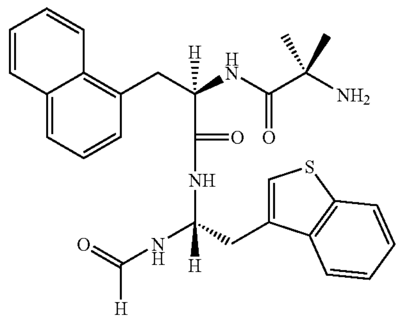 | 502.6360 | 502.3000 | 95.00% |
| #18 | 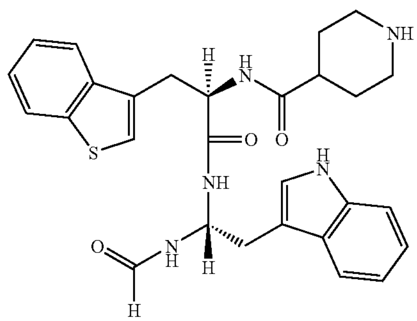 | 517.6510 | 517.3000 | 95.00% |
| #20 | 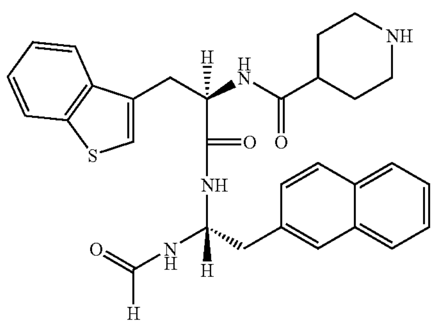 | 528.6740 | 528.6000 | 95.00% |
| #7 | 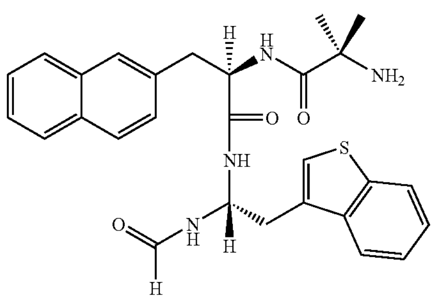 | 502.6360 | 502.3000 | 95.00% |
| #2 | 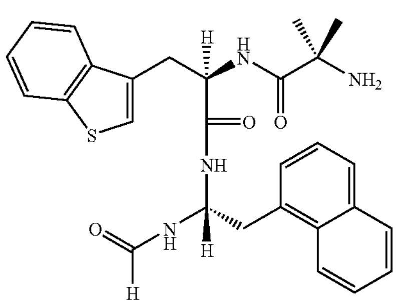 | 502.6360 | 502.2000 | 95.00% |

TABLE 1-continued

| Example | Structure | Molecular Weight (Calculated) | Molecular Weight (MS-ES) | Purity (%) |
|---------|-----------|-------------------------------|--------------------------|------------|
| #5 | 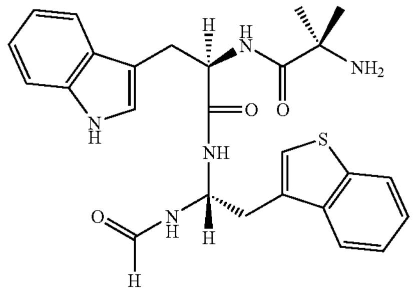 | 491.6130 | 491.6000 | 95.00% |

Biological Assays

The activities of compounds of the invention at the GHS receptor can be and were determined using techniques such as those described in the examples provided below. In different embodiments, a ghrelin analog has at least about 50%, at least about 60%, at least about 70%, at least about 80%, or at least about 90% functional activity relative to native ghrelin as determined using one or more of the functional activity assays described below and/or has an $IC_{50}$ greater than about 1,000 nM, greater than about 100 nM, or greater than about 50 nM, as determined by the receptor binding assay described below. With respect to $IC_{50}$ value, "greater" refers to potency and thus indicates a lesser amount is needed to achieve binding inhibition.

Assays measuring the ability of a compound to bind a GHS receptor employ a GHS receptor, a fragment of the receptor comprising a ghrelin binding site, a polypeptide comprising such a fragment or a derivative of the polypeptide. Preferably, the assay uses the GHS receptor or a fragment thereof. A polypeptide comprising a GHS receptor fragment that binds ghrelin can also contain one or more polypeptide regions not found in a GHS receptor. A derivative of such a polypeptide comprises a GHS receptor fragment that binds ghrelin along with one or more non-peptide components.

The GHS receptor amino acid sequence involved in binding can be readily identified using labeled ghrelin or ghrelin structural or functional analogs and different receptor fragments. Different strategies can be employed to select fragments to be tested to narrow down the binding region. Examples of such strategies include testing consecutive fragments of about fifteen amino acids in length starting at the N-terminus and testing longer length fragments. If longer length fragments are tested, a fragment binding ghrelin can be subdivided to further locate the ghrelin binding region. Fragments used for binding studies can be generated using recombinant nucleic acid techniques.

Binding assays can be performed using individual compounds or preparations containing different numbers of compounds. A preparation containing different numbers of compounds having the ability to bind to the GHS receptor can be divided into smaller groups of compounds that can be tested to identify the compound(s) binding to the GHS receptor. In an embodiment of the present invention, a test preparation containing at least ten compounds is used in a binding assay.

Binding assays can be performed using recombinantly produced GHS receptor polypeptides present in different environments. Such environments include, for example, cell extracts and purified cell extracts containing the GHS receptor polypeptide expressed from recombinant nucleic acid or naturally occurring nucleic acid; and also include, for example, the use of a purified GHS receptor polypeptide produced by recombinant means or from naturally occurring nucleic acid which is introduced into a different environment.

Screening for GHS Receptor Active Compounds

Screening for GHS receptor active compounds is facilitated using a recombinantly-expressed receptor. Using a recombinant-expressed GHS receptor offers several advantages such as the ability to express the receptor in a defined cell system so that a response to a compound at the GHS receptor can more readily be differentiated from responses at other receptors. For example, the GHS receptor can be expressed in a cell line such as HEK 293, COS 7 and CHO which normally do not express the receptor by an expression vector wherein the same cell line without the expression vector can act as a control.

Screening for compounds reducing GHS receptor activity is facilitated through the use of a ghrelin functional analog in the assay. The use of a ghrelin functional analog in a screening assay provides for GHS receptor activity. The effect of test compounds on such activity can be measured to identify, for example, allosteric modulators and antagonists.

GHS receptor activity can be measured using different techniques, such as detecting a change in the intracellular conformation of the GHS receptor, in the G-protein coupled activities, and/or in the intracellular messengers. Preferably, GHS receptor activity is measured using techniques such as those measuring intracellular $Ca^{2+}$. Examples of techniques well known in the art that can be employed to measure $Ca^{2+}$ include the use of dyes such as Fura-2® and the use of $Ca^{2+}$-bioluminescent sensitive reporter proteins such as aequorin. An example of a cell line employing aequorin to measure G-protein activity is HEK293/aeq17 (Button et al., Cell Calcium, (1993), 14:663-71 and Feighner et al., Science, (1999), 284:2184-8).

Chimeric receptors containing a ghrelin binding region functionally coupled to a different G-protein can also be used to measure GHS receptor activity. A chimeric GHS receptor contains an N-terminal extracellular domain (a transmembrane domain made up of transmembrane regions, extracellular loop regions and intracellular loop regions) and an intracellular carboxy terminus. Techniques for producing chimeric receptors and measuring G-protein coupled responses are provided in, for example, International Patent Publication No. WO 97/05252 and U.S. Pat. No. 5,264,565, both of which are hereby incorporated by reference herein.

Stimulation of GHS Receptor Activity

Structural and/or functional analogs of ghrelin can be used to stimulate GHS receptor activity. Such stimulation can be used, for example, to study the effect of GHS receptor modulation, to study the effect of growth hormone secretion, to look for or study ghrelin antagonists or to achieve a beneficial effect in a subject. Beneficial effects that can be achieved include one or more of the following: treating a growth hormone deficient state, increasing muscle mass and/or bone density, overcoming sexual dysfunction, facilitating a weight gain, achieving an ideal weight, recovering and/or maintaining normal physical functioning and/or increasing a diminished appetite.

Increasing weight and/or appetite can be useful for achieving and/or maintaining and ideal body weight, causing a weight gain or an increase in appetite gain in either an under weight subject or in a patient suffering from a disease and/or condition and/or undergoing a medicinal treatment that effects weight or appetite. In addition, for example, farm animals such as pigs, cows and chickens can be treated to gain weight. Underweight subjects include those having a body weight about 10% or less, 20% or less, or 30% or less, than the lower end of a "normal" height range or Body Mass Index ("BMI"). BMI measures a subject's height/weight ratio and is determined by calculating weight in kilograms divided by the square of height in meters determined by calculating weight in kilograms divided by the square of height in meters. The BMI "normal" range for humans is generally considered to be 19-22. "Normal" weight ranges are well known in the art and take into account factors such as a subject age, height and/or body type.

Biological Assays—Examples

1. Receptor Binding Assay

A. Preparation of CHO-K1 cells expressing the human recombinant GHS receptor-1a

The cDNA for human growth hormone secretagogue receptor-1a (hGHS-R1a) was cloned by Polymerase Chain Reaction (PCR) using human brain RNA as a template (Clontech®, Palo Alto, Calif.), gene specific primers flanking the full-length coding sequence of hGHS-R1a, (S: 5'-ATGTGGAACGCGACGCCCAGCGAAGAG-3' and AS: 5'-TCATGTATTAATACTAGATTCTGTCCA-3'), and an Advantage 2 PCR Kit® (Clontech®). The PCR product was cloned into the pCR2.1 vector using an Original TA Cloning Kit® (Invitrogen®, Carlsbad, Calif.). The full length hGHS-R1a was subcloned into the mammalian expression vector pcDNA 3.1 (Invitrogen®, Carlsbad, Calif.). The plasmid was transfected into the Chinese hamster ovary cell line, CHO-K1 (American Type Culture Collection®, Rockville, Md.), by calcium phosphate method (Wigler, M et al., Cell, (1977), 11:223). Single cell clones stably expressing the hGHS-R1a were obtained by selecting transfected cells grown in cloning rings in RPMI 1640 media supplemented with 10% fetal bovine serum and 1 mM sodium pyruvate containing 0.8 mg/ml G418 (Gibco®, Grand Island, N.Y.).

B. hGHS-R1a Binding Assay:

Membranes for radioligand binding studies can be and were prepared by homogenization of the foregoing CHO-K1 cells expressing the hGHS-R1a in 20 ml of ice-cold 50 mM Tris-HCl with a Brinkman Polytron® (Westbury, N.Y.) (setting 6, 15 sec). The homogenates were washed twice by centrifugation (39,000 g/10 min) and the final pellets were re-suspended in 50 mM Tris-HCl containing 2.5 mM $MgCl_2$ and 0.1% BSA. For the assay, aliquots (0.4 ml) were incubated with 0.05 nM ($^{125}$I)ghrelin (~2000 Ci/mmol)(Perkin Elmer Life Sciences®, Boston, Mass.) with and without 0.05 ml of unlabeled competing test compounds of the invention. After a sixty minute incubation at 4° C., the bound ($^{125}$I) ghrelin was separated from the free by rapid filtration through GF/C filters (Brandel®, Gaithersburg, Md.) which were previously soaked in 0.5% polyethyleneimine/0.1% BSA. The filters were then washed three times with 5-ml aliquots of ice-cold 50 mM Tris-HCl and 0.1% bovine serum albumin and the bound radioactivity trapped on the filters was counted by gamma spectrometry (Wallac LKB®, Gaithersburg, Md.). Specific binding was defined as the total ($^{125}$I)ghrelin bound minus that bound in the presence of 1000 nM ghrelin

TABLE 2

| Example | Structure | Ki (nM) | SEM |
|---|---|---|---|
| #12 | 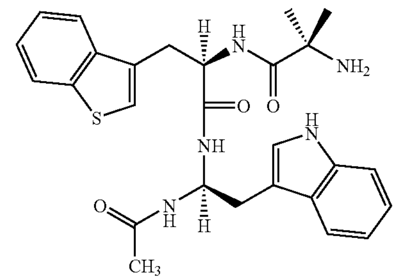 | 2.56 | 1.86 |
| #1 | 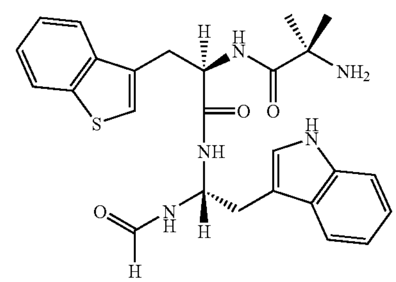 | 15.01 | 4.20 |
| #65 | 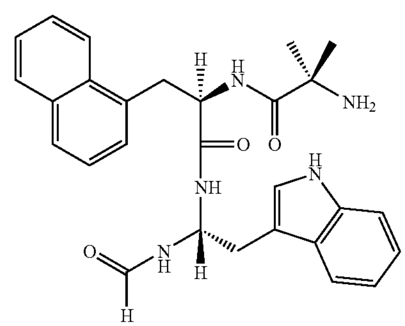 | 16.78 | 9.64 |
| #51 | 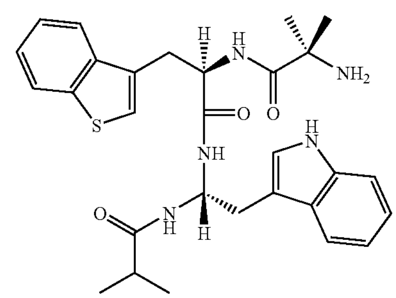 | 20.18 | 10.63 |

TABLE 2-continued

| Example | Structure | Ki (nM) | SEM |
|---|---|---|---|
| #11 | 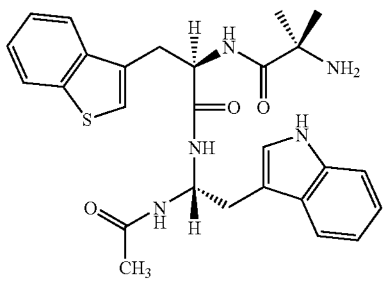 | 38.22 | 8.31 |
| #50 | 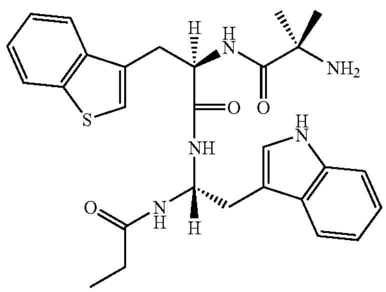 | 61.51 | 13.74 |
| #52 | 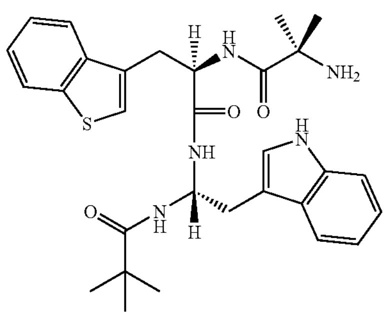 | 65.08 | 20.28 |
| #4 | 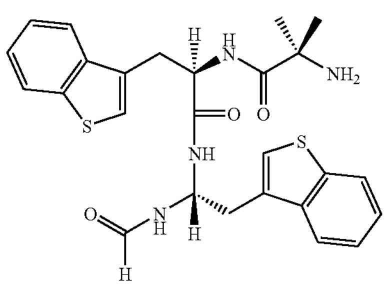 | 92.14 | 15.60 |
| #73 | 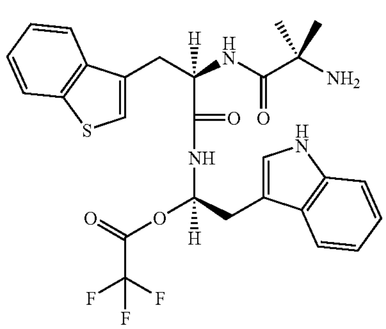 | 92.99 | 22.70 |
| #6 | | 100.30 | 22.08 |
| #18 | | 119.50 | 9.50 |
| #20 | | 132.67 | 5.70 |
| #7 | | 226.25 | 43.17 |
| #2 | | 235.88 | 88.10 |

TABLE 2-continued

| Example | Structure | Ki (nM) | SEM |
|---|---|---|---|
| #5 | (structure) | 279.50 | 90.50 |

2. GHS-R Functional Activity Assays

A. In Vitro hGHS-R1a Mediated Intracellular iCa$^{2+}$ Mobilization

Compounds of the invention were tested for their ability to stimulate hGHS-R1a mediated intracellular iCa$^{2+}$ mobilization using cells expressing hGHS-R1a. The foregoing CHO-K1 cells expressing hGHS-R1a were harvested by incubating in a 0.3% EDTA/phosphate buffered saline solution (25° C.) and washed twice by centrifugation. The washed cells were re-suspended in Hank's buffered saline solution (HBSS) for loading of the fluorescent Ca$^{2+}$ indicator Fura-2AM. Cell suspensions with a concentration of approximately 10$^6$ cells/ml were incubated with 2 μM Fura-2AM for approximately thirty minutes at about 25° C. Unloaded Fura-2AM was removed by centrifugation twice in HBBS and the final suspensions were transferred to a spectrofluorometer (Hitachi® F-2000) equipped with a magnetic stirring mechanism and a temperature-regulated cuvette holder. After equilibration to 37° C., compounds of the invention were added for measurement of intracellular Ca$^{2+}$ mobilization. The excitation and emission wavelengths were 340 and 510 nm, respectively.

B. In Vivo GH Release/Suppression

Using methods well known in the art, compounds of the present invention were tested for their ability to stimulate or suppress release of growth hormone (GH) in vivo (Deghenghi, R., et al., Life Sciences, (1994), 54:1321-8; International Patent Publication No. WO 02/08250). In order to ascertain a compound's ability to stimulate GH release in vivo, the compounds were injected subcutaneously in ten-day old rats at a predetermined dose of, e.g., 300 mg/kg. The circulating GH was measured at approximately fifteen minutes after injection and compared to GH levels in rats injected with a solvent control.

Similarly, compounds of the present invention may be tested for their ability to antagonize ghrelin-induced GH secretion in vivo. A compound may be injected subcutaneously in ten-day old rats at a predetermined dose of, e.g., 300 mg/kg, along with ghrelin. The circulating GH may be determined at, e.g., fifteen minutes after injection and compared to GH levels in rats injected with ghrelin alone.

Administration

A compound or compounds of the invention can be administered to a subject. A "subject" refers to a mammalian or non-mammalian animal including, for example, and without limitation, a human, a rat, a mouse or a farm animal. Reference to subject does not necessarily indicate the presence of a disease or disorder, thus the term subject further includes, for example, a mammalian or non-mammalian animal being dosed with a ghrelin analog as part of an experiment, a mammalian or non-mammalian animal being treated to help alleviate a disease or disorder and a mammalian or non-mammalian animal being treated prophylactically to retard or prevent the onset of a disease or disorder.

A "beneficial effect" refers to any improvement in a subject suffering from a disease or medical condition. Such an improvement may include, but is not limited to, a lessening in the severity of a subject's symptoms, an observable decrease and/or lessening of the actual ailment such as a decrease in tumor size or an increase in bone density or an actual reversal of the disease or condition.

The compounds of the invention can be formulated and administered to a subject using the guidance provided herein along with techniques well known in the art. The preferred route of administration ensures that an effective amount of compound reaches the target. Guidelines for pharmaceutical administration in general are provided in, for example, *Remington's Pharmaceutical Sciences* 18$^{th}$ *Edition*, Ed. Gennaro, Mack Publishing, (1990) and *Modern Pharmaceutics* 2$^{nd}$ *Edition*, Eds. Banker and Rhodes, Marcel Dekker, Inc., (1990), both of which are hereby incorporated by reference herein.

The compounds of the invention can be prepared as acidic or basic salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

The compounds of the invention can be administered by injection and/or by using different routes including oral, nasal, transdermal and transmucosal. Active ingredients to be administered orally as a suspension can be prepared according to techniques well known in the art of pharmaceutical formulation and may contain microcrystalline cellulose as non-active bulk, alginic acid or sodium alginate as a suspending agent, methylcellulose as a viscosity enhancer and sugars as sweeteners/flavoring agents. As immediate release tablets, compositions comprising compounds of the instant invention may further contain microcrystalline cellulose, dicalcium phosphate, starch, magnesium stearate and lactose and/or other excipients, binders, extenders, disintegrants, diluents and lubricants.

Nasal aerosol or inhalation formulations may be prepared, for example, as solutions in saline employing benzyl alcohol or other suitable preservatives, absorption promoters to enhance bioavailability, fluorocarbons and/or solubilizing or dispersing agents.

The compounds of the invention may also be administered intravenous (both bolus and infusion), intraperitoneal, subcutaneous, topical with or without occlusion or intramuscular form. When administered by injection, the injectable solution or suspension may be formulated using suitable non-toxic, parenterally-acceptable diluents or solvents, such as Ringer's solution or isotonic sodium chloride solution, or suitable dispersing or wetting and suspending agents, such as sterile, bland, fixed oils, including synthetic mono- or diglycerides and fatty acids, including oleic add.

Suitable dosing regimens are preferably determined taking into account factors well known in the art including type of subject being dosed, age, weight, sex and medical condition of the subject; the route of administration; the renal and hepatic function of the subject; the desired effect; and the particular compound employed.

Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a subject is expected to be between 0.01 and 1,000 mg per subject per day.

The compounds of the invention can be provided in a kit. Such a kit typically contains an active compound in dosage forms for administration. A dosage form contains a sufficient amount of active compound such that a desirable effect can be obtained when administered to a subject during regular intervals, such as 1 to 6 times a day, during the course of 1 or more days. Preferably, a kit contains instructions indicating the use of the dosage form to achieve a desirable effect and the amount of dosage form to be taken over a specified time period.

The invention has been described in an illustrative manner, and it is to be understood that the terminology which has been used is intended to be in the nature of words of description rather than of limitation. Obviously, many modifications and variations of the present invention are possible in light of the above teachings. It is, therefore, to be understood that within the scope of the appended claims the invention may be practiced otherwise than as specifically described.

The patent and scientific literature referred to herein represents knowledge that is available to those with skill in the art. All patents, patent publications and other publications cited herein are hereby incorporated by reference in their entirety.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:
1. A compound of the formula (I)

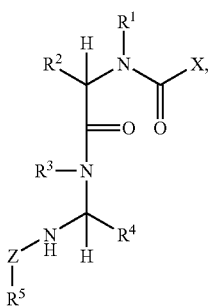

(I)

wherein
X is

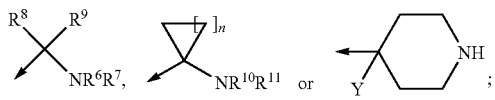

Y is H or $NR^{12}R^{13}$;
Z is —C(O)— or —SO$_2$—;
n is, independently for each occurrence. 1, 2, 3, 4, 5, 6, 7, or 8;
$R^1$ and $R^3$ each is, independently, H or ($C_1$-$C_4$)alkyl;
$R^2$ and $R^4$ each is, independently,

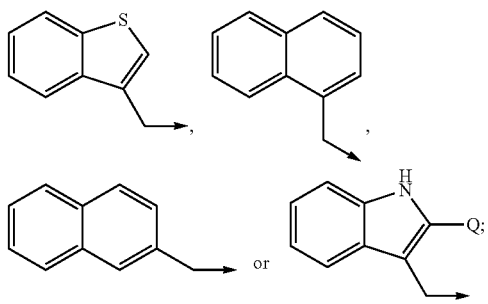

$R^5$ is H, ($C_1$-$C_6$)alkyl, ($C_2$-$C_6$)alkenyl, ($C_2$-$C_6$)alkynyl, substituted ($C_1$-$C_6$)alkyl, substituted ($C_2$-$C_6$)alkenyl, substituted ($C_2$-$C_6$)alkynyl, aryl, alkylaryl, alkylarylalkyl or arylalkylaryl;
$R^8$ and $R^9$ each is, independently, ($C_1$-$C_6$)alkyl or substituted ($C_1$-$C_6$)alkyl;
$R^6$, $R^7$, $R^{10}$, $R^{11}$, $R^{12}$ and $R^{13}$ each is, independently, H, ($C_1$-$C_6$)alkyl or substituted ($C_1$-$C_6$)alkyl; and
Q is H or ($C_1$-$C_4$)alkyl;
provided that:
at least one of $R^2$ and $R^4$ is

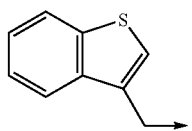

in said compound;
or a pharmaceutically acceptable salt thereof.
2. A compound according to claim 1, wherein
$R^2$ is

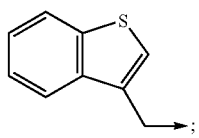

and
$R^4$ is

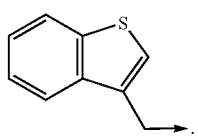

3. A compound according to claim 2, wherein Z is —C(O)—.

4. A compound according to claim 3, wherein X is

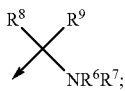

$R^6$ and $R^7$ each is, independently, H; and
$R^8$ and $R^9$ each is, independently, $CH_3$.

5. A compound of claim 4, wherein
$R^1$ is H;
$R^3$ is H or methyl; and
$R^5$ is H, methyl, ethyl, isopropyl or t-butyl.

6. A compound according to claim 3, wherein X is

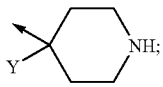

and
Y is H.

7. A compound according to claim 6 wherein
$R^1$ is H;
$R^3$ is H or methyl; and
$R^5$ is H, methyl, ethyl, isopropyl or t-butyl.

8. A compound according to claim 3, wherein X is

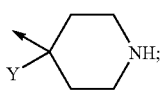

and
Y is $NR^{12}R^{13}$;
wherein both $R^{12}$ and $R^{13}$ are each H.

9. A compound of claim 8 wherein
$R^1$ is H;
$R^3$ is H or methyl; and
$R^5$ is H, methyl, ethyl, isopropyl or t-butyl.

10. A compound according to claim 2, wherein Z is —$SO_2$—.

11. A compound according to claim 10, wherein X is

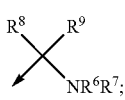

$R^6$ and $R^7$ each is, independently, H; and
$R^8$ and $R^9$ each is, independently, $CH_3$.

12. A compound of claim 11, wherein
$R^1$ is H;
$R^3$ is H or methyl; and
$R^5$ is H, methyl, ethyl, isopropyl or t-butyl.

13. A compound according to claim 10, wherein X is

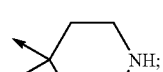

and
Y is H.

14. A compound according to claim 13 wherein
$R^1$ is H;
$R^3$ is H or methyl; and
$R^5$ is H, methyl, ethyl, isopropyl or t-butyl.

15. A compound according to claim 10, wherein X is

and
Y is $NR^{12}R^{13}$;
wherein both $R^{12}$ and $R^{13}$ are each H.

16. A compound of claim 15 wherein
$R^1$ is H;
$R^3$ is H or methyl; and
$R^5$ is H, methyl, ethyl, isopropyl or t-butyl.

17. A compound of claim 2 selected from the group consisting of:

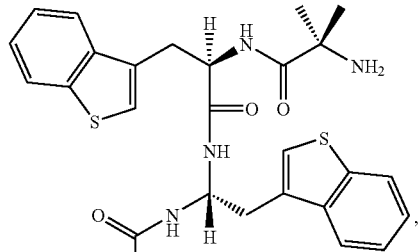

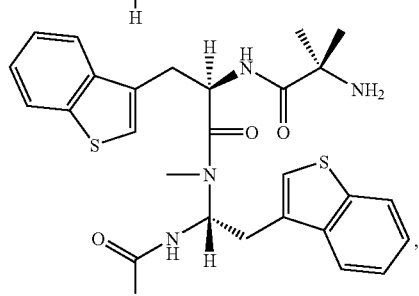

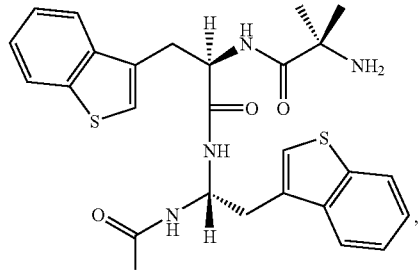

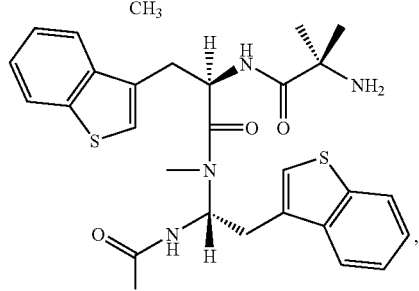

107
-continued
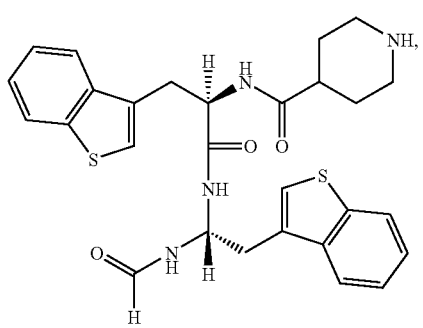
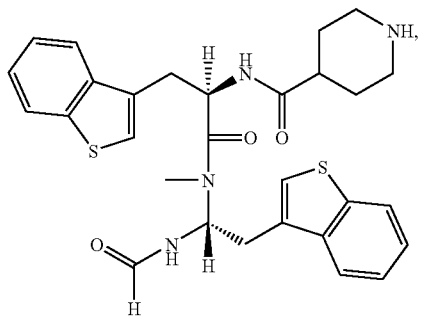
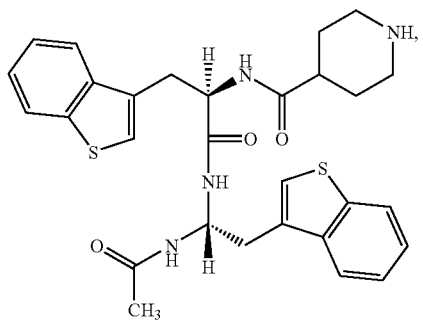
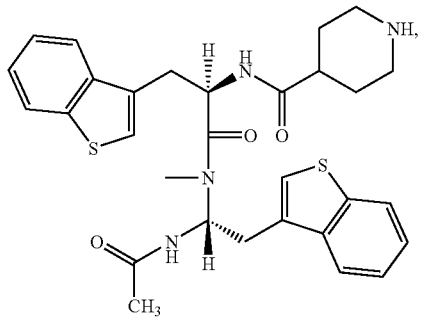
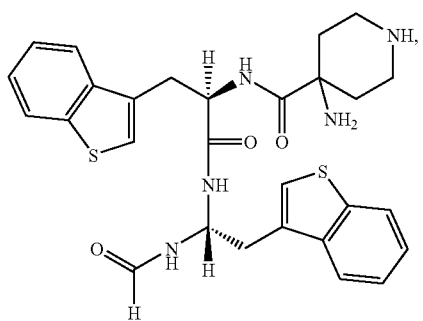
108
-continued
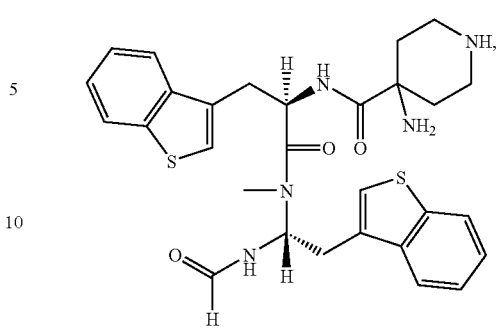
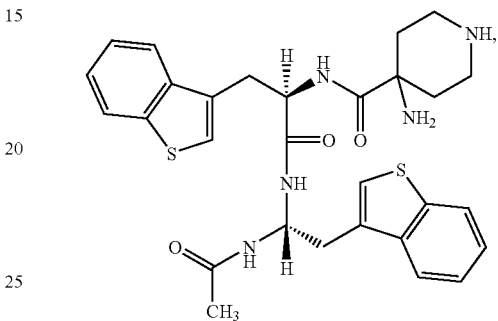
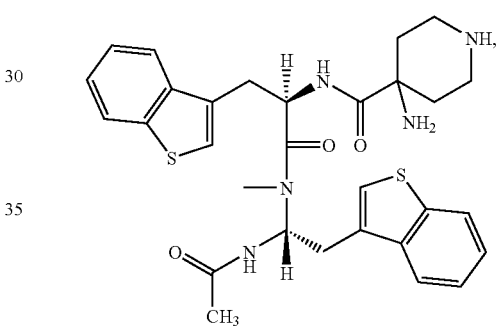
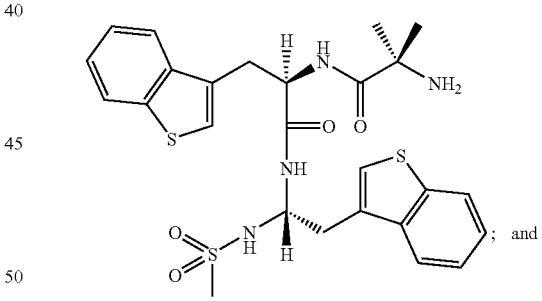
; and
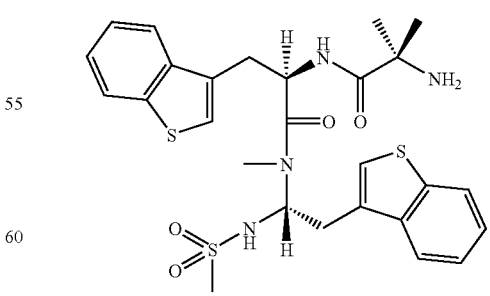
or a pharmaceutically acceptable salt thereof.

18. A compound according to claim 1, wherein R² is
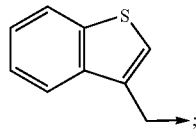
and
R⁴ is
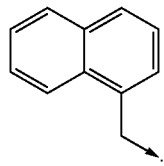
19. A compound of claim 18 selected from the group consisting of:
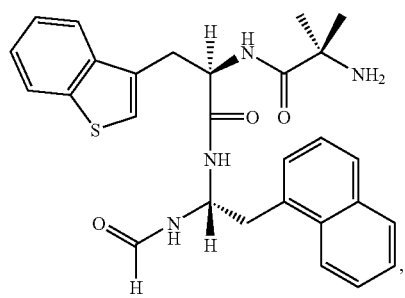
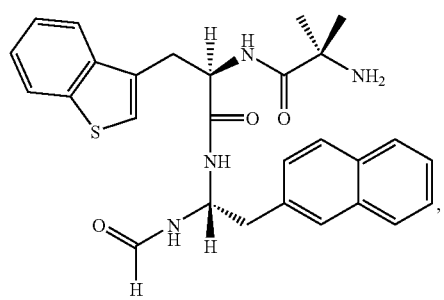
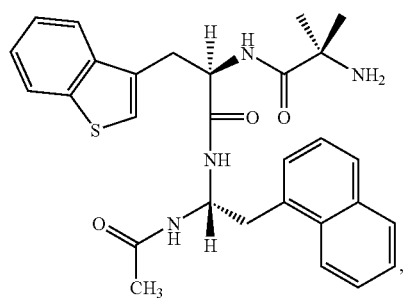
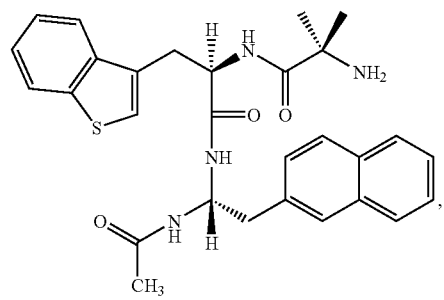
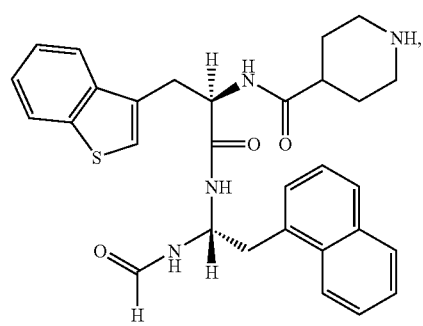
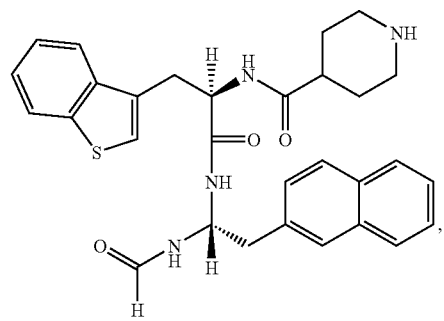
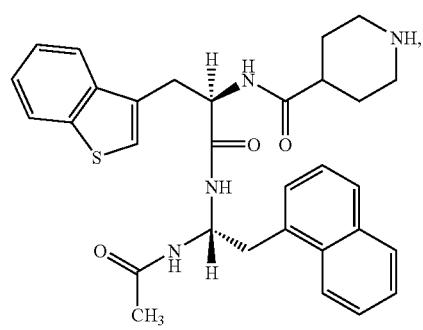
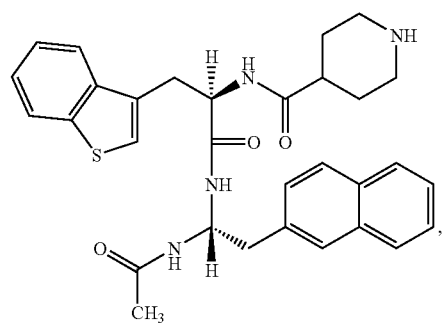

-continued
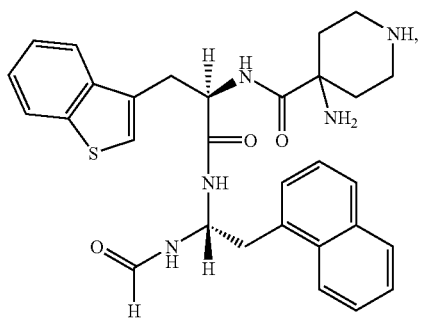
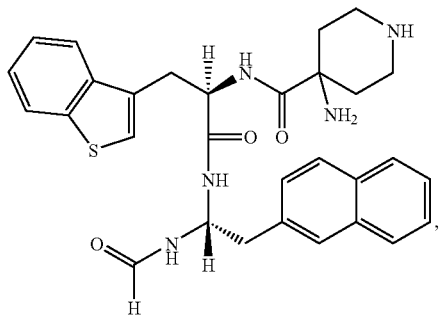
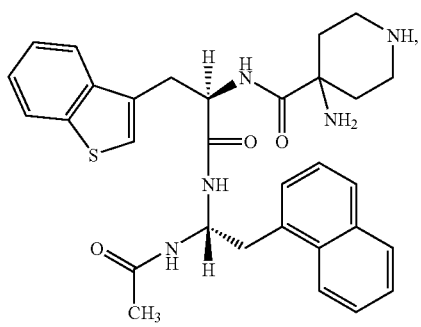
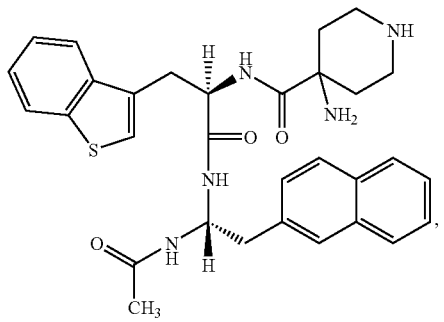
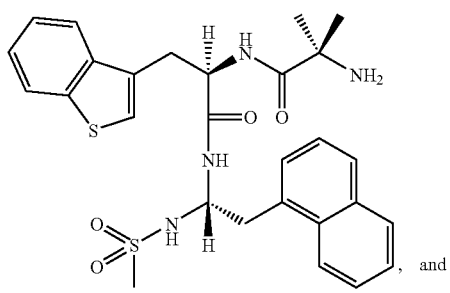
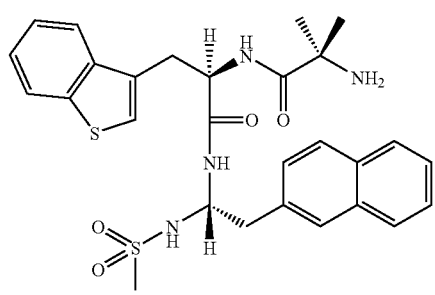
or a pharmaceutically acceptable salt thereof.
20. A compound according to claim 1, wherein R² is
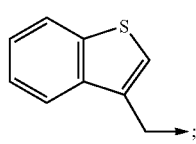
and
R⁴ is
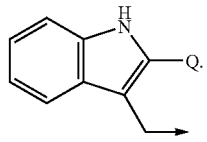
21. A compound of claim 20 selected from the group consisting of:
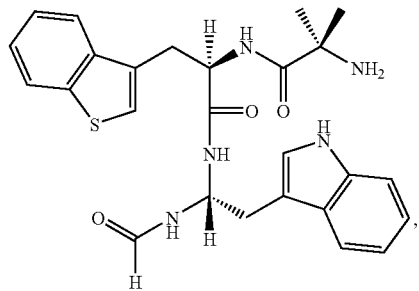
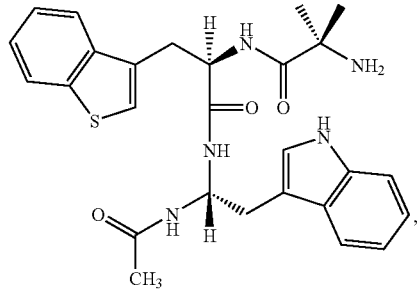

113
-continued
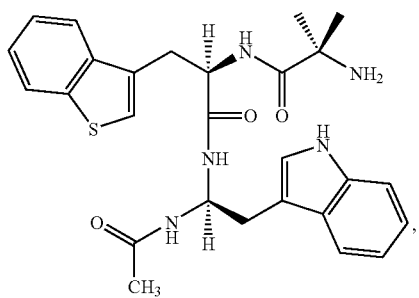
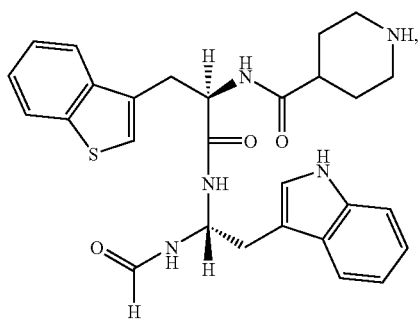
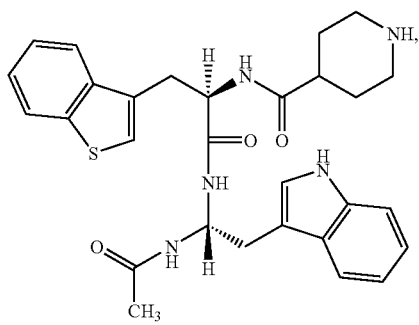
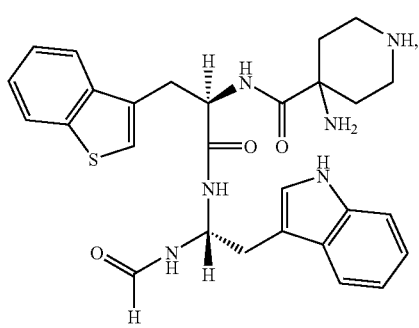
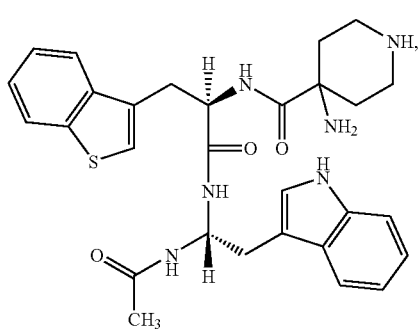
114
-continued
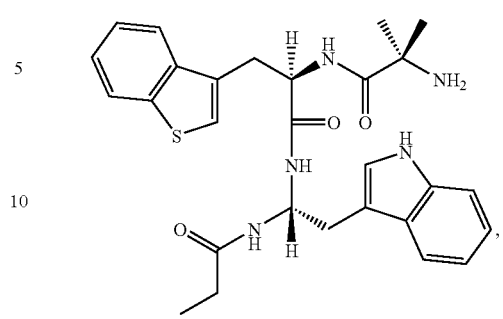
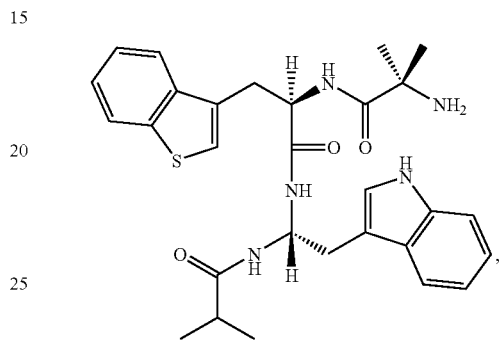
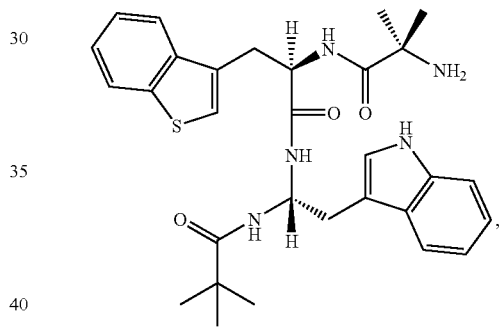
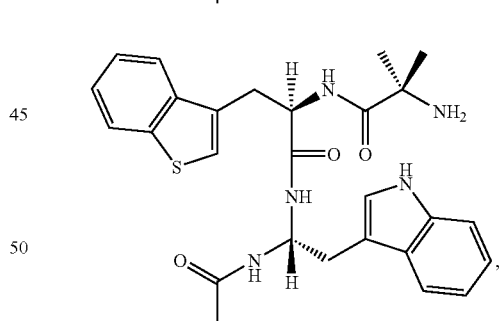
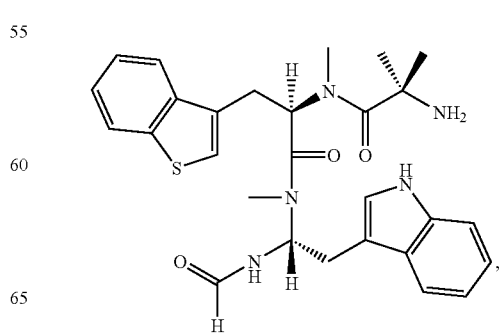

-continued
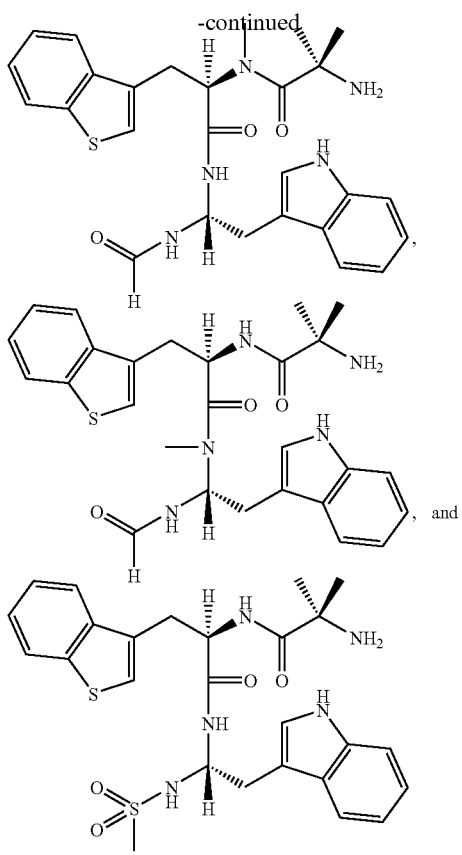
or a pharmaceutically acceptable salt thereof.
22. A compound according to claim 1, wherein R² is
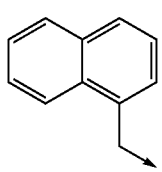 or 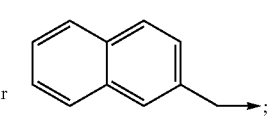 ; and
R⁴ is
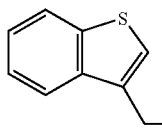 .
23. A compound of claim 22 selected from the group consisting of:
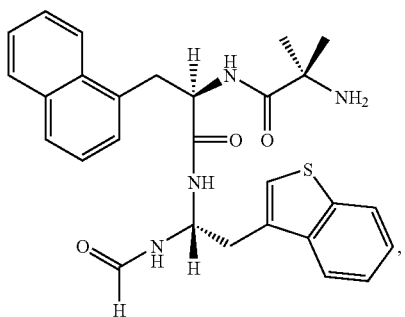
-continued
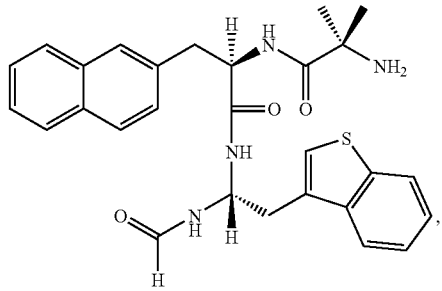
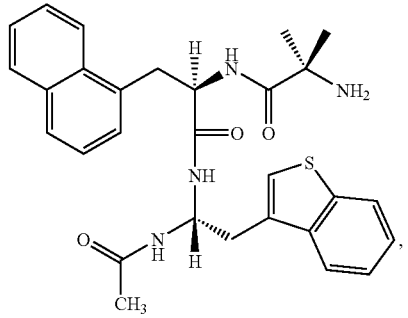
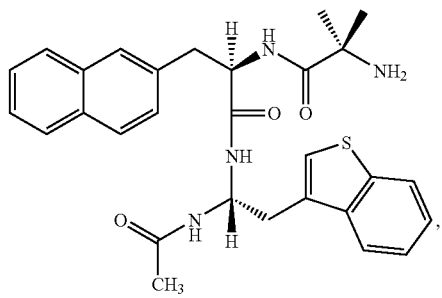
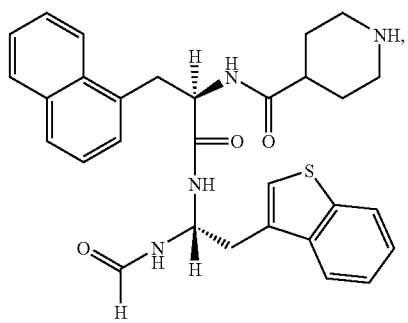
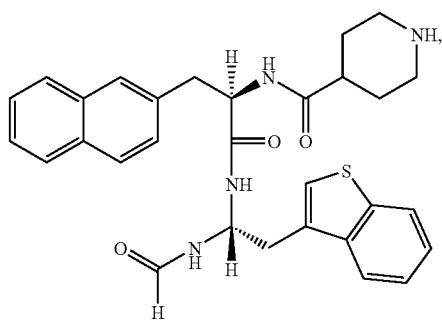

117
-continued
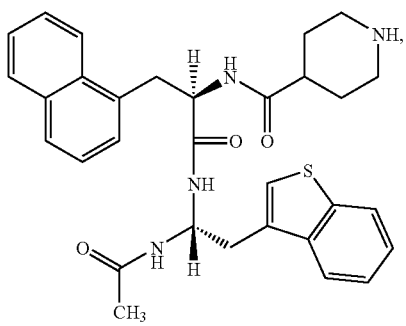
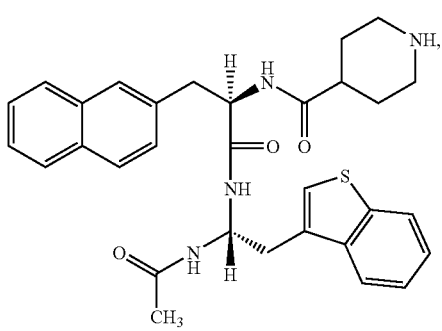
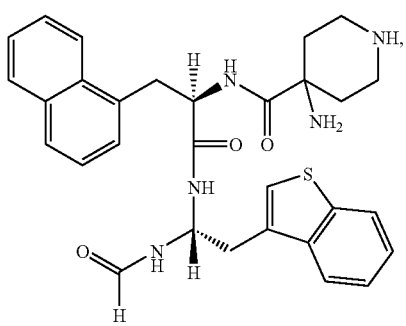
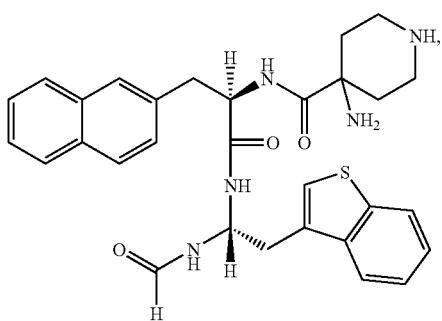
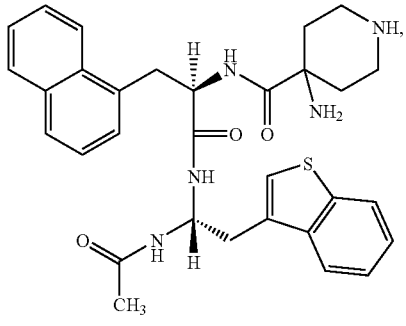
118
-continued
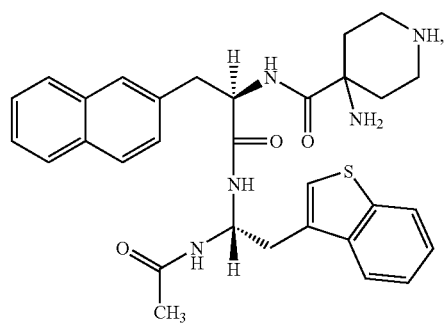
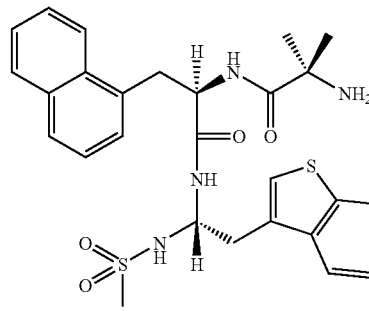, and
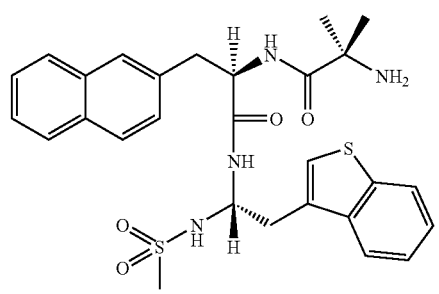
or a pharmaceutically acceptable salt thereof.
24. A compound according to claim 1, wherein R² is
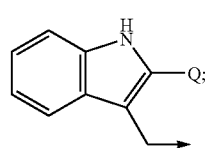
and
R⁴ is
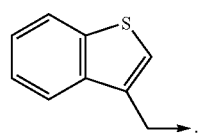
25. A compound according to claim 24 wherein Q is H.

26. A compound of claim 25 selected from the group consisting of:
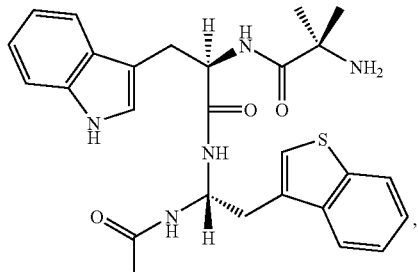
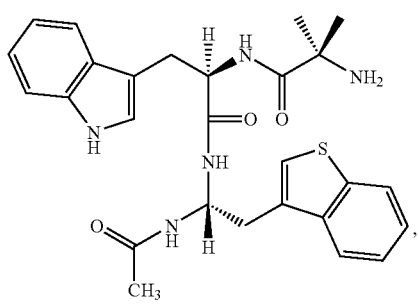
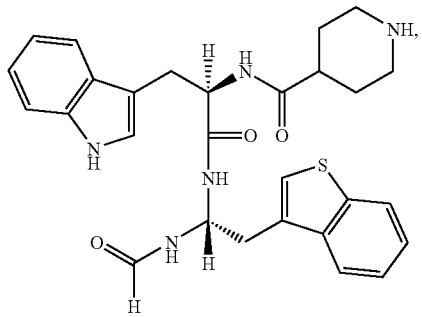
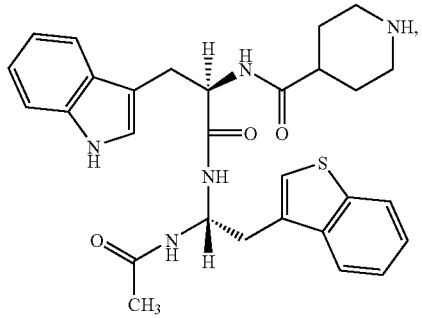
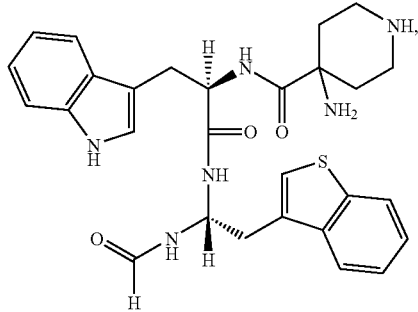
-continued
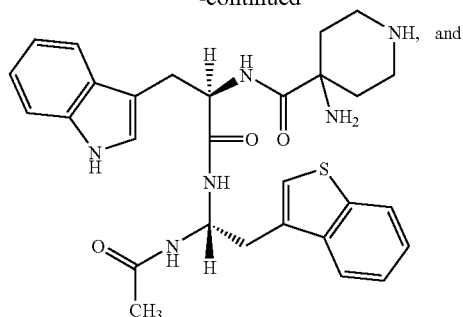
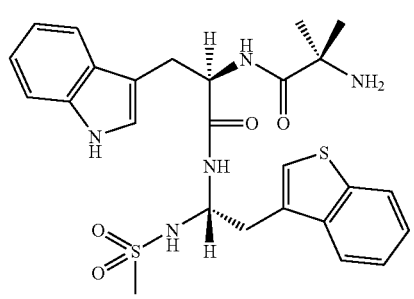
or a pharmaceutically acceptable salt thereof.
27. A compound according to claim 1, wherein said compound is according to the formula:
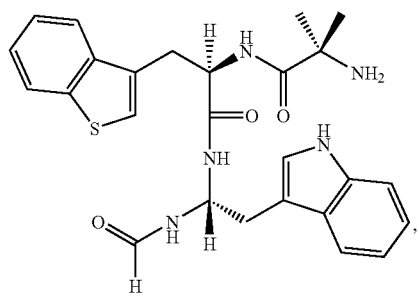
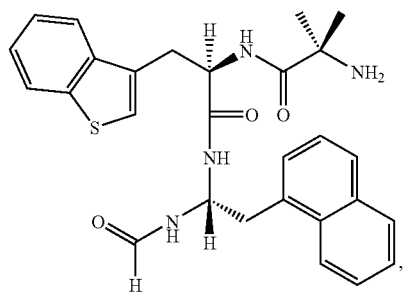
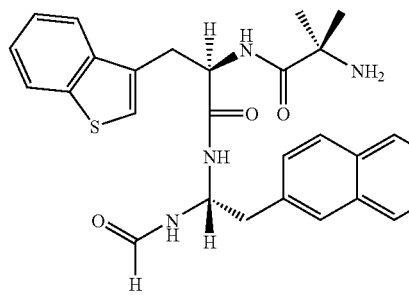

121
-continued
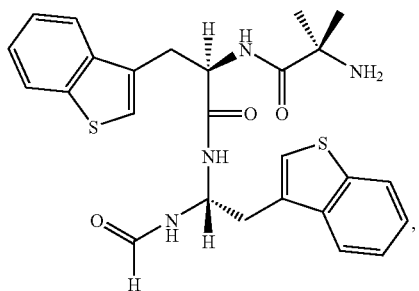
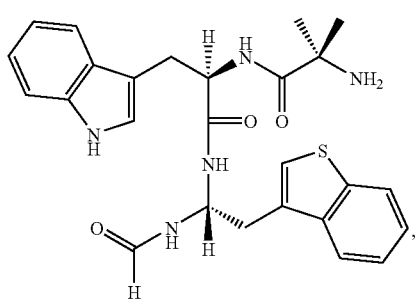
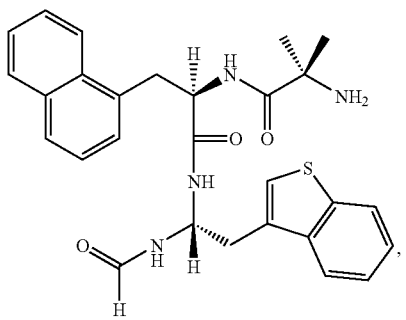
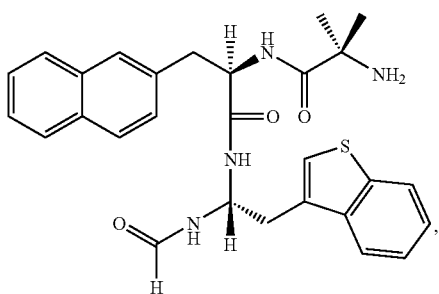
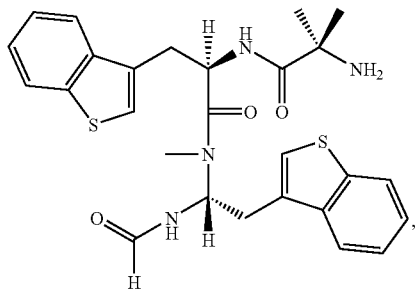
122
-continued
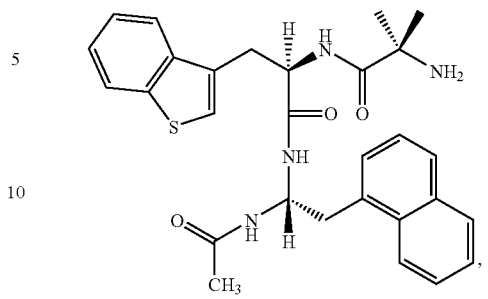
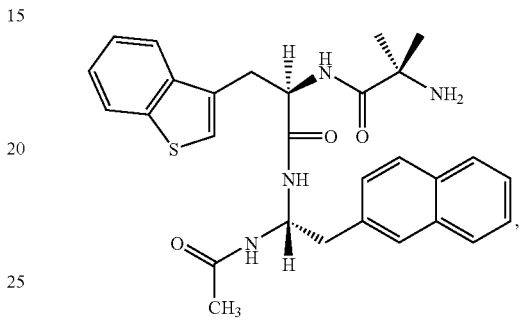
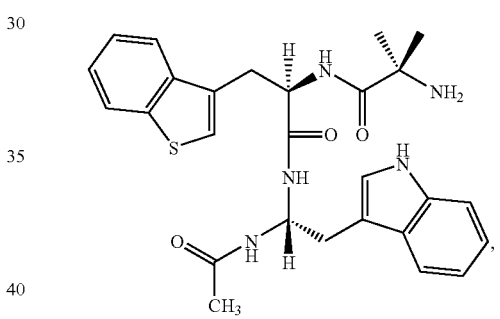
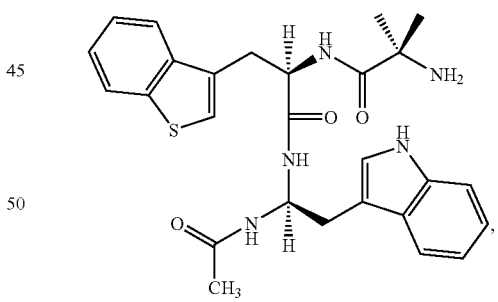
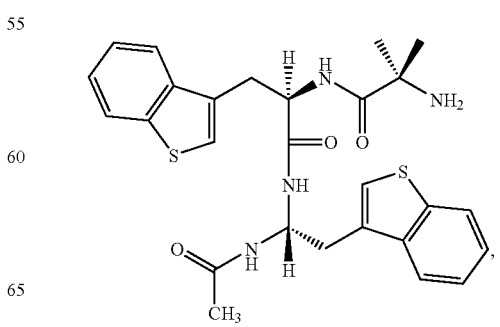

| 123 -continued | 124 -continued |
|---|---|
| 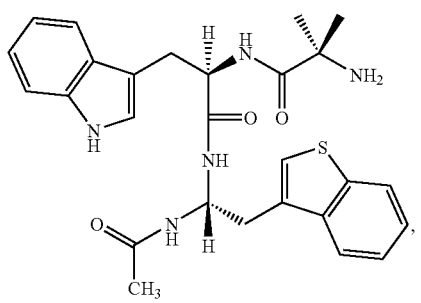 | 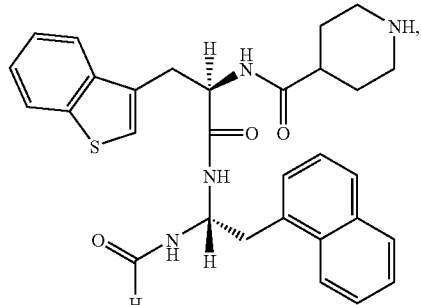 |
| 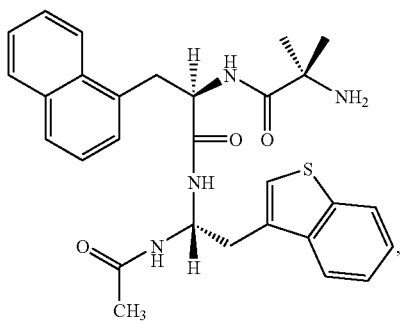 | 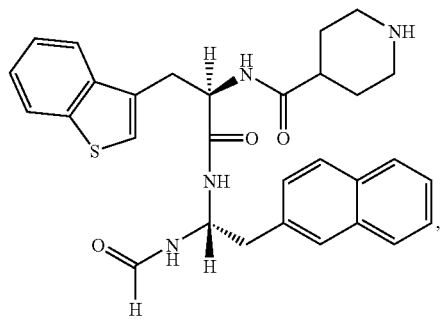 |
| 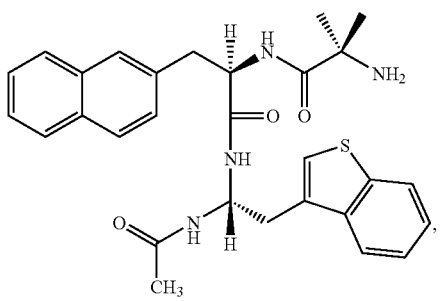 | 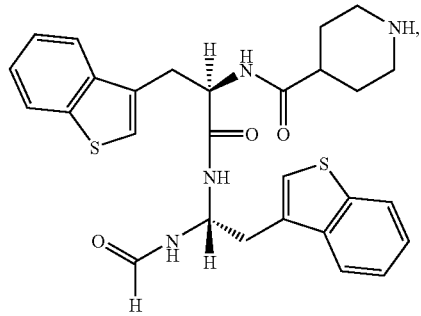 |
| 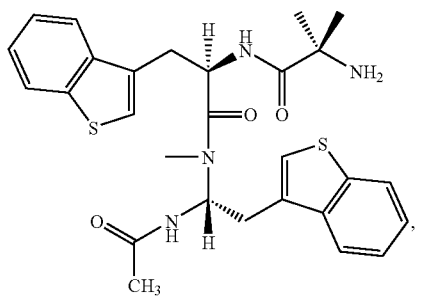 | 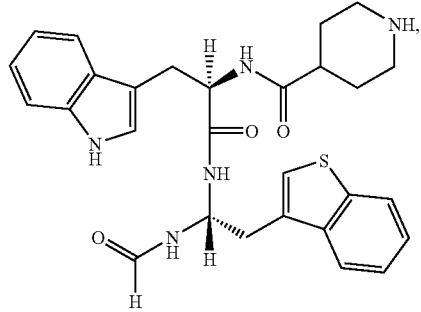 |
| 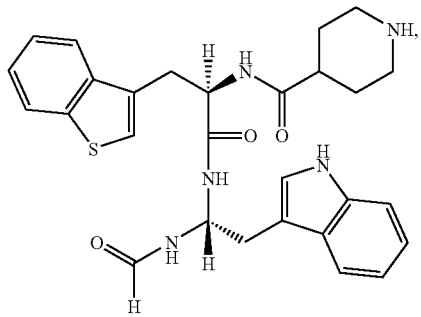 | 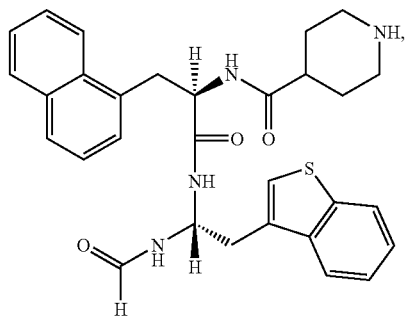 |

125
-continued
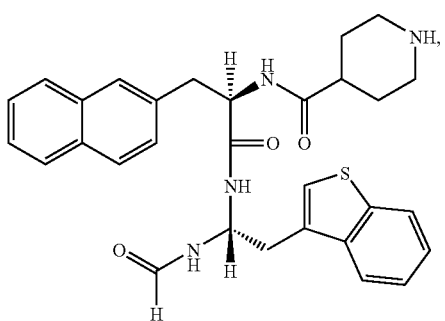
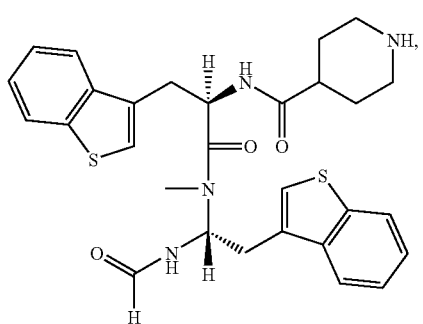
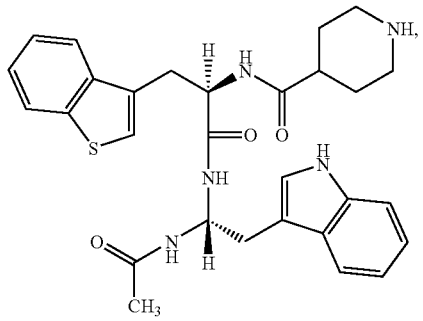
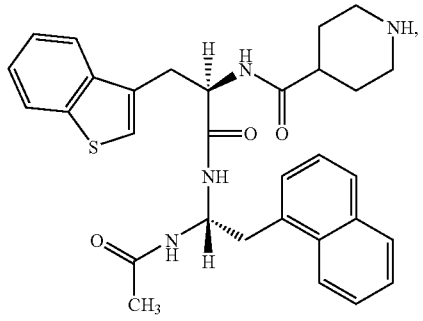
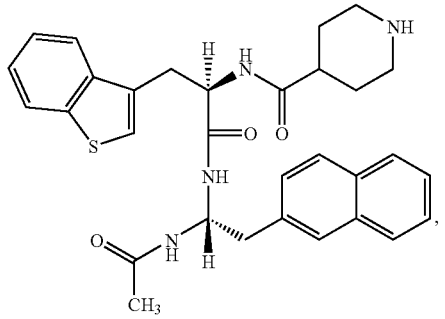
126
-continued
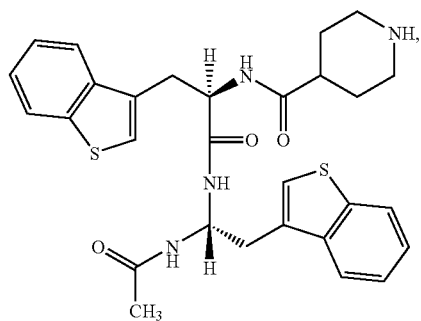
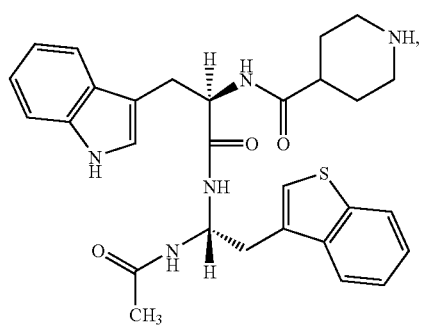
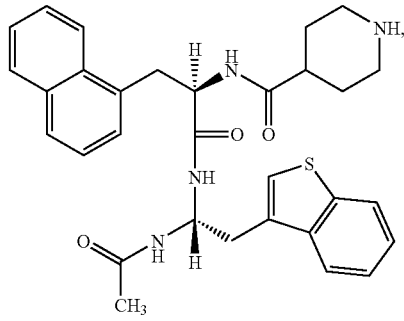
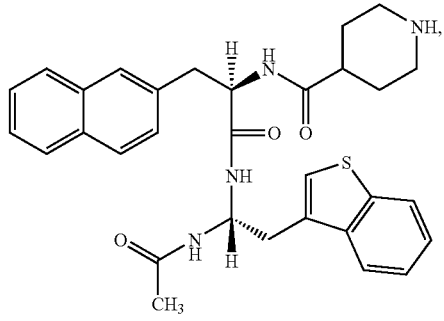
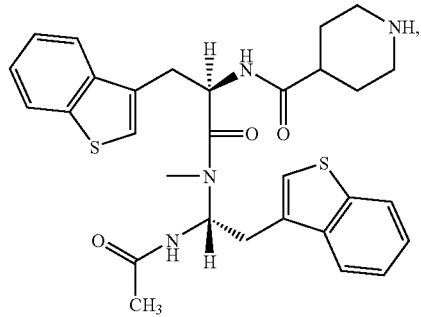

127
-continued
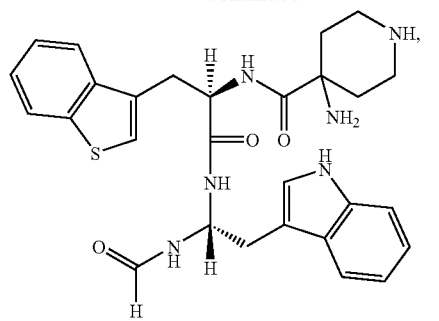
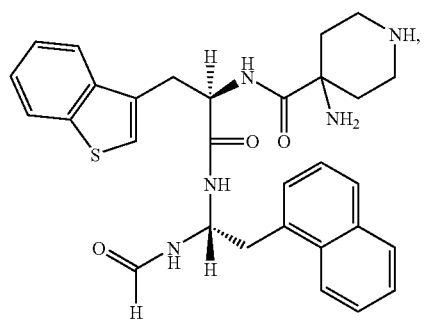
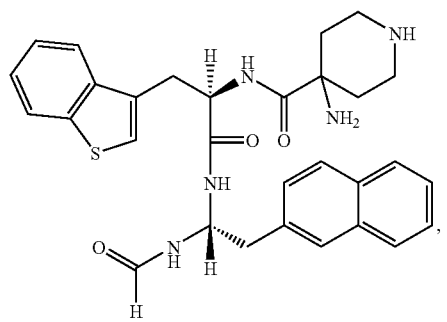
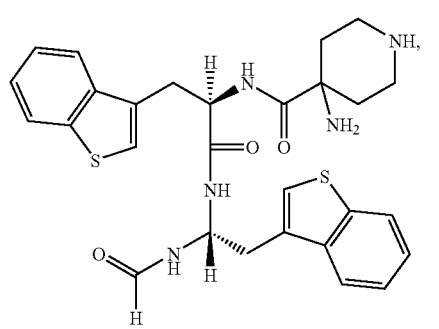
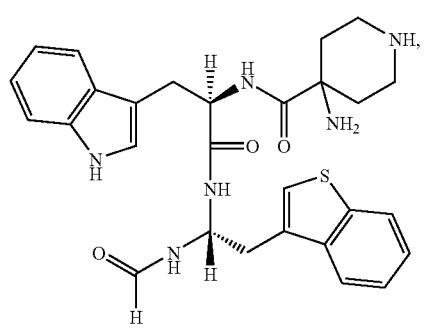
128
-continued
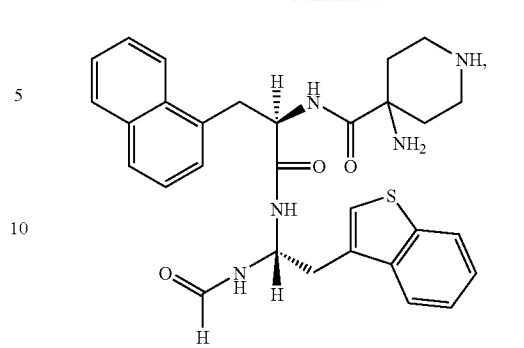
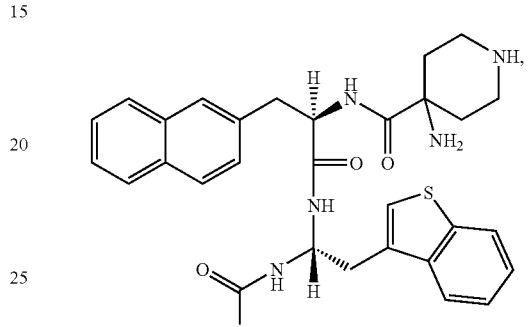
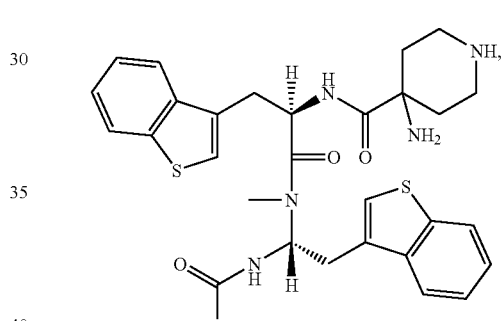
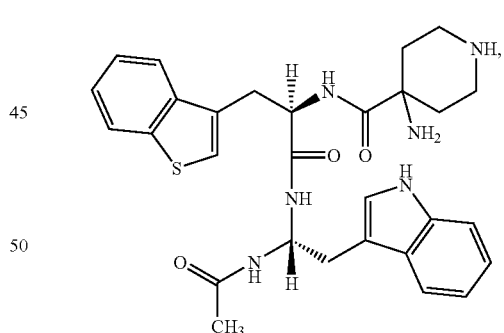
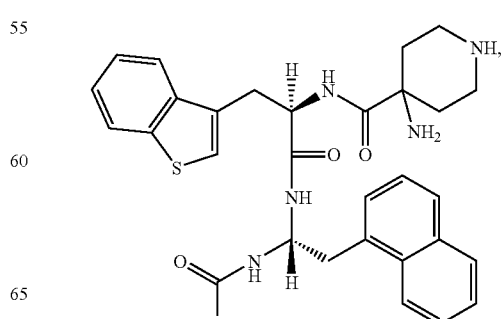

129
-continued
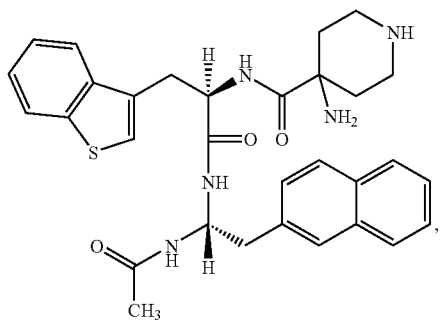
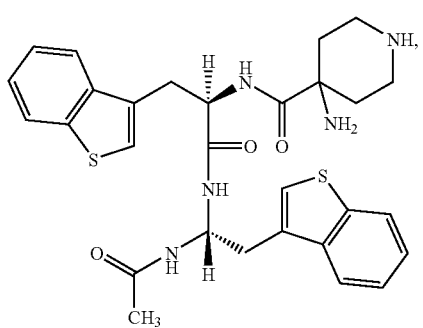
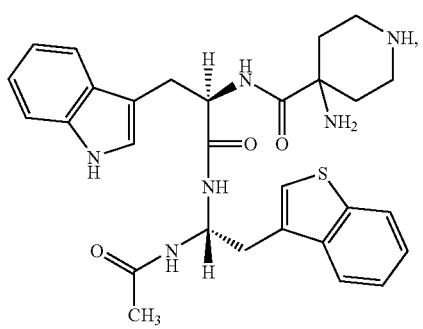
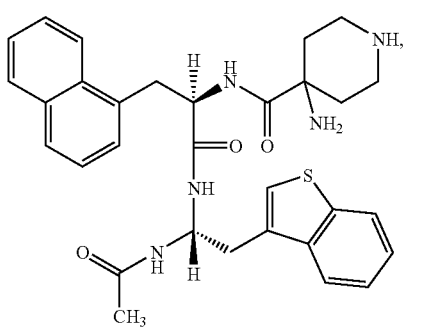
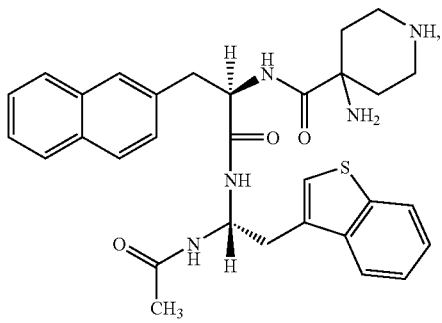
130
-continued
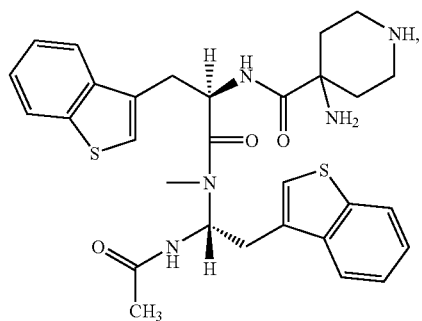
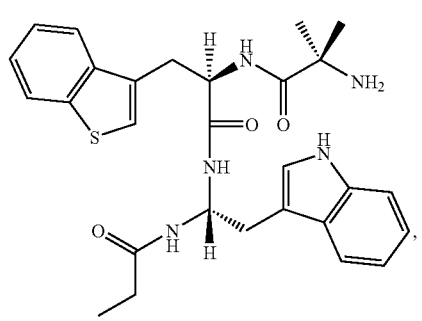
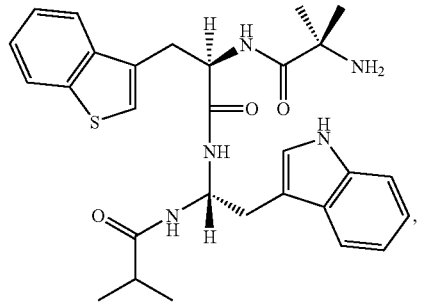
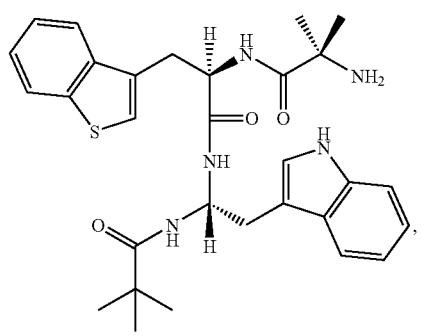
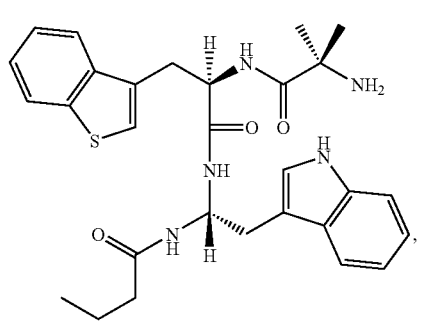

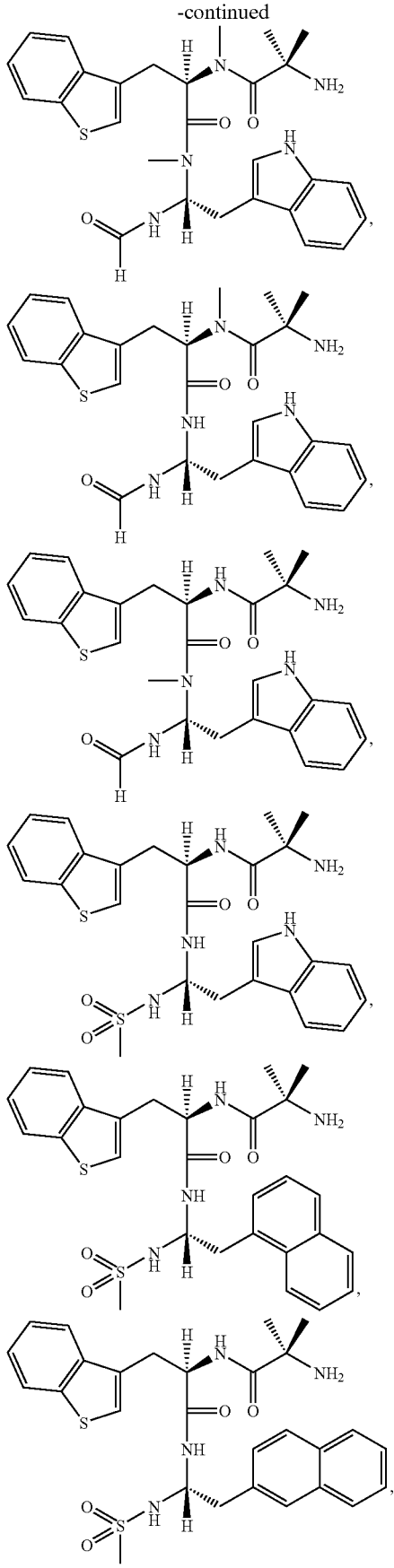
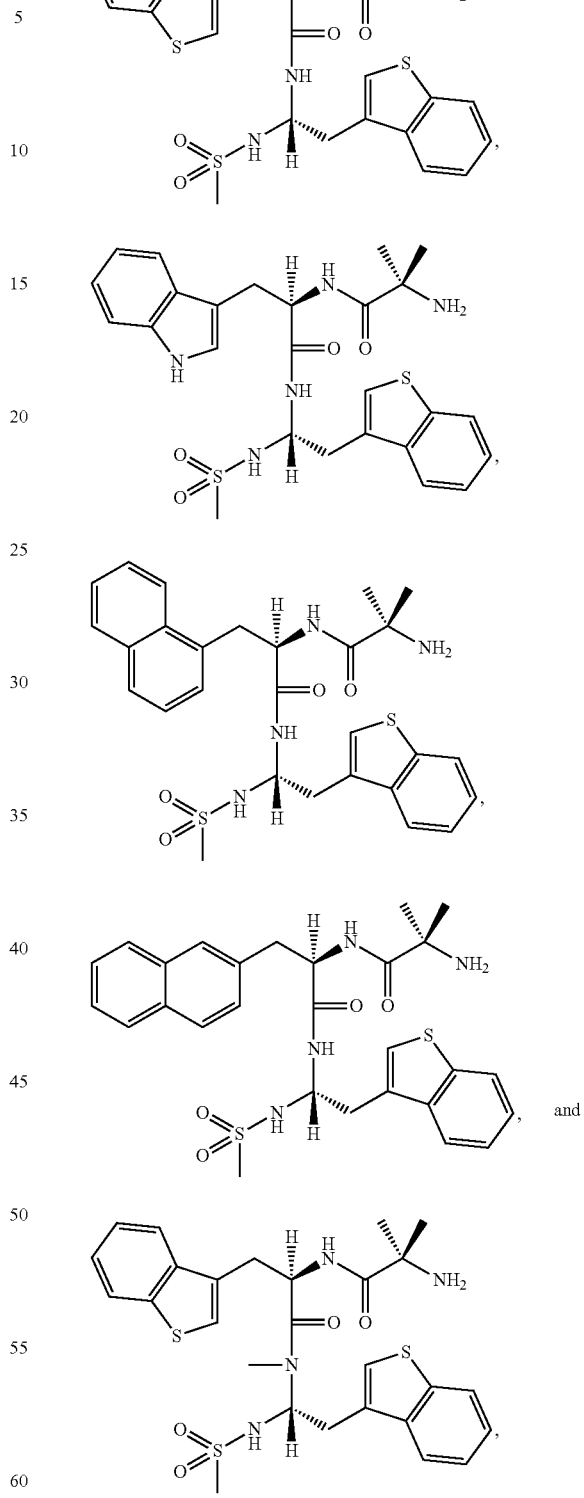
or a pharmaceutically acceptable salt thereof.
28. A pharmaceutical compositions comprising a compound of claim 27.
29. The composition of claim 28, in combination with a pharmaceutically acceptable carrier.

30. A compound according to claim 27, wherein said compound is according to the formula:
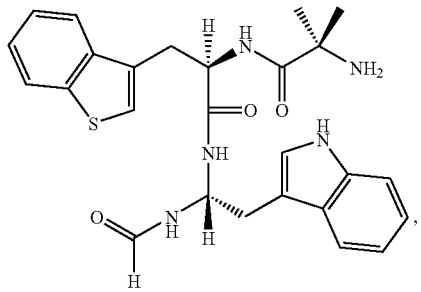
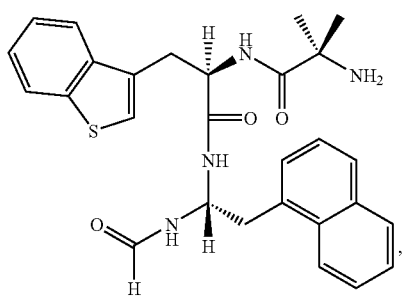
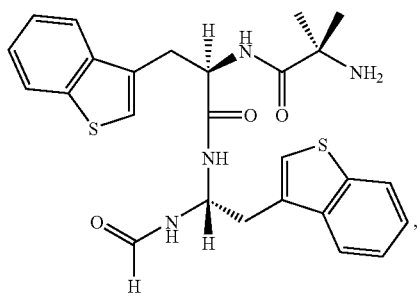
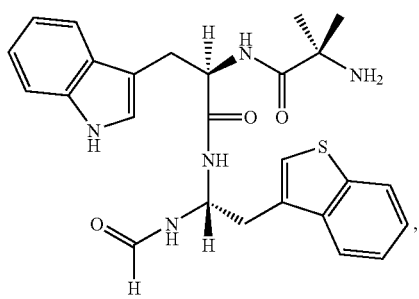
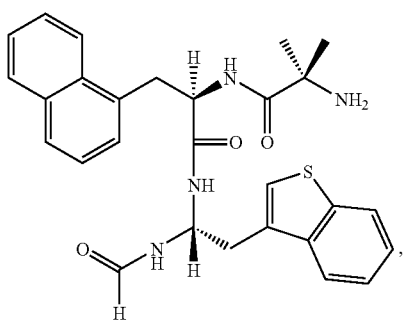
-continued
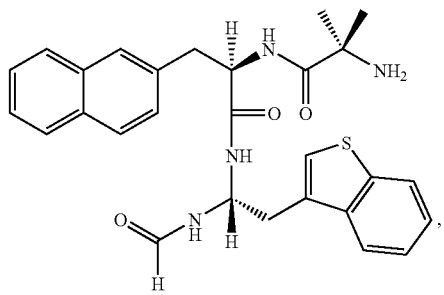
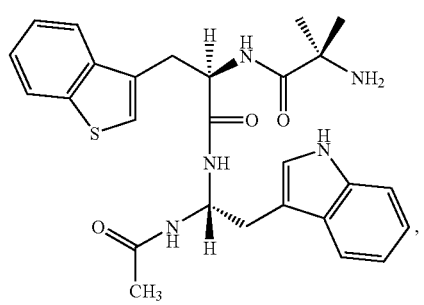
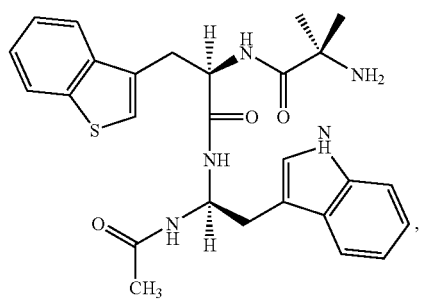
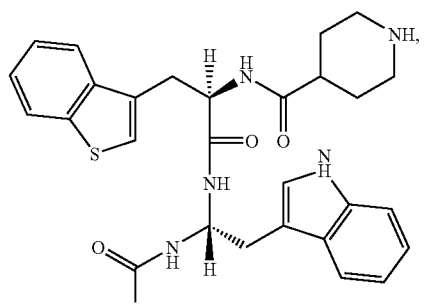
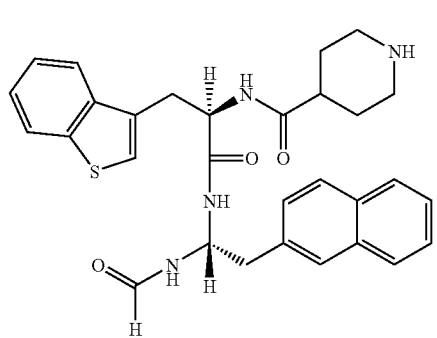

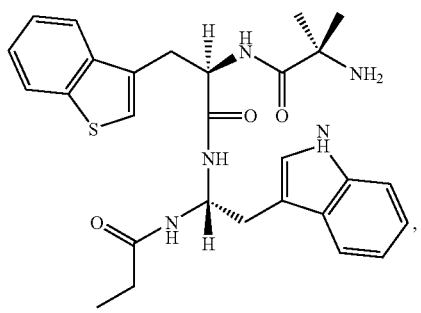
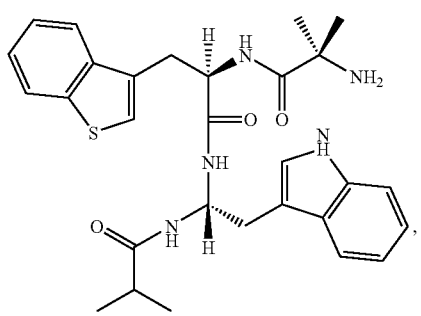
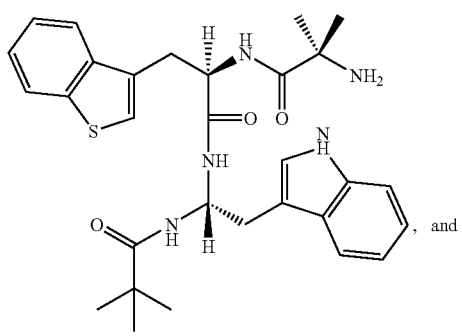, and
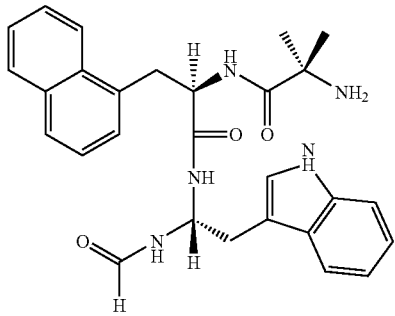
or a pharmaceutically acceptable salt thereof.
31. A pharmaceutical compositions comprising a compound of claim 30.
32. The composition of claim 31, in combination with a pharmaceutically acceptable carrier.
33. A compound according to claim 30, wherein said compound is according to the formula:
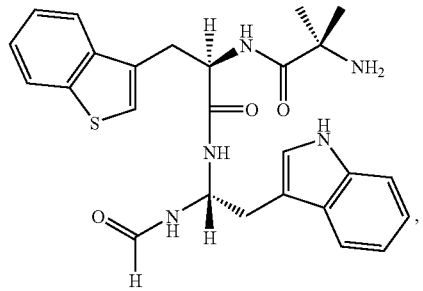
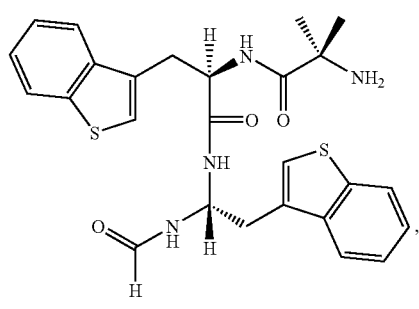
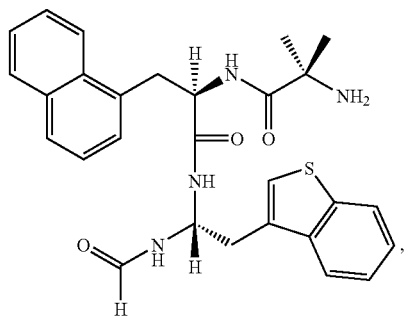
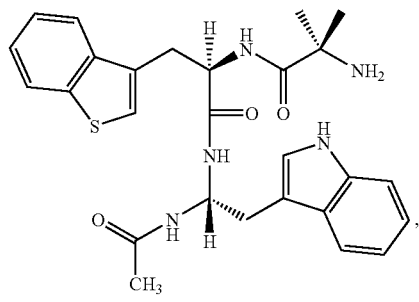
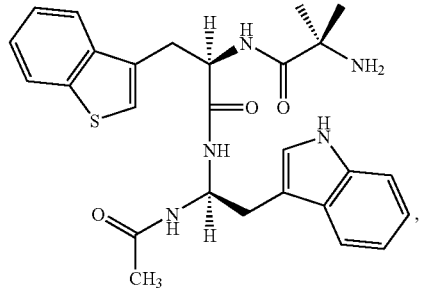

-continued

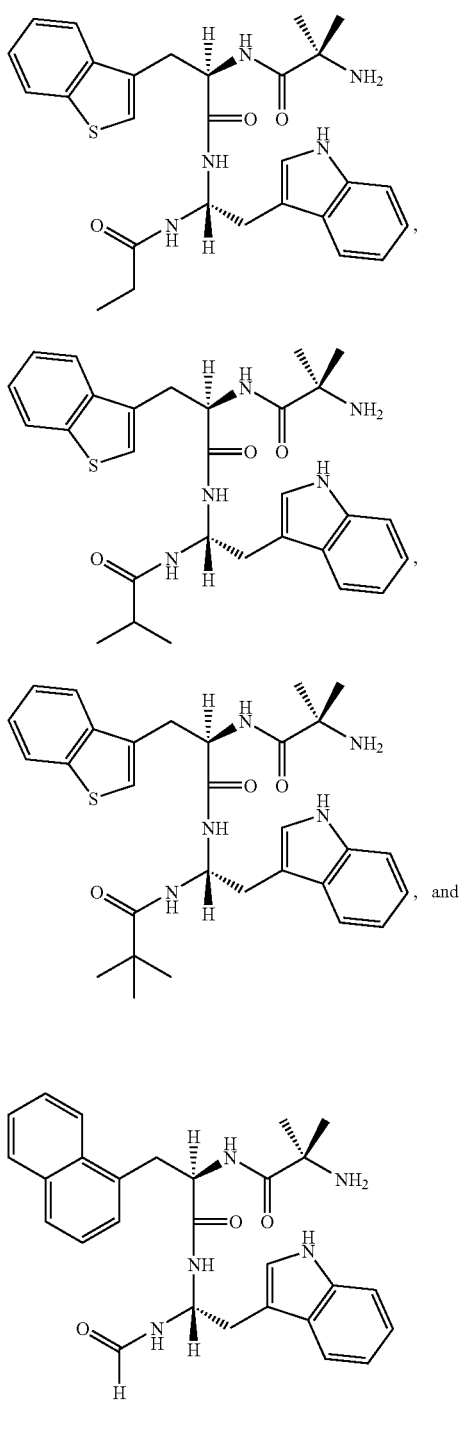

or a pharmaceutically acceptable salt thereof.

34. A pharmaceutical compositions comprising a compound of claim 33.

35. The composition of claim 34, in combination with a pharmaceutically acceptable carrier.

36. A compound according to claim 33, wherein said compound is according to the formula:

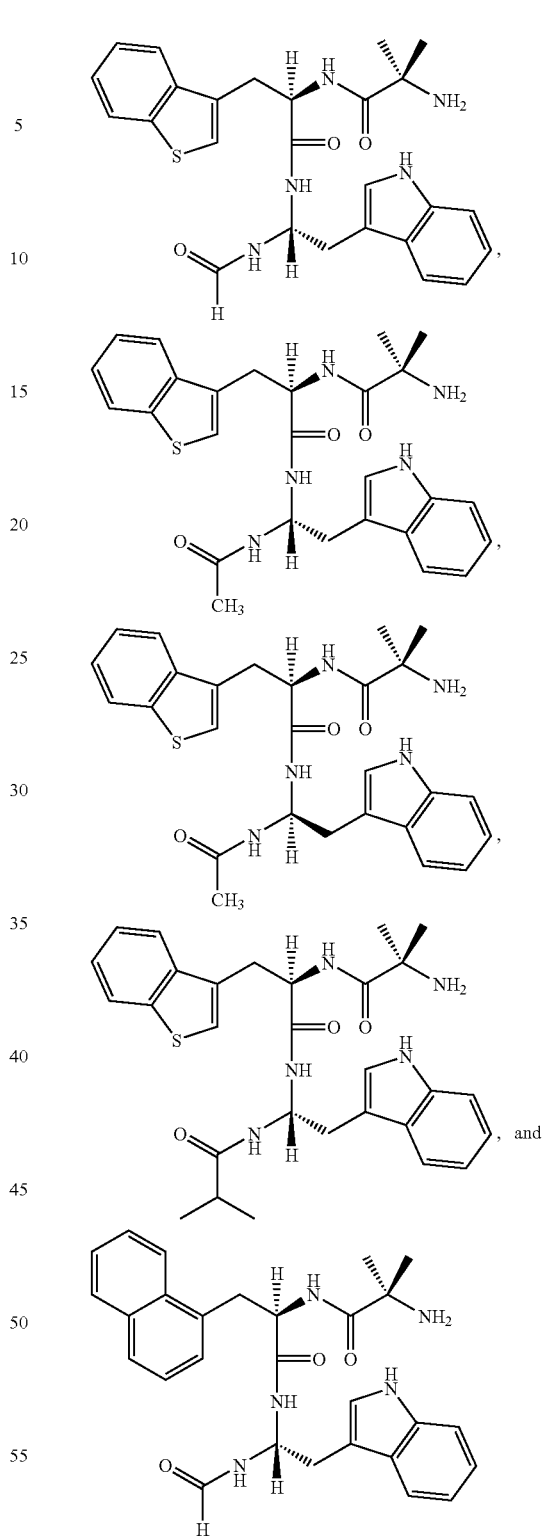

or a pharmaceutically acceptable salt thereof.

37. A pharmaceutical compositions comprising a compound of claim 36.

38. The composition of claim 37, in combination with a pharmaceutically acceptable carrier.

39. A compound according to claim 36, wherein said compound is according to the formula:

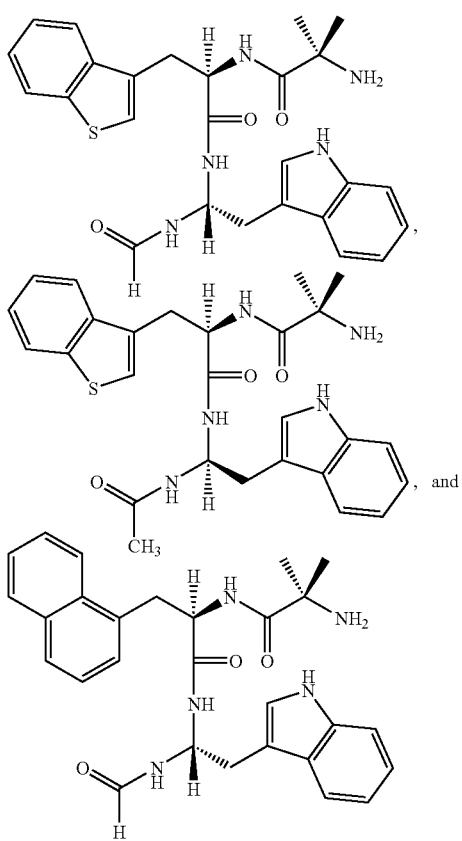

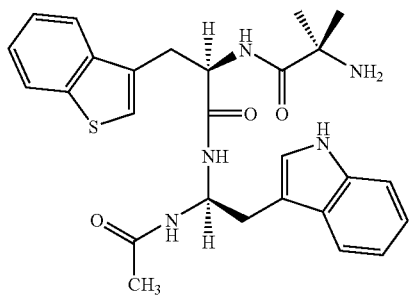

or a pharmaceutically acceptable salt thereof.

40. A pharmaceutical compositions comprising a compound of claim 39.

41. The composition of claim 40, in combination with a pharmaceutically acceptable carrier.

42. A compound according to claim 39, wherein said compound is according to the formula:

or a pharmaceutically acceptable salt thereof.

43. A pharmaceutical compositions comprising a compound of claim 42.

44. The composition of claim 43, in combination with a pharmaceutically acceptable carrier.

45. A compound according to claim 27, wherein said compound is according to the formula:

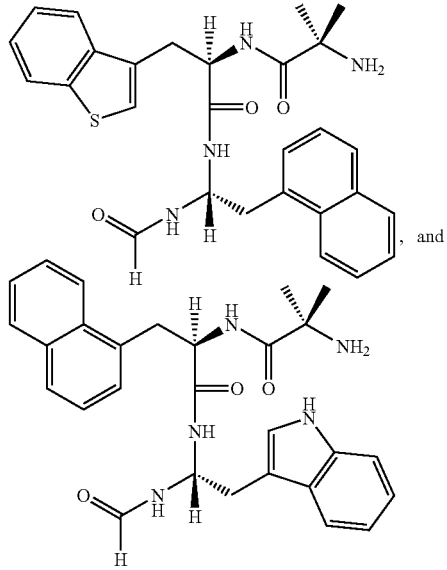

or a pharmaceutically acceptable salt thereof.

46. A pharmaceutical compositions comprising a compound of claim 45.

47. The composition of claim 46, in combination with a pharmaceutically acceptable carrier.

48. A compound according to claim 27, wherein said compound is according to the formula:

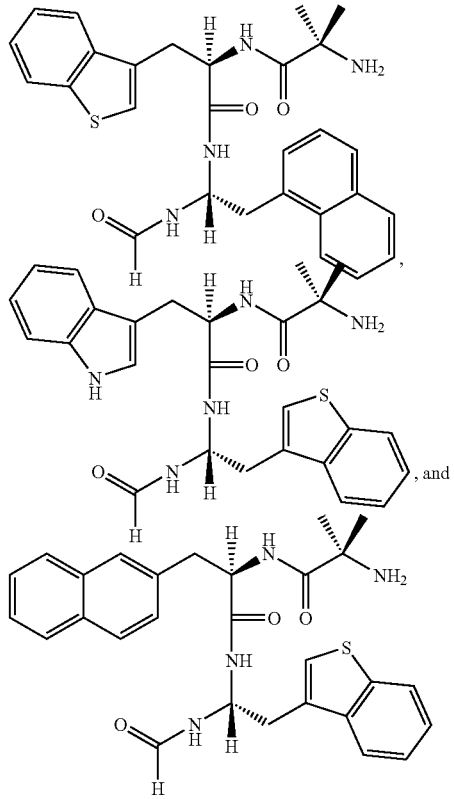

or a pharmaceutically acceptable salt thereof.

49. A pharmaceutical compositions comprising a compound of claim 48.

50. The composition of claim 49, in combination with a pharmaceutically acceptable carrier.

* * * * *